(12) United States Patent
Crescenzi et al.

(10) Patent No.: US 8,314,062 B2
(45) Date of Patent: Nov. 20, 2012

(54) MACROCYCLIC COMPOUNDS AS ANTIVIRAL AGENTS

(75) Inventors: Benedetta Crescenzi, Pomezia (IT); Monica Donghi, Pomezia (IT); Marco Ferrara, Pomezia (IT); Cristina Gardelli, Pomezia (IT); Steven Harper, Pomezia (IT); Uwe Koch, Pomezia (IT); Michael Rowley, Pomezia (IT); Vincenzo Summa, Pomezia (IT)

(73) Assignee: Instituto di Ricerche di Biologia Molecolare P. Angeletti S.p.A., Rome (IT)

( * ) Notice: Subject to any disclaimer, the term of this patent is extended or adjusted under 35 U.S.C. 154(b) by 910 days.

(21) Appl. No.: 12/306,137

(22) PCT Filed: Jun. 21, 2007

(86) PCT No.: PCT/GB2007/050346
§ 371 (c)(1),
(2), (4) Date: Dec. 22, 2008

(87) PCT Pub. No.: WO2007/148135
PCT Pub. Date: Dec. 27, 2007

(65) Prior Publication Data
US 2009/0312241 A1 Dec. 17, 2009

(30) Foreign Application Priority Data
Jun. 23, 2006 (GB) ............... GB0612423.4

(51) Int. Cl.
*A61K 38/00* (2006.01)
(52) U.S. Cl. ........................................ 514/3.7
(58) Field of Classification Search .......... None
See application file for complete search history.

(56) References Cited

U.S. PATENT DOCUMENTS

| | | |
|---|---|---|
| 3,480,613 A | 11/1969 | Walton |
| 6,323,180 B1 | 11/2001 | Llinas-Brunet et al. |
| 6,608,027 B1 | 8/2003 | Tsantrizos et al. |
| 6,777,395 B2 | 8/2004 | Bhat et al. |
| 6,955,184 B2 | 10/2005 | Friedrichs et al. |
| 7,470,664 B2 | 12/2008 | Holloway et al. |
| 2002/0019363 A1 | 2/2002 | Ismaili et al. |
| 2002/0107138 A1 | 8/2002 | Hoveyda et al. |
| 2003/0236216 A1 | 12/2003 | Devos et al. |
| 2004/0006007 A1 | 1/2004 | Gosselin et al. |
| 2004/0063658 A1 | 4/2004 | Roberts et al. |
| 2004/0067901 A1 | 4/2004 | Bhat et al. |
| 2004/0229776 A1 | 11/2004 | Chen et al. |
| 2004/0229818 A1 | 11/2004 | Llinas-Brunet et al. |
| 2004/0254159 A1 | 12/2004 | Hasvold et al. |
| 2004/0266668 A1 | 12/2004 | Nakajima et al. |
| 2005/0020503 A1 | 1/2005 | Llinas-Brunet et al. |
| 2005/0038240 A1 | 2/2005 | Connolly et al. |
| 2006/0257980 A1 | 11/2006 | Li |
| 2007/0027071 A1 | 2/2007 | Holloway et al. |

FOREIGN PATENT DOCUMENTS

| | | |
|---|---|---|
| EP | 1719773 A1 | 11/2006 |
| GB | 2337262 A | 11/1999 |
| GB | 2430621 A | 4/2007 |
| WO | 97/41211 A1 | 11/1997 |
| WO | 98/22496 A2 | 5/1998 |
| WO | 98/46630 A1 | 10/1998 |
| WO | 99/07733 A2 | 2/1999 |
| WO | 99/07734 A2 | 2/1999 |
| WO | 99/38888 A1 | 8/1999 |
| WO | 99/43691 A1 | 9/1999 |
| WO | 99/50230 A1 | 10/1999 |
| WO | 99/64442 A1 | 12/1999 |
| WO | 00/09543 A2 | 2/2000 |
| WO | 00/09546 A2 | 2/2000 |
| WO | 00/25780 A1 | 5/2000 |
| WO | 00/59929 A1 | 10/2000 |
| WO | 01/00622 A1 | 1/2001 |
| WO | 01/47883 A1 | 7/2001 |

(Continued)

OTHER PUBLICATIONS

Youwei Yan et al., Complex of NS3 protease and NS4A peptide of BK strain hepatitis C virus: A 2.2 Angstrom resolution structure in a hexagonal crystal form, 7 Protein Science 837 (1998).
Brian W. Dymock et al., "Novel Approaches to the Treatment of Hepatitis C Virus Infection," 11 Antiviral Chemistry & Chemotherapy 79-96 (2000).
Hugo R. Rosen & David R. Gretch, "Hepatitis C virus: current understanding and prospects for future therapies," 5 Molec. Med. Today 393-99 (1999).
Darius Moradpour & Hubert E. Blum, "Current and evolving therapies for hepatitis C," 11 Euro. J. Gastroenterol. Hepatol. 1189-1202 (1999).
Ralf Bartenschlager, "Candidate Targets for Hepatitis C Virus-Specific Antiviral Therapy," 40(5-6) Intervirology 378-93 (1997).

(Continued)

*Primary Examiner* — Thomas Heard
(74) *Attorney, Agent, or Firm* — Julia M. Lake; Sheldon O. Heber

(57) ABSTRACT

The present invention relates to macrocyclic compounds of formula (I): wherein W, n, m, $R^1$, $R^2$, $R^3$, $R^4$, $R^5$, $R^a$, M, Z and ring B are defined herein, and pharmaceutically acceptable salts thereof, pharmaceutical compositions comprising them, and their use for the treatment or prevention of infection by hepatitis C virus.

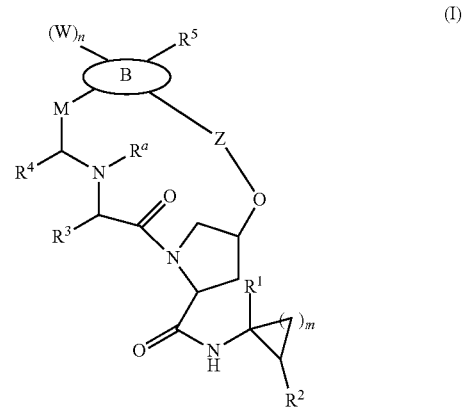

22 Claims, No Drawings

FOREIGN PATENT DOCUMENTS

| | | |
|---|---|---|
| WO | 01/60379 A1 | 8/2001 |
| WO | 01/68663 A1 | 9/2001 |
| WO | 01/77091 A2 | 10/2001 |
| WO | 01/77113 A2 | 10/2001 |
| WO | 01/79246 A2 | 10/2001 |
| WO | 01/90121 A2 | 11/2001 |
| WO | 01/92282 A2 | 12/2001 |
| WO | 02/04425 A1 | 1/2002 |
| WO | 02/06246 A1 | 1/2002 |
| WO | 02/18404 A2 | 3/2002 |
| WO | 02/20497 A1 | 3/2002 |
| WO | 02/32920 A2 | 4/2002 |
| WO | 02/48116 A2 | 6/2002 |
| WO | 02/48165 A2 | 6/2002 |
| WO | 02/48172 A2 | 6/2002 |
| WO | 02/051425 A1 | 7/2002 |
| WO | 02/057287 A2 | 7/2002 |
| WO | 02/057425 A2 | 7/2002 |
| WO | 02/100415 A2 | 12/2002 |
| WO | 03/015755 A1 | 2/2003 |
| WO | 03/026589 A2 | 4/2003 |
| WO | 03/026675 A1 | 4/2003 |
| WO | 03/062192 A1 | 7/2003 |
| WO | 03/062211 A1 | 7/2003 |
| WO | 03/064455 A2 | 8/2003 |
| WO | 03/068244 A1 | 8/2003 |
| WO | 03/093290 A2 | 11/2003 |
| WO | 03/099274 A1 | 12/2003 |
| WO | 2004/000858 A2 | 12/2003 |
| WO | 2004/002422 A2 | 1/2004 |
| WO | 2004/002999 A1 | 1/2004 |
| WO | 2004/003000 A2 | 1/2004 |
| WO | 2004/003138 A2 | 1/2004 |
| WO | 2004/007512 A2 | 1/2004 |
| WO | 2004/011478 A2 | 2/2004 |
| WO | 2004/013300 A2 | 2/2004 |
| WO | 2004/028481 A2 | 4/2004 |
| WO | 2004/041201 A2 | 5/2004 |
| WO | 2004/087714 A1 | 10/2004 |
| WO | 2004/093915 A1 | 11/2004 |
| WO | 2004/103996 A1 | 12/2004 |
| WO | 2004/110442 A1 | 12/2004 |
| WO | 2005/003147 A2 | 1/2005 |
| WO | 2005/016927 A1 | 2/2005 |
| WO | 2005/023819 A1 | 3/2005 |
| WO | 2005/034941 A1 | 4/2005 |
| WO | 2005/046712 A1 | 5/2005 |
| WO | 2005/070955 A1 | 8/2005 |
| WO | 2005/080399 A1 | 9/2005 |
| WO | 2006/008556 A1 | 1/2006 |
| WO | 2006/020082 A1 | 2/2006 |
| WO | 2006/021341 A1 | 3/2006 |
| WO | 2006/027628 A2 | 3/2006 |
| WO | 2006/029912 A1 | 3/2006 |
| WO | 2006/046030 A1 | 5/2006 |
| WO | 2006/046039 A2 | 5/2006 |
| WO | 2006/119061 A2 | 11/2006 |
| WO | 2006/119975 A1 | 11/2006 |
| WO | 2007/015787 A1 | 2/2007 |
| WO | 2007/015855 A1 | 2/2007 |
| WO | 2007/016441 A1 | 2/2007 |
| WO | 2007/028789 A1 | 3/2007 |
| WO | 2007/029029 A2 | 3/2007 |
| WO | 2007/131966 A1 | 11/2007 |
| WO | 2007/145894 A2 | 12/2007 |
| WO | 2007/148135 A1 | 12/2007 |
| WO | 2008/051475 A2 | 5/2008 |
| WO | 2008/051477 A2 | 5/2008 |
| WO | 2008/051514 A2 | 5/2008 |
| WO | 2008/057028 A1 | 5/2008 |
| WO | 2008/057208 A2 | 5/2008 |
| WO | 2008/057209 A1 | 5/2008 |
| WO | 2008/112108 A1 | 9/2008 |
| WO | 2009/005687 A1 | 1/2009 |
| WO | 2009/010804 A1 | 1/2009 |
| WO | 2009/064955 A1 | 5/2009 |
| WO | 2009/064975 A1 | 5/2009 |

OTHER PUBLICATIONS

Georg M. Lauer & Bruce D. Walker, "Hepatitis C Virus Infection," 345(1) N. Engl. J. Med. 41-52 (2001); correction: 345 (19) N. Engl. J. Med. 1425-26 (2001).

Brain W. Dymock, "Emerging therapies for hepatitis C virus infection," 6 Emerging Drugs 13-42 (2001).

Charlene Crabb, Infectious Diseases. "Hard-Won Advances Spark Excitement about Hepatitis C," Science 506-507 (2001).

Rogers E. Harry-O'Kuru et al., "A Short, Flexible Route toward 2'-C-Branched Ribonucleosides," 62 J. Org. Chem. 1754-59 (1997).

Michael S. Wolfe & Rogers E. Harry-O'Kuru, "A Concise Synthesis of 2'-C-Methylribonucleosides," 36(42) Tetrahedron Letters 7611-14 (1995).

Scott J. Miller et al., "Application of Ring-Closing Metathesis to the Synthesis of Rigidified Amino Acids and Peptides," 118 J. Am. Chem. Soc. 9606-14 (1996).

Jason S. Kingsbury et al., "A Recyclable Ru-Based Metathesis Catalyst," 121 J. Am. Chem. Soc. 791-99 (1999).

Matthias Scholl et al., "Synthesis and Activity of a New Generation of Ruthenium-Based Olefin Metathesis Catalysts Coordinated with 1,3-Dimesityl-4,5-dihydroimidazol-2-ylidene Ligands," 1(6) Organic Letters 953-56 (1999).

Alois Furstner et al., "Total Synthesis and Structural Refinement of the Cyclic Tripyrrole Pigment Nonylprodigiosin," 64 J. Org. Chem. 8275-80 (1999).

Tina M. Trnka & Robert H. Grubbs, "The Development of L2X2R-CHR Olefin Metathesis Catalysts: An Organometallic Success Story," 34 Acc. Chem. Res. 18-29 (2001).

A. Srikrishna et al., "Enantiospecific Construction of the BC-ring System of Taxanes," 45 Tetrahedron Letters 2939-42 (2004).

Yung-Son Hon et al., "Dibromomethane as one-carbon source in organic synthesis: a versatile methodology to prepare the cyclic and acyclic alpha-methylene or alpha-keto acid derivatives from the corresponding terminal alkenes," 60 Tetrahedron 4837-60 (2004).

Eusebio Juaristi & Hugo A. Jimenez-Vazquez, "Single Electron Transfer Mechanism in the Reaction of 1,3-Dithianyllithium and Alkyl Iodides," 56 J. Org. Chem. 1623-30 (1991).

Paola Conti et al., "Chemoenzymatic Synthesis of the Enantiomers of Desoxymuscarine," 9 Tetrahedron: Asymmetry 657-65 (1998).

Robert M. Coates & Mark W. Johnson, "Stereoselective Synthesis of Moenocinol and Assignment of Its Carbon-13 Nuclear Magnetic Resonance Spectrum," 45 J. Org. Chem. 2685-97 (1980).

D. Becker & N. Haddad, "Steric Effects in Intramolecular [2+2] Photocycloaddition of C=C Double Bonds to Cyclohexenones," 49(4) Tetrahedron 947-64 (1993).

Richard A. Bunce et al., "Tandem SN2-Michael Reactions for the Preparation of Simple Five- and Six-Membered-Ring Nitrogen and Sulfur Heterocycles," 57 J. Org. Chem. 1727-33 (1992).

Masao Tokuda et al., "Aminyl Radical Cyclization by Means of Anodic Oxidation. Stereoselective Synthesis of cis-1-Methyl-2,5-Disubstituted Pyrrolidines," 26(49) Tetrahedron Letters 6085-88 (1985).

Robert Haner et al., "174. Generation and Reactions of Lithiated tert-Butyl and 2,6-Di(tert-butyl)-4-methylphenyl Cyclopropanecarboxylates," 69 Helvetica Chimica Acta 1655-65 (1986).

Herbert O. House et al., "Cyclization of Unsaturated Hydroxylamine Derivatives," 41(5) J. Org. Chem. 855-63 (1976).

Theophil Eicher et al., "Bryophyte Constituents; 7: New Synthesis of (+)-Rosmarinic Acid and Related Compounds," Synthesis 755-62 (Jun. 1996).

Michael C. Venuti et al., "Inhibitors of Cyclic AMP Phosphodiesterase. 3. Synthesis and Biological Evaluation of Pyrido and Imidazolyl Analogues of 1,2,3,5-Tetrahydro-2-oxoimidazo[2,1-b]quinazoline," 31 J. Med. Chem. 2136-45 (1988).

Marc-Andre Poupart et al., "Solid-Phase Synthesis of Peptidomimetic Inhibitors for the Hepatitis C Virus NS3 Protease," 66(14) J. Org. Chem. 4743-51 (2001).

Nigel J. Liverton et al., Molecular Modeling Based Approach to Potent P2-P4 Macrocyclic Inhibitors of Hepatitis C NS3/NS4A Protease, 130 J. Am. Chem. Soc. 4607-09 (2008).

Anthony C. Allison & Elsie M. Eugui, "Immunosuppressive and other anti-rheumatic activities of mycophenolate mofetil," 44 Agents and Actions Supplements 165-88 (1993).

Joel Kirschbaum, "Amantadine," 12 Profiles of Drug Substances, Excipients and Related Methodology 1-36 (1983).

T. K. Chakaborty et al., "Alpha-Phenylglycinol as chiral auxilliary in diastereoselective Strecker synthesis of alpha-amino acids," 51(33) Tetrahedron 9179-90 (1995).

W. Clark Still et al., "Rapid Chromatographic Technique for Preparative Separations with Moderate Resolution," 43(14) J. Org. Chem. 2923-25 (1978).

Michael D. Cooke et al., "The occurrence of a hydride shift in the aromatization of 1,4-epoxy-1,2-dihydronaphthalenes," 11 J. Chem. Soc. Perkin Trans. I: Phys. Org. Chem. 1377 (1984).

Paul Aeberli et al., "Neuropharmacological investigation of N-benzylsulfamides," 10(4) J. Med. Chem. 636-42 (1967).

Nathalie Goudreau & Montse Llinas-Brunet, "The Therapeutic Potential of NS3 Protease Inhibitors in HCV Infection," 14(9) Expert Opinion 1129-44 (2005).

Volker Lohmann et al., "Selective Stimulation of Hepatitis C Virus and Pestivirus NS5B RNA Polymerase Activity by GTP," 274(16) J. Bio. Chem. 10807-15 (1999).

V. Lohmann et al., "Replication of Subgenomic Hepatitis C Virus RNAs in a Hepatoma Cell Line," 285 Science 110-13 (1999).

Kevin X. Chen et al. "Novel Potent Hepatitis C Virus NS3 Serine Protease Inhibitors Derived from Proline-Based Macrocycles," 49 J. Med. Chem. 995-1005 (2006).

Yuri Goldberg et al., "Highly regioselective bromination of 2,3-dimethylanisole with N-bromosuccinimide," 57 J. Org. Chem. 6374-76 (1992).

Manfred Schlosser et al., "8-Methoxyisoquinoline derivatives through ortho-selective metallation of 2-(3-methoxyphenyl)ethylamines," 32(17) Tetrahedron Letters 1965-66 (1991).

Angela Casini et al., "Carbonic Anhydrase inhibitors inhibition of cytosolic isozymes I and II with sulfamide derivatives," 13(5) Bioorg. Med. Chem. Lett. 837-40 (2003).

Kiyotaka Onisuka et al., "A novel route to 2,3-disubstituted indoles via palladium-catalyzed three-component coupling of aryl iodide, o-alkenylphenyl isocyanide and amine," 43 Tetrahedron Letters 6197-99 (2002).

Duane E. Rudisill & J. K. Stille, "Palladium-catalyzed synthesis of 2-substituted indoles," 54(25) J. Org. Chem. 5856-66 (2002).

Makoto Satoh et al., "Palladium-Catalyzed Cross-Coupling Reaction of (1-Ethoxy-1-alken-2-yl)boranes With ortho-Functionalized Iodoarenes. A Novel and Convenient Synthesis of Benzo-Fused Heteroaromatic Compounds," Synthesis Communications 373-377 (Apr. 1987).

Yuusaku Yokoyama et al., "Palladium-Catalyzed Reaction of 3-Bromoindole Derivative with Allyl Esters in the Presence of Hexa-n-butyldistannane," 31(8) Heterocycles 1505-11 (1990).

Steven W. Ludmerer et al., "A transient cell-based phenotype assay for hepatitis C NS3/4A protease: Application to potency determinations of a novel macrocyclic inhibitor against diverse protease sequences isolated from plasma infected with HCV," 151 Journal of Virological Methods 301-07 (2008).

John A. McCauley et al., "Bismacrocyclic Inhibitors of Hepatitis C NS3/4a Protease," 47 Angew. Chem. Int. Ed. 9104-07 (2008).

Ashok Arasappan et al., "P2-P4 Macrocyclic inhibitors of hepatitis C virus NS3-4A serine protease," 16 Bioorganic & Medicinal Chemistry Letters 3960-65 (2006).

MACROCYCLIC COMPOUNDS AS ANTIVIRAL AGENTS

CROSS-REFERENCE TO RELATED APPLICATIONS

This application is a National Stage of International application PCT/GB2007/0050346, filed Jun. 21, 2007. This application also claims priority to British Provisional application No. GB 0612423.4, filed Jun. 23, 2006.

FIELD OF THE INVENTION

The present invention relates to macrocyclic compounds that are useful as inhibitors of the hepatitis C virus (HCV) NS3 protease, their synthesis, and their use for treating or preventing HCV infection.

BACKGROUND OF THE INVENTION

Hepatitis C virus (HCV) infection is a major health problem that leads to chronic liver disease, such as cirrhosis and hepatocellular carcinoma, in a substantial number of infected individuals, estimated to be 2-15% of the world's population. According to the World Health Organization, there are more than 170 million infected individuals worldwide, with at least 3 to 4 million people being infected each year. Once infected, about 20% of people clear the virus, but the rest harbor HCV the rest of their lives. Ten to twenty percent of chronically infected individuals eventually develop liver-destroying cirrhosis or cancer. The viral disease is transmitted parenterally by contaminated blood and blood products, contaminated needles, or sexually and vertically from infected mothers or carrier mothers to their offspring.

Current treatments for HCV infection, which are restricted to immunotherapy with recombinant interferon-α alone or in combination with the nucleoside analog ribavirin, are of limited clinical benefit. Moreover, there is no established vaccine for HCV. Consequently, there is an urgent need for improved therapeutic agents that effectively combat chronic HCV infection.

Several virally-encoded enzymes are putative targets for therapeutic intervention, including a metalloprotease (NS2-3), a serine protease (NS3), a helicase (NS3), and an RNA-dependent RNA polymerase (NS5B). The NS3 protease is located in the N-terminal domain of the NS3 protein, and is considered a prime drug target since it is responsible for an intramolecular cleavage at the NS3/4A site and for downstream intermolecular processing at the NS4A/4B, NS4B/5A and NS5A/5B junctions. Previous research has identified classes of peptides, such as hexapeptides as well as tripeptides discussed in U.S. patent applications US2005/0020503, US2004/0229818, and US2004/00229776, showing degrees of activity in inhibiting the NS3 protease. The aim of the present invention is to provide further compounds which exhibit activity against the HCV NS3 protease.

Macrocyclic compounds that exhibit activity against the HCV NS3 protease have already been disclosed in published International patent application nos. WO2006/119061, WO2007/015855 and WO2007/016441 (all Merck & Co., Inc.)

SUMMARY OF THE INVENTION

Thus, in one aspect, there is provided the compound of formula (I):

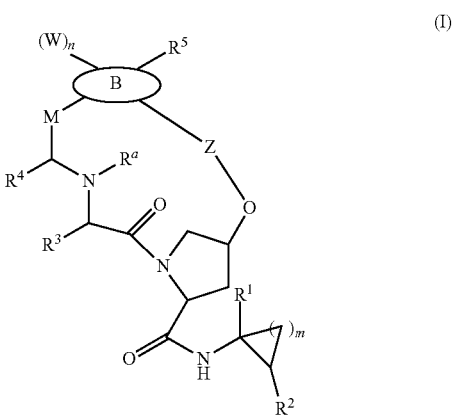

or a pharmaceutically acceptable salt thereof, wherein:

m is 1, 2, 3 or 4;
n is 0, 1 or 2;
$R^1$ is $CO_2R^6$, $CONR^6SO_2R^6$ or $CONR^6SO_2N(R^6)_2$;
$R^2$ is H, $C_{1-6}$alkyl, $C_{2-6}$alkenyl or $C_{3-8}$cycloalkyl, wherein said alkyl, alkenyl or cycloalkyl is optionally substituted with 1 to 3 halo;
$R^3$ is $C_{1-6}$alkyl, $(CH_2)_{0-3}C_{3-8}$cycloalkyl, $(CH_2)_{0-3}$aryl or $(CH_2)_{0-3}$Het, optionally substituted by halo, $OR^6$, $SR^6$, $N(R^6)_2$, $C_{1-6}$alkyl, $NO_2$, CN, $CF_3$, $NR^6SO_2R^6$, $SO_2N(R^6)_2$, $NHCO_2R^6$, $NHCOR^6$, $NHCONHR^6$, $CO_2R^6$, $C(O)R^6$ or $CON(R^6)_2$;
$R^4$ is hydrogen, halo, hydroxy, $C_{1-6}$alkyl, $C_{2-6}$alkenyl, $C_{2-6}$alkynyl, $(CH_2)_{0-3}C_{3-8}$cycloalkyl, $(CH_2)_{0-3}$aryl or $C_{1-6}$alkoxy, optionally substituted by halo, $OR^6$, $SR^6$, $N(R^6)_2$, $C_{1-6}$alkyl, $NO_2$, CN, $CF_3$ $NR^6SO_2R^6$, $SO_2N(R^6)_2$, $NHCO_2R^6$, $NHCOR^6$, $NHCONHR^6$, $CO_2R^6$, $C(O)R^6$ or $CON(R^6)_2$;
$R^5$ is hydrogen, halo, hydroxy, $C_{1-6}$alkyl, $C_{1-6}$alkoxy, CN, $NO_2$, $C_{3-8}$cycloalkyl, $N(R^6)_2$, aryl or heteroaryl, optionally substituted by 1 to 8 halo, $C_{1-4}$alkyl or $N(R^6)_2$;
each $R^6$ is independently hydrogen, $C_{1-6}$alkyl or $C_{3-8}$cycloalkyl;
$R^a$ is hydrogen or $C_{1-4}$alkyl;
or $R^a$ and $R^3$ are joined to form a 5- to 7-membered heterocycle containing 1, 2 or 3 N atoms, which heterocycle is optionally substituted by $C_{1-4}$alkyl;
each W is independently halo, $OR^6$, $C_{1-6}$alkyl, CN, $NO_2$, $CF_3$, $OCF_3$, $OCHF_2$, $CO_2R^6$, $CON(R^6)_2$, $COR^6$, $NR^6C(O)R^6$, aryl or heteroaryl;
Z is a bond, —$CH_2$— or C=O;
M is $C_{2-12}$alkylene or $C_{2-12}$alkenylene, optionally substituted by halo, $C_{1-6}$alkyl, $(CH_2)_{0-3}C_{3-8}$cycloalkyl or $(CH_2)_{0-3}$aryl, and optionally containing O, $NR^6$, S, SO or $SO_2$; and
ring B is

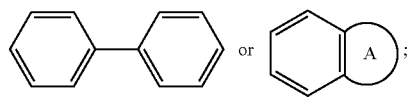

and
ring A is pyridinyl, pyrrolidinyl or pyrimidinyl.

DETAILED DESCRIPTION OF THE INVENTION

In one embodiment of the present invention, there is provided the compound of formula (Io):

(Io)

or a pharmaceutically acceptable salt thereof,
wherein:
m is 1, 2, 3 or 4;
n is 0, 1 or 2;
$R^1$ is $CO_2R^6$, $CONR^6SO_2R^6$ or $CONR^6SO_2N(R^6)_2$;
$R^2$ is H, $C_{1-6}$alkyl, $C_{2-6}$alkenyl or $C_{3-8}$cycloalkyl, wherein said alkyl, alkenyl or cycloalkyl is optionally substituted with 1 to 3 halo;
$R^3$ is $C_{1-6}$alkyl, $(CH_2)_{0-3}C_{3-8}$cycloalkyl, $(CH_2)_{0-3}$aryl or $(CH_2)_{0-3}$Het, optionally substituted by halo, $OR^6$, $SR^6$, $N(R^6)_2$, $C_{1-6}$alkyl, $NO_2$, CN, $CF_3$, $NR^6SO_2R^6$, $SO_2N(R^6)_2$, $NHCO_2R^6$, $NHCOR^6$, $NHCONHR^6$, $CO_2R^6$, $C(O)R^6$ or $CON(R^6)_2$;
$R^4$ is hydrogen, $C_{1-6}$alkyl, $C_{2-6}$alkenyl, $C_{2-6}$alkynyl, $(CH_2)_{0-3}C_{3-8}$cycloalkyl, $(CH_2)_{0-3}$aryl or $C_{1-6}$alkoxy, optionally substituted by halo, $OR^6$, $SR^6$, $N(R^6)_2$, $C_{1-6}$alkyl, $NO_2$, CN, $CF_3$ $NR^6SO_2R^6$, $SO_2N(R^6)_2$, $NHCO_2R^6$, $NHCOR^6$, $NHCONHR^6$, $CO_2R^6$, $C(O)R^6$ or $CON(R^6)_2$;
$R^5$ is hydrogen, halo, hydroxy, $C_{1-6}$alkyl, $C_{1-6}$alkoxy, CN, $NO_2$, $C_{3-8}$cycloalkyl, $N(R^6)_2$, aryl or heteroaryl, optionally substituted by 1 to 8 halo, $C_{1-4}$alkyl or $N(R^6)_2$;
each $R^6$ is independently hydrogen, $C_{1-6}$alkyl or $C_{3-8}$cycloalkyl;
$R^a$ is hydrogen or $C_{1-4}$alkyl;
or $R^a$ and $R^3$ are joined to form a 5- to 7-membered heterocycle containing 1, 2 or 3 N atoms, which heterocycle is optionally substituted by $C_{1-4}$alkyl;
each W is independently halo, $OR^6$, $C_{1-6}$alkyl, CN, $NO_2$, $CF_3$, $OCF_3$, $OCHF_2$, $CO_2R^6$, $CON(R^6)_2$, $COR^6$, $NR^6C(O)R^6$, aryl or heteroaryl;
Z is a bond or C=O;
M is $C_{2-12}$alkylene or $C_{2-12}$alkenylene, optionally substituted by halo, $C_{1-6}$alkyl, $(CH_2)_{0-3}C_{3-8}$cycloalkyl or $(CH_2)_{0-3}$aryl, and optionally containing O, $NR^6$, S, SO or $SO_2$; and
ring A is pyridinyl, pyrrolidinyl or pyrimidinyl.
In another embodiment of the present invention, m is 1 or 2. Preferably, m is 1.
In another embodiment of the present invention, n is 0 or 1. Preferably, n is 0.
In another embodiment, $R^1$ is $CO_2R^6$, $CONR^6SO^2R^6$ or $CONR^6SO_2N(R^6)_2$ where $R^6$ is as hereinbefore defined. Preferably, $R^1$ is $CO_2R^6$ or $CONR^6SO_2R^6$ where $R^6$ is as hereinbefore defined. More preferably, $R^1$ is $CO_2H$ or $CONHSO_2R^6$ where $R^6$ is as hereinbefore defined. Especially, $R^1$ is $CO_2H$ or $CONHSO_2$—$C_{3-8}$cycloalkyl. More especially, $R^1$ is $CO_2H$ or $CONHSO_2$—$C_{3-6}$cycloalkyl. Most especially, $R^1$ is $CO_2H$ or $CONHSO_2$-cyclopropyl.

In another embodiment, $R^2$ is $C_{1-6}$alkyl or $C_{2-6}$alkenyl. Preferably, $R^2$ is $C_{1-4}$alkyl or $C_{2-4}$alkenyl. More preferably, $R^2$ is $C_{1-2}$alkyl or —CH=CH_2. Most preferably, $R^2$ is ethyl or —CH=CH_2.

In another embodiment, $R^3$ is $C_{1-6}$alkyl, or $(CH_2)_{0-3}C_{3-8}$cycloalkyl, optionally substituted by halo, $OR^6$ or $C_{1-6}$alkyl, where $R^6$ is as hereinbefore defined. Preferably, $R^3$ is $C_{1-6}$alkyl or $(CH_2)_{0-3}C_{3-8}$cycloalkyl, optionally substituted by halo. More preferably, $R^3$ is $C_{1-4}$alkyl or $C_{3-6}$cycloalkyl, optionally substituted by fluoro or chloro. Most preferably, $R^3$ is methyl, propyl, butyl, cyclopentyl or cyclohexyl, optionally substituted by fluoro. Especially, $R^3$ is methyl, $^i$propyl, $^t$butyl, $CF_3$, cyclopentyl or cyclohexyl.

In another embodiment, $R^a$ is hydrogen or $C_{1-2}$alkyl. Preferably, $R^a$ is hydrogen or methyl.

In another embodiment, $R^a$ and $R^3$ are joined to form a 5- or 6-membered heterocycle containing 1 or 2 N atoms, which heterocycle is optionally substituted by $C_{1-4}$alkyl. Preferably, $R^a$ and $R^3$ are joined to form a 5- or 6-membered heterocycle containing one N atom, which heterocycle is optionally substituted by $C_{1-4}$alkyl. More preferably, $R^a$ and $R^3$ are joined to form a pyrrolidinyl or a piperidinyl ring, optionally substituted by $C_{1-2}$alkyl. Most preferably, $R^a$ and $R^3$ are joined to form a pyrrolidinyl ring, optionally substituted by methyl. Especially, $R^a$ and $R^3$ form where * indicates the nitrogen atom to which $R^a$ is attached and ** indicates the carbon atom to which $R^3$ is attached.

In another embodiment, $R^4$ is hydrogen, $C_{1-6}$alkyl, $(CH_2)_{0-3}C_{3-8}$cycloalkyl, $(CH_2)_{0-3}$-phenyl or $C_{1-6}$alkoxy, optionally substituted by halo, $OR^6$, $SR^6$, $N(R^6)_2$, $C_{1-6}$alkyl, $NO_2$ or CN, where $R^6$ is as hereinbefore defined. Preferably, $R^4$ is hydrogen, $C_{1-6}$alkyl or $C_{1-6}$alkoxy, optionally substituted by halo or $OR^6$, where $R^6$ is as hereinbefore defined. More preferably, $R^4$ is hydrogen or $C_{1-6}$alkyl, optionally substituted by halo. Most preferably, $R^4$ is hydrogen or $C_{1-4}$alkyl, optionally substituted by fluoro or chloro. Especially, $R^4$ is hydrogen or $C_{1-2}$alkyl, optionally substituted by fluoro. Examples of suitable $R^4$ groups include hydrogen, methyl, $CF_3$ and $CF_2CF_3$.

In another embodiment, $R^5$ is hydrogen, halo, hydroxy, $C_{1-6}$alkyl, $C_{1-6}$alkoxy, $C_{3-8}$cycloalkyl, aryl or heteroaryl, optionally substituted by $N(R^6)_2$. Preferably, $R^5$ is hydrogen, $C_{1-6}$alkyl, $C_{3-8}$cycloalkyl, phenyl or thiazolyl, optionally substituted by $NHR^6$. More preferably, $R^5$ is hydrogen, $C_{1-4}$alkyl, phenyl or thiazolyl, where thiazolyl is optionally substituted by $NHR^6$. Most preferably, $R^5$ is hydrogen, phenyl or When $R^5$ is other than hydrogen, preferably it is attached to the carbon atom adjacent to the nitrogen atom of the pyridinyl, pyrrolidinyl or pyrimidinyl moiety.

In another embodiment, each W is independently halo, $OR^6$, $C_{1-6}$alkyl, $CF_3$, $CO_2R^6$, $CON(R^6)_2$, $COR^6$ or $NR^6C(O)R^6$, where $R^6$ is as hereinbefore defined. Preferably, each W is independently halo, $OR^6$, $CF_3$, $CO_2R^6$ or $CONHR^6$, where $R^6$ is as hereinbefore defined. More preferably, each W is independently fluoro, chloro, $OC_{1-6}$alkyl or $CF_3$. Most preferably, each W is independently $OC_{1-4}$alkyl or $CF_3$. Especially, each W is independently $OC_{1-2}$alkyl. Most especially, W is methoxy.

In another embodiment, Z is a bond when A is pyridinyl or pyrimidinyl.

In another embodiment, Z is C=O when A is pyrrolidinyl. Preferably, Z is attached to the nitrogen atom of the pyrrolidinyl moiety.

In another embodiment, Z is —CH$_2$— when ring B is biphenyl.

In another embodiment, M is $C_{2-8}$alkylene or $C_{2-8}$alkenylene, optionally substituted by halo, $C_{1-4}$alkyl or $C_{3-6}$cycloalkyl, and optionally containing O. Preferably, M is $C_{4-7}$alkylene or $C_{4-7}$alkenylene, optionally substituted by fluoro, chloro or $C_{1-4}$alkyl, and optionally containing O. More preferably, M is $C_{5-7}$alkylene or $C_{5-7}$alkenylene, optionally substituted by fluoro or methyl, and optionally containing O. Examples of suitable M groups include pentylene, hexylene, heptylene,

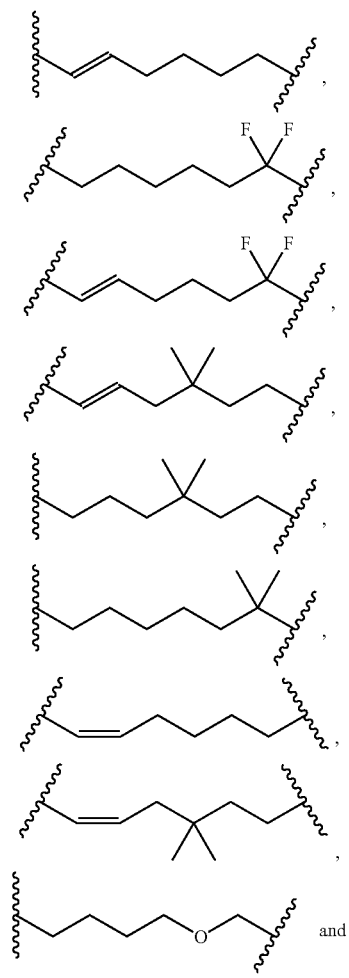

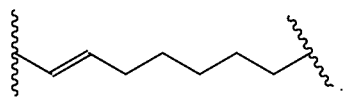

In another embodiment, ring A is pyridinyl or pyrrolidinyl.

In another embodiment of the present invention, there is provided the compound of formula (Ia):

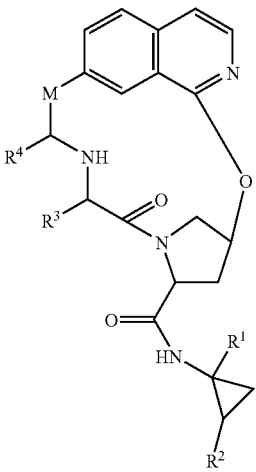

(Ia)

or a pharmaceutically acceptable salt thereof, wherein $R^1$, $R^2$, $R^4$ and M are as defined in relation to formula (I).

Preferably, $R^1$ is $C(O)NR^6SO_2R^6$ where $R^6$ is as defined in relation to formula (I). More preferably, $R^1$ is $C(O)NHSO_2R^6$ where $R^6$ is as defined in relation to formula (I). Most preferably, $R^1$ is $C(O)NHSO_2$—$C_{3-6}$cycloalkyl. Especially $R^1$ is $C(O)NHSO_2$-cyclopropyl.

Preferably, $R^2$ is $C_{2-6}$alkenyl. More preferably, $R^2$ is —CH=CH$_2$.

Preferably, $R^3$ is $C_{1-6}$alkyl or $(CH_2)_{0-3}C_{3-8}$cycloalkyl, optionally substituted by halo. More preferably, $R^3$ is $C_{1-4}$alkyl or $C_{3-6}$cycloalkyl, optionally substituted by fluoro or chloro. Most preferably, $R^3$ is $C_{1-4}$alkyl or $C_{5-6}$cycloalkyl, optionally substituted by fluoro. Especially, $R^3$ is $^i$propyl, cyclopentyl or $CF_3$.

Preferably, $R^4$ is hydrogen, halo, hydroxy, $C_{1-6}$alkyl, $C_{1-6}$alkoxy, $C_{3-8}$cycloalkyl or phenyl, optionally substituted by halo or $OR^6$, where $R^6$ is as hereinbefore defined. More preferably, $R^4$ is hydrogen, $C_{1-6}$alkyl or $C_{3-8}$cycloalkyl, optionally substituted by halo. Most preferably, $R^4$ is hydrogen or $C_{1-4}$alkyl, optionally substituted by fluoro or chloro. Especially, $R^4$ is hydrogen or $C_{1-2}$alkyl, optionally substituted by fluoro. More especially, $R^4$ is hydrogen, methyl or $CF_3$.

Preferably, M is $C_{3-12}$alkylene or $C_{3-12}$alkenylene, optionally substituted by halo or $C_{1-6}$alkyl. More preferably, M is $C_{4-8}$alkylene or $C_{4-8}$alkenylene, optionally substituted by fluoro or $C_{1-4}$alkyl. Most preferably, M is $C_{6-7}$alkylene or $C_{6-7}$alkenylene, optionally substituted by $C_{1-2}$alkyl. Especially, M is hexylene or

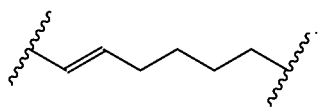

In another embodiment of the present invention, there is provided the compound of formula (Ib):

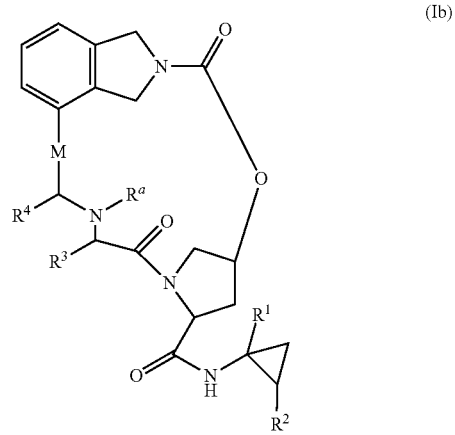

(Ib)

or a pharmaceutically acceptable salt thereof,
wherein $R^1$, $R^2$, $R^4$ and M are as defined in relation to formula (I).

Preferably, $R^1$ is $CO_2R^6$ or $C(O)NR^6SO_2R^6$ where $R^6$ is as defined in relation to formula (I). More preferably, $R^1$ is $CO_2R^6$ or $C(O)NHSO_2R^6$ where $R^6$ is as defined in relation to formula (I). Most preferably, $R^1$ is $CO_2H$ or $C(O)NHSO_2$—$C_{3-6}$cycloalkyl. Especially $R^1$ is $CO_2H$ or $C(O)NHSO_2$-cyclopropyl.

Preferably, $R^2$ is $C_{1-4}$alkyl or $C_{2-4}$alkenyl. More preferably, $R^2$ is $C_{1-2}$alkyl or —CH=$CH_2$. Most preferably, $R^2$ is ethyl or —CH=$CH_2$.

Preferably, $R^3$ is $C_{1-6}$alkyl or $(CH_2)_{0-3}C_{3-8}$cycloalkyl, optionally substituted by halo. More preferably, $R^3$ is $C_{1-4}$alkyl or $C_{3-6}$cycloalkyl, optionally substituted by fluoro or chloro. Most preferably, $R^3$ is $C_{1-4}$alkyl or $C_{5-6}$cycloalkyl, optionally substituted by fluoro. Especially, $R^3$ is methyl, $^i$propyl, $^t$butyl, $CF_3$, cyclopentyl or cyclohexyl.

Preferably, $R^a$ is hydrogen or $C_{1-2}$alkyl. More preferably, $R^a$ is hydrogen or methyl.

Preferably, $R^a$ and $R^3$ are joined to form a 5- or 6-membered heterocycle containing 1 or 2 N atoms, which heterocycle is optionally substituted by $C_{1-4}$alkyl. More preferably, $R^a$ and $R^3$ are joined to form a 5- or 6-membered heterocycle containing one N atom, which heterocycle is optionally substituted by $C_{1-4}$alkyl. Most preferably, $R^a$ and $R^3$ are joined to form a pyrrolidinyl or a piperidinyl ring, optionally substituted by $C_{1-2}$alkyl. Especially, $R^a$ and $R^3$ are joined to form a pyrrolidinyl ring, optionally substituted by methyl. More especially, $R^a$ and $R^3$ form

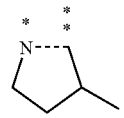

where * indicates the nitrogen atom to which $R^a$ is attached and ** indicates the carbon atom to which $R^3$ is attached.

Preferably, $R^4$ is hydrogen, halo, hydroxy, $C_{1-6}$alkyl, $C_{1-6}$alkoxy, $C_{3-8}$cycloalkyl or phenyl, optionally substituted by halo or $OR^6$, where $R^6$ is as hereinbefore defined. More preferably, $R^4$ is hydrogen, $C_{1-6}$alkyl or $C_{3-8}$cycloalkyl, optionally substituted by halo. Most preferably, $R^4$ is hydrogen or $C_{1-4}$alkyl, optionally substituted by fluoro or chloro. Especially, $R^4$ is hydrogen or $C_{1-2}$alkyl, optionally substituted by fluoro. More especially, $R^4$ is hydrogen, methyl, $CF_3$ or $CF_2CF_3$.

Preferably, M is $C_{2-8}$alkylene or $C_{2-8}$alkenylene, optionally substituted by halo or $C_{1-6}$alkyl. More preferably, M is $C_{4-7}$alkylene or $C_{4-7}$alkenylene, optionally substituted by fluoro, chloro or $C_{1-4}$alkyl. Most preferably, M is $C_{5-7}$alkylene or $C_{5-7}$alkenylene, optionally substituted by fluoro or $C_{1-2}$alkyl. Especially, M is pentylene, hexylene,

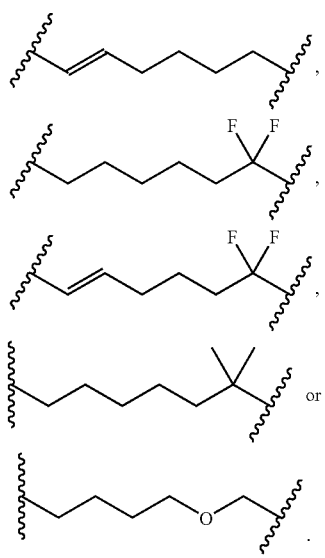

In another embodiment of the present invention, there is provided the compound of formula (Ic):

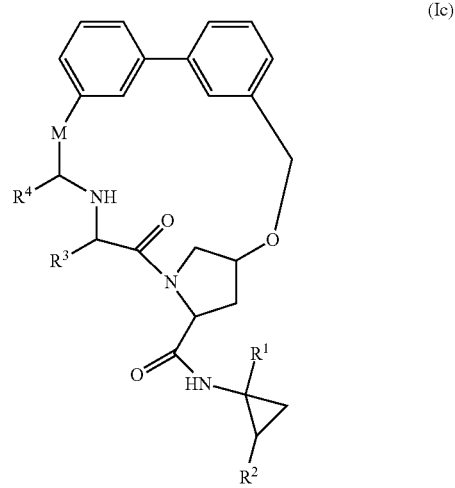

(Ic)

or a pharmaceutically acceptable salt thereof, wherein $R^1$, $R^2$, $R^3$, $R^4$ and M are defined in relation to formula (I).

Preferably, $R^1$ is $C(O)NR^6SO_2R^6$ where $R^6$ is as defined in relation to formula (I). More preferably, $R^1$ is $C(O)NHSO_2R^6$ where $R^6$ is as defined in relation to formula (I). Most preferably, $R^1$ is $C(O)NHSO_2$—$C_{3-6}$cycloalkyl. Especially, $R^1$ is $C(O)NHSO_2$-cyclopropyl.

Preferably, $R^2$ is $C_{2-6}$alkenyl. More preferably, $R^2$ is —CH=CH$_2$.

Preferably, $R^3$ is $C_{1-6}$alkyl or $(CH_2)_{0-3}C_{3-8}$cycloalkyl, optionally substituted by halo. More preferably, $R^3$ is $C_{1-4}$alkyl or $C_{3-6}$cycloalkyl. Most preferably, $R^3$ is $C_{3-4}$alkyl or $C_{5-6}$cycloalkyl. Especially, $R^3$ is $^t$butyl or cyclohexyl.

Preferably, $R^4$ is hydrogen or $C_{1-6}$alkyl. More preferably, $R^4$ is hydrogen or $C_{1-4}$alkyl. Most preferably, $R^4$ is hydrogen or $C_{1-2}$alkyl. Especially, $R^4$ is hydrogen.

Preferably, M is $C_{2-8}$alkylene pr $C_{2-8}$alkenylene, optionally substituted by halo or $C_{1-6}$alkyl. More preferably, M is $C_{3-7}$alkylene or $C_{3-7}$alkenylene, optionally substituted by $C_{1-4}$alkyl. Most preferably, M is $C_{4-6}$alkenylene or $C_{4-6}$alkenylene, optionally substituted by $C_{1-2}$alkyl. Especially, M is pentylene or

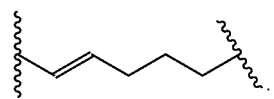

In another embodiment of the present invention, there is provided the compound of formula (Id):

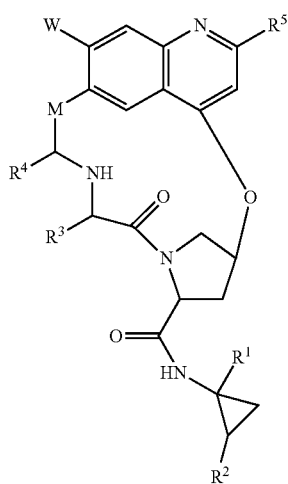

(Id)

or a pharmaceutically acceptable salt thereof,
wherein $R^1$, $R^2$, $R^3$, $R^4$, $R^5$, M and W are defined in relation to formula (I).

Preferably, $R^1$ is $C(O)NR^6SO_2R^6$ where $R^6$ is as defined in relation to formula (I). More preferably, $R^1$ is $C(O)NHSO_2R^6$ where $R^6$ is as defined in relation to formula (I). Most preferably, $R^1$ is $C(O)NHSO_2$—$C_{3-6}$cycloalkyl. Especially, $R^1$ is $C(O)NHSO_2$-cyclopropyl.

Preferably, $R^2$ is $C_{2-6}$alkenyl. More preferably, $R^2$ is —CH=CH$_2$.

Preferably, $R^3$ is $C_{1-6}$alkyl or $(CH_2)_{0-3}C_{3-8}$cycloalkyl, optionally substituted by halo. More preferably, $R^3$ is $C_{1-4}$alkyl or $C_{3-6}$cycloalkyl. Most preferably, $R^3$ is $C_{3-4}$alkyl or $C_{5-6}$cycloalkyl. Especially, $R^3$ is cyclohexyl.

Preferably, $R^4$ is hydrogen or $C_{1-6}$alkyl. More preferably, $R^4$ is hydrogen or $C_{1-4}$alkyl. Most preferably, $R^4$ is hydrogen or $C_{1-2}$alkyl. Especially, $R^4$ is hydrogen.

Preferably, $R^5$ is hydrogen, halo, hydroxy, $C_{1-6}$alkyl, $C_{1-6}$alkoxy, $C_{3-8}$cycloalkyl, aryl or heteroaryl. More preferably, $R^5$ is hydrogen, $C_{1-6}$alkyl, $C_{3-8}$cycloalkyl or aryl. Most preferably, $R^5$ is hydrogen, $C_{1-4}$alkyl, $C_{3-6}$cycloalkyl or phenyl. Especially, $R^5$ is hydrogen, $C_{1-2}$alkyl, $C_{5-6}$cycloalkyl or phenyl. More especially, $R^5$ is phenyl.

Preferably, W is halo, $OR^6$, $C_{1-6}$alkyl, $CF_3$, $CO_2R^6$, $CON(R^6)_2$, $COR^6$ or $NR^6C(O)R^6$, where $R^6$ is as hereinbefore defined. More preferably, W is fluoro, chloro, $OC_{1-6}$alkyl, $CF_3$, $CO_2C_{1-6}$alkyl, or $CONHC_{1-6}$alkyl. Most preferably, W is fluoro, chloro, $OC_{1-4}$alkyl or $CF_3$. Especially, W is $OC_{1-2}$alkyl. More especially, W is methoxy.

Preferably, M is $C_{3-12}$alkylene or $C_{3-12}$alkenylene, optionally substituted by halo or $C_{1-6}$alkyl. More preferably, M is $C_{4-8}$alkylene or $C_{4-8}$alkenylene, optionally substituted by fluoro or $C_{1-4}$alkyl. Most preferably, M is $C_{6-7}$alkylene or $C_{6-7}$alkenylene, optionally substituted by $C_{1-2}$alkyl. Especially, M is hexylene, heptylene,

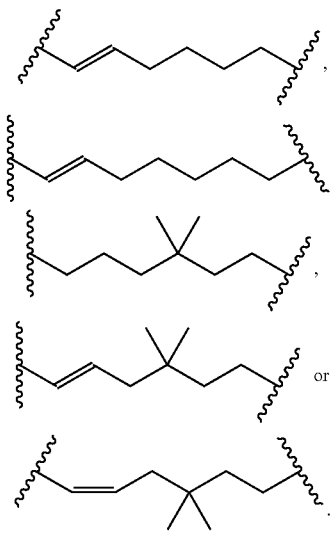

When any variable occurs more than one time in formula (I) or in any substituent, its definition on each occurrence is independent of its definition at every other occurrence.

As used herein, the term "alkyl" as a group or part of a group refers to any linear or branched chain alkyl group having a number of carbon atoms in the specified range. Thus, for example, "$C_{1-6}$alkyl" refers to all of the hexyl alkyl and pentyl alkyl isomers as well as n-, iso-, sec- and t-butyl, n- and iso-propyl, ethyl and methyl. As another example, "$C_{1-4}$alkyl" refers to n-, iso-, sec- and t-butyl, n- and iso-propyl, ethyl and methyl.

The term "alkoxy" represents any linear or branched chain alkyl group having a number of carbon atoms in the specified range and attached through an oxygen bridge. Examples of suitable alkoxy groups include methoxy, ethoxy, n-propoxy, i-propoxy, n-butoxy, s-butoxy, i-butoxy and t-butoxy.

The term "alkenyl" as a group or part of a group refers to any linear or branched chain alkyl group containing at least one double bond, which may occur at any point along the chain, and having a number of carbon atoms in the specified range. E- and Z- forms are both included, where applicable. Examples of suitable alkenyl groups include vinyl, allyl, butenyl and pentenyl.

The term "cycloalkyl" refers to any cyclic alkyl ring having a number of carbon atoms in the specified range. Examples of suitable cycloalkyl groups include cyclopropyl, cyclobutyl, cyclopentyl and cyclohexyl.

The terms "alkylene" and "alkenylene" as a group or part of a group refer to the groups "alkyl" and "alkenyl" respectively, when they are divalent, i.e. attached at two atoms.

The term "halogen" or "halo" means fluorine, chlorine, bromine and iodine (alternatively referred to as fluoro, chloro, bromo and iodo, respectively).

The term "aryl" as a group or part of a group means a carbocyclic aromatic ring. Examples of suitable aryl groups include phenyl and naphthyl.

The term "Het" as a group or part of a group means a 5- to 7-membered saturated or unsaturated non-aromatic ring having 1 to 4 heteroatoms selected from N, O and S.

The term "heteroaryl" as a group or part of a group means a 5- to 10-membered heteroaromatic ring system containing 1 to 4 heteroatoms selected from N, O and S. Examples of such groups include pyrrolyl, furanyl, thienyl, pyridyl, pyrazolyl, imidazolyl, oxazolyl, isoxazolyl, thiazolyl, isothiazolyl, pyrazinyl, pyrimidinyl, pyridazinyl, triazolyl, oxadiazolyl, thiadiazolyl, triazinyl, tetrazolyl, indolyl, benzothienyl, benzimidazolyl, benzofuryl, quinolyl and isoquinolyl.

Unless expressly stated to the contrary, all ranges cited herein are inclusive. For example, a heteroaryl ring described as containing from "1 to 3 heteroatoms" means the ring can contain 1, 2, or 3 heteroatoms.

Where a compound or group is described as "optionally substituted" one or more substituents may be present. Furthermore, optional substituents may be attached to the compounds or groups which they substitute in a variety of ways, either directly or through a connecting group of which the following are examples: amine, amide, ester, ether, thioether, sulfonamide, sulfamide, sulfoxide, urea, thiourea and urethane. As appropriate an optional substituent may itself be substituted by another substituent, the latter being connected directly to the former or through a connecting group such as those exemplified above.

Specific compounds within the scope of this invention include those named in the Examples and Table hereinbelow and their pharmaceutically acceptable salts.

For use in medicine, the salts of the compounds of formula (I) will be non-toxic pharmaceutically acceptable salts. Other salts may, however, be useful in the preparation of the compounds according to the invention or of their non-toxic pharmaceutically acceptable salts. Suitable pharmaceutically acceptable salts of the compounds of this invention include acid addition salts which may, for example, be formed by mixing a solution of the compound according to the invention with a solution of a pharmaceutically acceptable acid such as hydrochloric acid, fumaric acid, p-toluenesulfonic acid, maleic acid, succinic acid, acetic acid, citric acid, tartaric acid, carbonic acid, phosphoric acid or sulfuric acid. Salts of amine groups may also comprise quaternary ammonium salts in which the amino nitrogen atom carries a suitable organic group such as an alkyl, alkenyl, alkynyl or aralkyl moiety. Furthermore, where the compounds of the invention carry an acidic moiety, suitable pharmaceutically acceptable salts thereof may include metal salts such as alkali metal salts, e.g. sodium or potassium salts; and alkaline earth metal salts, e.g. calcium or magnesium salts.

The salts may be formed by conventional means, such as by reacting the free base form of the product with one or more equivalents of the appropriate acid in a solvent or medium in which the salt is insoluble, or in a solvent such as water which is removed in vacuo or by freeze drying or by exchanging the anions of an existing salt for another anion on a suitable ion exchange resin.

The present invention includes within its scope prodrugs of the compounds of formula (I) above. In general, such prodrugs will be functional derivatives of the compounds of formula (I) which are readily convertible in vivo into the required compound of formula (I). Conventional procedures for the selection and preparation of suitable prodrug derivatives are described, for example, in "Design of Prodrugs", ed. H. Bundgaard, Elsevier, 1985.

A prodrug may be a pharmacologically inactive derivative of a biologically active substance (the "parent drug" or "parent molecule") that requires transformation within the body in order to release the active drug, and that has improved delivery properties over the parent drug molecule. The transformation in vivo may be, for example, as the result of some metabolic process, such as chemical or enzymatic hydrolysis of a carboxylic, phosphoric or sulfate ester, or reduction or oxidation of a susceptible functionality.

The present invention includes within its scope solvates of the compounds of formula (I) and salts thereof, for example, hydrates.

The present invention also includes within its scope any enantiomers, diastereomers, geometric isomers and tautomers of the compounds of formula (I). It is to be understood that all such isomers and mixtures thereof are encompassed within the scope of the invention.

The preferred compounds of the present invention will have the stereochemistry as shown in formula (Ie):

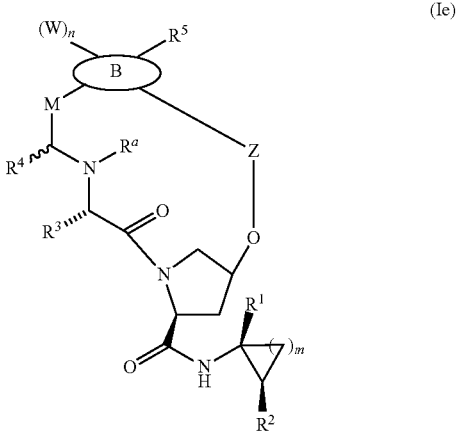

(Ie)

The present invention further provides a compound of formula (I) or a pharmaceutically acceptable salt thereof for use in therapy.

In another aspect, the invention provides the use of a compound of formula (I) as defined above, or a pharmaceutically acceptable salt thereof, for the manufacture of a medicament for treatment or prevention of infection by hepatitis C virus in a human or animal.

A further aspect of the invention provides a pharmaceutical composition comprising a compound of formula (I) as defined above, or a pharmaceutically acceptable salt thereof, in association with a pharmaceutically acceptable carrier. The composition may be in any suitable form, depending on the intended method of administration. It may for example be in the form of a tablet, capsule or liquid for oral administration, or of a solution or suspension for administration parenterally.

The pharmaceutical compositions optionally also include one or more other agents for the treatment of viral infections such as an antiviral agent, or an immunomodulatory agent such as α-, β- or γ-interferon.

In a further aspect, the invention provides a method of inhibiting hepatitis C virus protease and/or of treating or preventing an illness due to hepatitis C virus, the method involving administering to a human or animal (preferably mammalian) subject suffering from the condition a therapeutically or prophylactically effective amount of the pharmaceutical composition described above or of a compound of formula (I) as defined above, or a pharmaceutically acceptable salt thereof. "Effective amount" means an amount sufficient to cause a benefit to the subject or at least to cause a change in the subject's condition.

The term "subject" (alternatively referred to herein as "patient") as used herein refers to an animal, preferably a mammal, most preferably a human, who has been the object of treatment, observation or experiment.

The dosage rate at which the compound is administered will depend on a variety of factors including the activity of the specific compound employed, the metabolic stability and length of action of that compound, the age of the patient, body weight, general health, sex, diet, mode and time of administration, rate of excretion, drug combination, the severity of the particular condition and the host undergoing therapy. Suitable dosage levels may be of the order of 0.02 to 5 or 10 g per day, with oral dosages two to five times higher. For instance, administration of from 10 to 50 mg of the compound per kg of body weight from one to three times per day may be in order. Appropriate values are selectable by routine testing. The compound may be administered alone or in combination with other treatments, either simultaneously or sequentially. For instance, it may be administered in combination with effective amounts of antiviral agents, immunomodulators, antiinfectives or vaccines known to those of ordinary skill in the art. It may be administered by any suitable route, including orally, intravenously, cutaneously and subcutaneously. It may be administered directly to a suitable site or in a manner in which it targets a particular site, such as a certain type of cell. Suitable targeting methods are already known.

An additional aspect of the invention provides a method of preparation of a pharmaceutical composition, involving admixing at least one compound of formula (I) as defined above, or a pharmaceutically acceptable salt thereof, with one or more pharmaceutically acceptable adjuvants, diluents or carriers and/or with one or more other therapeutically or prophylactically active agents.

As noted above, the present invention also relates to a method of inhibiting HCV NS3 protease, inhibiting HCV replication, or preventing or treating HCV infection with a compound of the present invention in combination with one or more therapeutic agents and a pharmaceutical composition comprising a compound of the present invention and one or more therapeutic agents selected from the group consisting of a HCV antiviral agent, an immunomodulator, and an antiinfective agent. Such therapeutic agents active against HCV include ribavirin, levovirin, viramidine, thymosin alpha-1, interferon-β, interferon-α, pegylated interferon-α (peginterferon-α), a combination of interferon-α and ribavirin, a combination of peginterferon-α and ribavirin, a combination of interferon-α and levovirin, and a combination of peginterferon-α and levovirin. Interferon-α includes recombinant interferon-α2a (such as ROFERON interferon available from Hoffmann-LaRoche, Nutley, N.J.), pegylated interferon-α2a (PEGASYS™), interferon-α2b (such as INTRON-A interferon available from Schering Corp., Kenilworth, N.J.), pegylated interferon-α2b (PegIntron™), a recombinant consensus interferon (such as interferon alphacon-1), and a purified interferon-α product. Amgen's recombinant consensus interferon has the brand name INFERGEN®. LEVOVIRIN is the L-enantiomer of ribavirin which has shown immunomodulatory activity similar to ribavirin. Viramidine represents an analog of ribavirin disclosed in WO 01/60379 (ICN Pharmaceuticals). In accordance with the method of the present invention, the individual components of the combination can be administered separately at different times during the course of therapy or concurrently in divided or single combination forms.

For the treatment of HCV infection, the compounds of the present invention may also be administered in combination with an agent that is an inhibitor of HCV NS3 serine protease. HCV NS3 protease inhibitors are disclosed in WO 98/22496, WO 98/46630, WO 99/07733, WO 99/07734, WO 99/38888, WO 99/50230, WO 99/64442, WO 00/09543, WO 00/59929, GB-2337262, WO 02/48116, WO 02/48172, and U.S. Pat. No. 6,323,180.

Ribavirin, levovirin, and viramidine may exert their anti-HCV effects by modulating intracellular pools of guanine nucleotides via inhibition of the intracellular enzyme inosine monophosphate dehydrogenase (IMPDH). Thus, inhibition of IMPDH represents another useful target for the discovery of inhibitors of HCV replication. Therefore, the compounds of the present invention may also be administered in combination with an inhibitor of IMPDH, such as VX-497, disclosed in WO 97/41211 and WO 01/00622 (Vertex); another IMPDH inhibitor, such as that disclosed in WO 00/25780 (Bristol-Myers Squibb); or mycophenolate mofetil [see A. C. Allison and E. M. Eugui, *Agents Action,* 44 (Suppl.): 165 (1993)].

For the treatment of HCV infection, the compounds of the present invention may also be administered in combination with the antiviral agent amantadine (1-aminoadamantane) [see J. Kirschbaum, *Anal. Profiles Drug Subs.* 12: 1-36 (1983)].

The compounds of the present invention may also be combined for the treatment of HCV infection with antiviral 2'-C-branched ribonucleosides disclosed in R. E. Harry-O'kuru, et al., *J. Org. Chem.* 62: 1754-1759 (1997); M. S. Wolfe, et al., *Tetrahedron Lett.,* 36: 7611-7614 (1995); U.S. Pat. No. 3,480,613; WO 01/90121; WO 01/92282; WO 02/32920; WO 04/002999; WO 04/003000; and WO 04/002422. Such 2'-C-branched ribonucleosides include 2'-C-methyl-cytidine, 2'-C-methyl-uridine, 2'-C-methyl-adenosine, 2'-C-methyl-guanosine, and 9-(2-C-methyl-β-D-ribofuranosyl)-2,6-diaminopurine, and the corresponding amino acid ester of the ribose C-2', C-3', and C-5' hydroxyls and the corresponding optionally substituted cyclic 1,3-propanediol esters of the 5'-phosphate derivatives.

The compounds of the present invention may also be combined for the treatment of HCV infection with other nucleosides having anti-HCV properties, such as those disclosed in WO 02/51425 (Mitsubishi Pharma Corp.); WO 01/79246, WO 02/32920 and WO 02/48165 (Pharmasset, Ltd.); WO 01/68663 (ICN Pharmaceuticals); WO 99/43691; WO 02/18404 (Hoffmann-LaRoche); U.S. 2002/0019363; WO 02/100415; WO 03/026589; WO 03/026675; WO 03/093290; US 2003/0236216; US 2004/0006007; WO 04/011478; WO 04/013300; US 2004/0063658; and WO 04/028481.

For the treatment of HCV infection, the compounds of the present invention may also be administered in combination with an agent that is an inhibitor of HCV NS5B polymerase. Such HCV NS5B polymerase inhibitors that may be used as combination therapy include those disclosed in WO 02/057287, U.S. Pat. No. 6,777,395, WO 02/057425, US 2004/0067901, WO 03/068244, WO 2004/000858, WO 04/003138 and WO 2004/007512. Other such HCV polymerase inhibitors include valopicitabine (NM-283; Idenix) and 2'-F-2'-beta-methylcytidine (see also WO 2005/003147, assigned to Pharmasset, Ltd.).

The compounds of the present invention may also be combined for the treatment of HCV infection with non-nucleoside inhibitors of HCV polymerase such as those disclosed in WO 01/77091 (Tularik, Inc.); WO 01/47883 (Japan Tobacco, Inc.); WO 02/04425 (Boehringer Ingelheim); WO 02/06246, WO 03/062211, WO 2004/087714, WO 2004/110442, WO 2005/034941, WO 2005/023819, WO2006/029912, WO 2006/008556, WO 2006/027628, GB2430621, WO2006/046030, WO2006/046039, WO2006/119975, WO2007/028789 and WO2007/029029 (all Istituto di Ricerche di Biologia Molecolare P. Angeletti S. p. A.); WO 02/20497; WO 2005/016927 (in particular JTK003), and WO 2005/080399 (Japan Tobacco, Inc.); WO 2006/020082 (Bristol-Myers Squibb Company); and HCV-796 (Viropharma Inc.).

The present invention also provides a process for the preparation of compounds of formula (I).

According to a general process (a), compounds of formula (I) may be prepared by the coupling of the ester of formula (II) with the amine of formula (III):

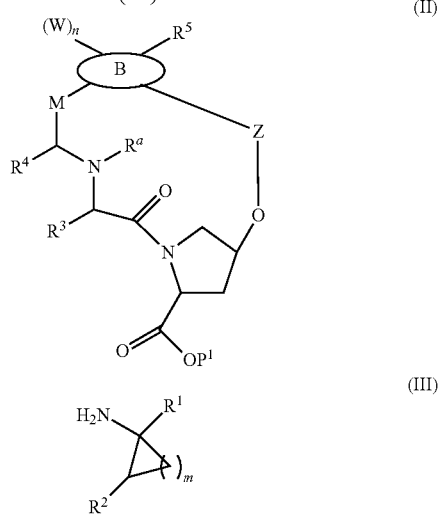

where m, n, $R^1$, $R^2$, $R^3$, $R^4$, $R^5$, $R^a$, M, W, Z and ring B are as defined in relation to formula (I) and $P^1$ is $C_{1-6}$alkyl, such as methyl. The ester (II) is first hydrolysed under standard conditions (e.g. in the presence of a base, such as lithium hydroxide, in a solvent, such as THF/water, MeOH/water or dioxane/water) to give the free acid. The coupling reaction is then conveniently carried out in the presence of a coupling reagent, such as TBTU or HATU, and a base, such as diisopropylethylamine or triethylamine, in a solvent. Suitable solvents include DMF and dichloromethane. Optionally, a dehydrating agent, such as DMAP, may also be used.

The compound of formula (II) where M has 4 or more carbon atoms in the tether and one or more double bonds may be prepared by the internal ring closure of the diene of formula (IV):

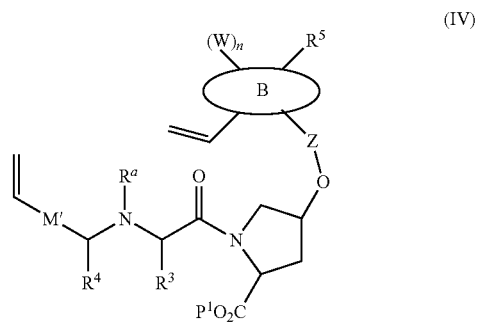

where n, $R^3$, $R^4$, $R^5$, $R^a$, W, Z and ring B are as defined in relation to formula (I), $P^1$ is as defined in relation to formula (II) and M' is a suitable precursor moiety of group M in formula (II) which can be converted into the corresponding moiety of M during the ring closure or after it using methods described in the accompanying Schemes and Examples or known to the person skilled in the art. The reaction is conveniently carried out in the presence of a metathesis catalyst, such as Zhan catalyst [dichloro(5-chloro-2-isopropoxy benzylidene)(1,3-dimethylimidazolidin-2-ylidene)ruthenium], preferably at raised temperature or under microwave irradiation, in a suitable solvent such as dichloromethane or 1,2-dichloroethane. The resultant ring double bond may be hydrogenated to give a further compound of formula (II). The hydrogenation is preferably carried out in the presence of a suitable catalyst, such as palladium on carbon, in a suitable solvent, such as methanol or methanol/ethyl acetate mixture.

Compounds of formulae (II), (III) and (IV) are either well known in the art or may be prepared by conventional methodology well known to one of ordinary skill in the art using, for instance, procedures described in the accompanying Schemes and Examples, or by alternative procedures which will be readily apparent.

Further details of suitable procedures will be found in the accompanying Schemes and Examples. For instance compounds of formula (I) can be converted into other compounds of formula (I) using synthetic methodology well known in the art.

Thus, for instance, the compound of formula (I) where M is unsaturated may be converted into the compound of formula (I) where M is saturated by hydrogenation, preferably in the presence of a suitable catalyst, such as palladium on carbon, in a suitable solvent, such as methanol/ethyl acetate mixture.

Furthermore, the compound of formula (I) where $R^a$ is $C_{1-4}$alkyl may be prepared from the compound of formula (I) where $R^a$ is hydrogen by alkylation. The reaction may be carried out in the presence of a mild base, such as sodium cyanoborohydride, and a catalyst, such as zinc (II) chloride, in a suitable solvent, such as methanol. The alkyl source is formaldehyde or $CH_3(CH_2)_{0-2}CHO$.

During any of the described synthetic sequences, it may be necessary and/or desirable to protect sensitive or reactive groups on any of the molecules concerned. This may be achieved by means of conventional protecting groups such as those described in Protective Groups in Organic Chemistry, ed. J. F. W. McOmie, Plenum Press, 1973; and T. W. Greene & P. G. M. Wuts, Protective Groups in Organic Synthesis, John Wiley & Sons, $3^{rd}$ ed., 1999. The protecting groups may be removed at a convenient subsequent stage using methods known from the art.

The compounds of the present inventions are useful in the inhibition of HCV protease (e.g., HCV NS3 protease) and the prevention or treatment of infection by HCV. For example, the compounds of this invention are useful in treating infection by HCV after suspected past exposure to HCV by such means as blood transfusion, exchange of body fluids, bites, accidental needle stick, or exposure to patient blood during surgery.

The compounds of this invention are useful in the preparation and execution of screening assays for antiviral compounds. For example, the compounds of this invention are useful for isolating enzyme mutants, which are excellent screening tools for more powerful antiviral compounds. Furthermore, the compounds of this invention are useful in establishing or determining the binding site of other antivirals to HCV protease, e.g., by competitive inhibition. Thus the compounds of this invention are commercial products to be sold for these purposes.

The HCV NS3 protease inhibitory activity of the present compounds may be tested using assays known in the art. One such assay is HCV NS3 protease time-resolved fluorescence (TRF) assay as described as follows:

HCV NS3 Protease Time-Resolved Fluorescence (TRF) Assay

The NS3 protease TRF assay was performed in a final volume of 100 µl in assay buffer containing 50 mM HEPES, pH 7.5, 150 mM NaCl, 15% glycerol, 0.15% Triton X-100, 10 mM DTT, and 0.1% PEG 8000. The NS3 protease was pre-incubated with various concentrations of inhibitors for 10-30 minutes. The peptide substrate for the assay is Ac—C(Eu)-DDMEE-Abu-[COO]-XSAK(QSY7)-NH2 (SEQ ID No. 1), where Eu is an europium-labeled group, Abu is 1-aminobutanoic acid which connects an ester linkage with 2-hydroxy propanoic acid (X). Hydrolysis of the peptide by NS3 protease activity causes in separation of the fluorophore from the quencher, resulting in an increase in fluorescence. Activity of the protease was initiated by adding the TRF peptide substrate (final concentration 50-100 nM). The reaction was quenched after 1 hour at room temperature with 100 µl of 500 mM MES, pH 5.5. Product fluorescence was detected using either a Victor V2 or Fusion fluorimeter (Perkin Elmer Life and Analytical Sciences) with excitation at 340 nm and emission at 615 nm with 50-400 µs delay. Testing concentrations of different enzyme forms was selected with a signal to background ratio of 10-30. The inhibition constants were derived using a four-parameter fit.

Other examples of such assays are described in e.g., International patent publication WO2005/046712. s useful as HCV NS3 protease inhibitors would have a Ki less than 50 µM, more preferably less than 10 µM, most preferably less than 1 µM, especially less than 100 mM, and more especially less than 50 nM.

The following schemes and examples serve to illustrate the invention and its practice.

$^1$H NMR spectra were recorded on Bruker AM series spectrometers operating at (reported) frequencies between 300 and 600 MHz. Chemical shifts (☐) for signals corresponding to non-exchangeable protons (and exchangeable protons where visible) are recorded in parts per million (ppm) relative to tetramethylsilane and are measured using the residual solvent peak as reference. Signals are tabulated in the order: multiplicity (s, singlet; d, doublet; t, triplet; q, quartet; m, multiplet; b, broad, and combinations thereof); coupling constant(s) in Hertz (Hz); number of protons. Mass spectral (MS) data were obtained on a Perkin Elmer API 100, or Waters Micromass ZQ, operating in negative (ES$^-$) or positive (ES$^+$) ionization mode and results are reported as the ratio of mass over charge (m/z). Preparative scale HPLC separations were carried out on a WatersMicromass System incorporating a 2525 pump module, a Micromass ZMD detector and a 2767 collection module, under Fraction Linx software or on a Shimadzu preparative system.

The following abbreviations are used in the examples, the schemes and the tables:
AcOH: acetic acid; dioxan(e): 1,4-dioxane; DIPEA or $^i$Pr$_2$NEt: diisopropylethylamine; DCE: 1,2-dichloroethane; DCM: dichloromethane; DMAP: 4-dimethylaminopyridine; DMF: N,N-dimethylformamide; DMSO: dimethylsulfoxide; EDC: 1-(3-dimethylaminopropyl)-3-ethylcarbodiimide; Et$_2$O: diethyl ether; EtOAc: ethyl acetate; eq.: equivalent(s); h: hour(s); HATU: O-(7-azabenzotriazol-1-yl)-N,N,N',N'-tetramethyluronium hexafluorophosphate; MeCN: acetonitrile; MeOH: methanol; min: minute(s); MS: mass spectrum; MTBE: tert Butyl methyl ether; PCC: pyridinium chlorochromate; PE: petroleum ether 30/60; quant.: quantitative; RP-HPLC: reversed phase high-performance liquid chromatography; RP-MS-HPLC: mass-guided reversed phase high-pressure liquid chromatography; RT: room temperature; sat. aq.: saturated aqueous; TBTU: O-benzotriazol-1-yl-N,N,N',N'-tetramethyluronium tetrafluoroborate; TEA: triethylamine; THF: tetrahydrofuran.

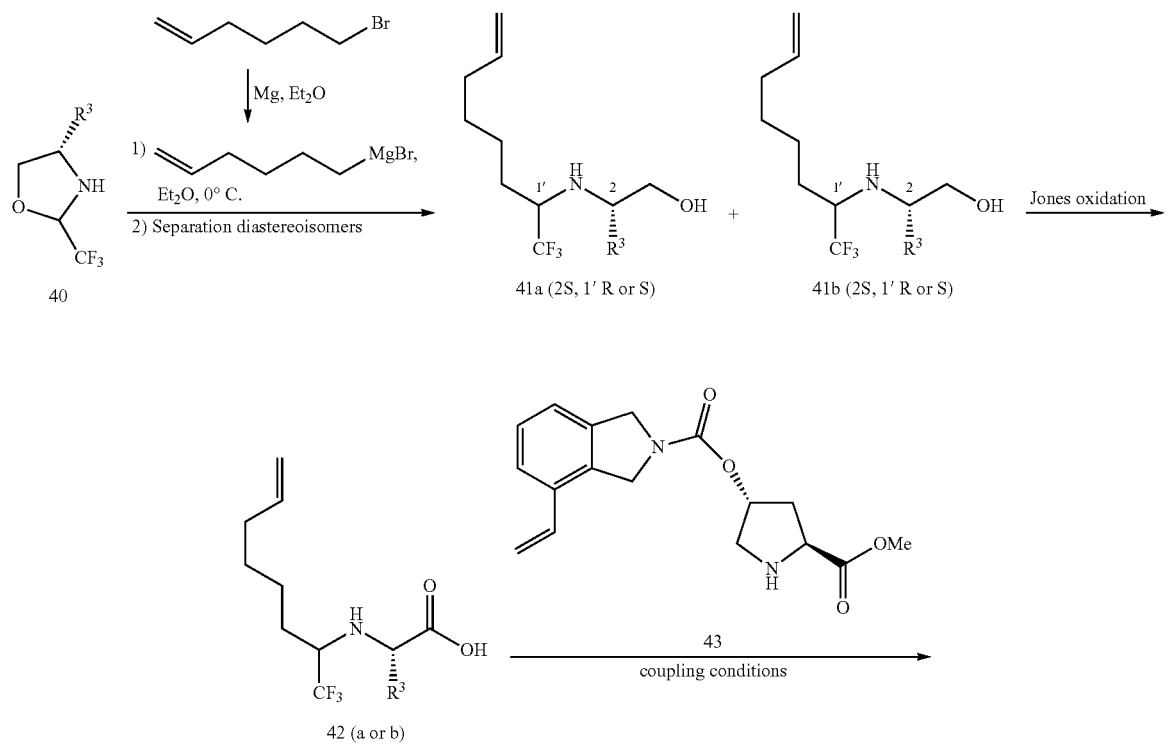

Scheme 1

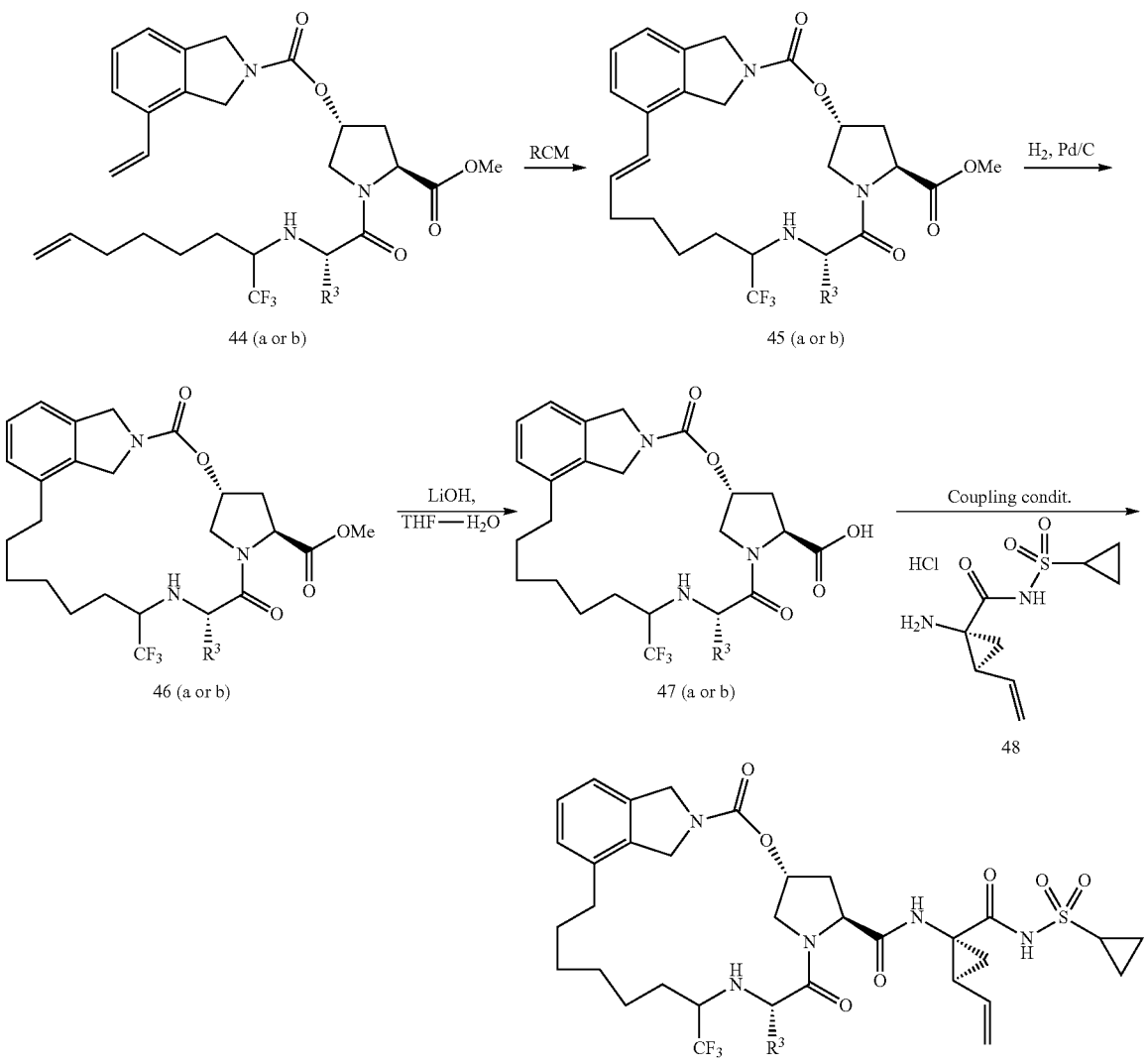

Compound 1: (5R,7S,10S,12R or S)-N-((1R,2S)-1-{[(cyclopropylsulfonyl)amino]carbonyl}-2-vinyl-cyclopropyl)-10-isopropyl-3,9-dioxo-12-(trifluoromethyl)-6,7,9,10,11,12,13,14,15,16,17,18-dodecahydro-1H,5H-2, 22:5,8-dimethano-4,2,8,11-benzoxatriazacycloicosine-7-carboxamide Step 1: (4S)-4-isopropyl-2-(trifluoromethyl)-1,3-oxazolidine 40 (R³=isopropyl)

The oxazolidine 40 was obtained as a 7:3 mixture of diastereoisomers prepared as described in Organic Letters 2004, 641.

Step 2: (2S)-3-methyl-2-{[(1R or S)-1-(trifluoromethyl)hept-6-en-1-yl]amino}butan-1-ol 41a (R³=isopropyl)

A small amount of a solution (3M) of 6-bromohex-1-ene in dry Et₂O was added dropwise to magnesium turnings (1 eq.). A small crystal of iodine was added followed by the remainder of the bromide solution. The reaction mixture was cooled to −78° C. and (4S)-4-isopropyl-2-(trifluoromethyl)-1,3-oxazolidine 40 (1 eq.) dissolved in Et₂O (3M) was added dropwise. The reaction mixture was stirred at 0° C. for 1 h and then quenched with aqueous HCl (1N). Aqueous NaOH (1N) was added until pH=7. The two layers were separated and the aqueous phase was diluted with brine and extracted with CH₂Cl₂. The organic layers were joined, washed with brine, dried over Na₂SO₄, filtered and concentrated in vacuo. The residue was purified by flash chromatography on silica gel (EtOAc/PE gradient from 5:95 to 20:80) to afford the title compound as a mixture of two diastereoisomers (50%) that were separated by RP-HPLC (stationary phase: column WATERS SYMMETRY prep. C18, 7 μm, 19×300 mm, mobile phase: MeCN/H₂O containing 0.1% TFA). Fractions containing the desired compounds as pure diastereoisomers were combined and freeze dried to afford 41a (second eluting) and 41b (first eluting) (67%, 41a: 41b=1: 0.14).

41a) ¹H NMR (300 MHz, CDCl₃, 300 K) δ 5.75 (ddt, J 17.0, 10.2, 6.7, 1H), 5.47-5.17 (bs, 1H), 5.06-4.90 (m, 2H), 3.96-3.70 (m, 3H), 3.24-3.09 (m, 1H) 2.13-1.74 (m, 5H), 1.60-1.34 (m, 4H), 1.07 (d, J 6.9, 3H), 1.01 (d, J 6.9, 3H). MS (ES⁺) m/z 268 (M+H)⁻.

Step 3: (2S)-3-methyl-2-1-[(1R³ or S)-1-(trifluoromethyl)hept-6-en-1-yl]amino butanoic acid 42a (R³=isopropyl)

To a solution (0.13 M) of (2S)-3-methyl-2-{[1-(trifluoromethyl)hept-6-en-1-yl]amino}butan-1-ol 41a in acetone cooled to 0° C., Jones reagent (8N) (5 eq.) was added. The reaction mixture was stirred at 0° C. for 15 min at RT overnight then was diluted with water and stirred at RT for 20 min. Aqueous NaOH (1N) was added to reach pH=5 and the mixture was extracted with CH₂Cl₂. The organic layer was dried over Na₂SO₄, filtered and concentrated in vacuo to afford the crude product, which was used in the following step without further purification. MS (ES⁺) m/z 282 (M+H)⁺.

Step 4: methyl N-[(1R³ or S)-1-(trifluoromethyl)hept-6-en-1-yl]-L-valyl-(4R)-4-1-{[(4-vinyl-1,3-dihydro-2H-isoindol-2-yl)carbonyl]oxy}-L-prolinate 44a (R³=isopropyl)

To a stirred mixture of (2S)-3-methyl-2-{[(1R or S)-1-(trifluoromethyl)hept-6-en-1-yl]amino}butanoic acid 42a in CH₂Cl₂ (0.09M) were added iPr₂EtN (2.4 eq.), TBTU (1.2 eq.) and after 5 min (2S,4R)-2-(methoxycarbonyl)-4-{[(4-vinyl-1,3-dihydro-2H-isoindol-2-yl)carbonyl]oxy}pyrrolidinium chloride 43 (1 eq.). The mixture was stirred at RT overnight. Aqueous HCl (1N) was added, the organic layer was separated and washed with sat. aq. NaHCO₃ and brine, dried over Na₂SO₄ and filtered. Evaporation under reduced pressure afforded a residue, which was purified by flash chromatography on silica gel (EtOAc/PE gradient from 5:95 to 15:85) to afford compound 44a as a white foam (24% after two steps). MS (ES⁺) m/z 580 (M+H)⁺.

Step 5: methyl (5R,7S,10S,12R or S, 17E)-10-isopropyl-3,9-dioxo-12-(trifluoromethyl)-6,7,9,10,11,12,13,14,15,16-dec-hydro-1H,5H-2, 22:5,8-dimethano-4,2,8,11-benzoxatriazacycloicosine-7-carboxylate 45a (R³=isopropyl)

Zhan catalyst I (0.15 eq.) was added to methyl N-[1-(trifluoromethyl)hept-6-en-1-yl]-L-valyl-(4R)-4-{[(4-vinyl-1,3-dihydro-2H-isoindol-2-yl)carbonyl]oxy}-L-prolinate 44a in DCE (0.016 M) and the mixture was refluxed for 45 min. Volatiles were evaporated under reduced pressure affording a residue, which was used in the following step without further purification. MS (ES⁺) m/z 552 (M+H)⁺.

Step 6: methyl (5R,7S,10S,12R or S)-10-isopropyl-3,9-dioxo-12-(trifluoromethyl)-6,7,9,10,11,12,13,14,15,16,17,18-dodecahydro-1H,5H-2, 22:5,8-dimethano-4,2,8,11-benzoxatriazacycloicosine-7-carboxylate 46a (R³=isopropyl)

Palladium 10% on carbon (20% w/w) and methyl (5R,7S,10S,12R³ or S,17E)-10-isopropyl-3,9-dioxo-12-(trifluoromethyl)-6,7,9,10,11,12,13,14,15,16-decahydro-1H,5H-2, 22:5,8-dimethano-4,2,8,11-benzoxatriazacycloicosine-7-carboxylate 45a in methanol (0.035M) were stirred under a hydrogen atmosphere overnight. Solids were filtered over CELITE and the resulting solution was evaporated under reduced pressure. The residue was purified by flash chromatography on silica gel (EtOAc/PE gradient from 1:9 to 3:7) to afford compound 46a as a white foam (70% over two steps). MS (ES⁺) m/z 554 (M+H)⁺.

Step 7: (5R,7S, 10S, 12R or S)-10-isopropyl-3,9-dioxo-12-(trifluoromethyl)-6,7,9,10,11,12,13,14,15,16,17,18-dodecahydro-1H,5H-2, 22:5,8-dimethano-4,2,8,1-benzoxatriazacycloicosine-7-carboxylic acid 47a (R³=isopropyl)

Lithium hydroxide (3 eq.) was added to a stirred mixture of methyl (5R,7S,10S,12R or S)-10-isopropyl-3,9-dioxo-12-(trifluoromethyl)-6,7,9,10,11,12,13,14,15,16,17,18-dodecahydro-1H,5H-2, 22:5,8-dimethano-4,2,8,11-benzoxatriazacycloicosine-7-carboxylate 46a in THF and water (2/1 v/v, 0.01 M) and the mixture was stirred at RT overnight. Aqueous HCl (1N) was added to reach pH=6 and the mixture extracted with EtOAc. The organic layer was separated, dried over Na₂SO₄, filtered and concentrated to obtain the crude product 47a which was used in the following step without further purification. MS (ES⁺) m/z 540 (M+H)⁺.

Step 8: (5R,7S,10S,12R or S)-N-((1R,2S)-1-{[(cyclopropylsulfonyl)amino]carbonyl}-2-vinylcyclopropyl)-10-isopropyl-3,9-dioxo-12-(trifluoromethyl)-6,7,9,10,11,12,13,14,15,16,17,18-dodecahydro-1H,5H-2, 22:5,8-dimethano-4,2,8,11-benzoxatriazacycloicosine-7-carboxamide 1

To a stirred mixture of (5R,7S, 10S)-10-isopropyl-3,9-dioxo-12-(trifluoromethyl)-6,7,9,10,11,12,13,14,15,16,17,18-dodecahydro-1H,5H-2, 22:5,8-dimethano-4,2,8,11-benzoxatriazacycloicosine-7-carboxylic acid 47a in CH₂Cl₂ (5mM) were added i-Pr₂EtN (2.4 eq), TBTU (1.2 eq.) and after 5 min (1R,2S)-1-{[(cyclopropylsulfonyl)amino]carbonyl}-2-vinylcyclopropanaminium chloride 48 (prepared as described in WO 03/099274) (1.2 eq.). The mixture was stirred at RT overnight. The reaction mixture was extracted with aqueous HCl (1N), sat. aq. NaHCO₃ and brine, dried over Na₂SO₄ and filtered. Evaporation under reduced pressure afforded a residue, which was dissolved in DMSO and purified by RP-HPLC (stationary phase: column SYMMETRY C18, 7 μm, 19×300 mm. Mobile phase: MeCN/H₂O buffered with 0.1% TFA). Fractions containing the pure compound were combined and freeze dried to afford compound I as a white powder (34%). ¹H NMR (600 MHz, DMSO-d₆, 300 K) δ 10.57 (s, 1H), 9.22 (s, 1H), 7.24 (t, J 7.5, 1H), 7.18 (d, J 7.5, 1H), 7.11 (d, J 7.5, 1H), 5.68 (ddd, J 17.2, 10.0, 9.6, 1H), 5.42 (bt, 1H), 5.28 (dd, J 17.2, 1.5, 1H), 5.12 (dd, J 10.4, 1.7, 1H), 4.67-4.56 (m, 4H), 4.40 (dd, J 11.0, 6.5, 1H), 3.96 (d, J 10.3, 1H), 3.76 (dd, J 11.7, 3.1, 1H), 3.31 (d, J 6.3, 1H), 2.92-2.86 (m, 1H), 2.92-2.30 (m, 1H), 2.55-2.50 (partially obscured by residual DMSO, 1H), 2.47-2.40 (m, 1H), 2.22 (dd, J 13.8, 6.4, 1H), 2.16 (q, J 8.8, 1H), 2.09-2.02 (m, 1H), 1.79-1.71 (m, 2H), 1.57-1.46 (m, 3H), 1.44-1.18 (m, 8H), 1.13-1.07 (m, 1H), 1.06-0.98 (m, 3H), 0.91 (d, J 6.6, 3H), 0.83 (d, J 6.6, 3H). ¹³C NMR (600 MHz, DMSO-d₆, 300 K) δ 174.08, 172.16, 169.17, 152.92, 137.09, 136.23, 135.00, 133.37, 127.93, 127.57, 126.04, 120.32, 117.87, 73.50, 64.83, 59.03, 58.87, 53.23, 52.12, 50.67, 40.79, 34.59, 33.81, 31.42, 31.17, 30.74, 28.90, 28.48, 26.43, 26.02, 23.47, 22.76, 19.09, 17.93, 5.73, 5.36. MS (ES⁺) m/z 752 (M+H)⁺.

Scheme 2

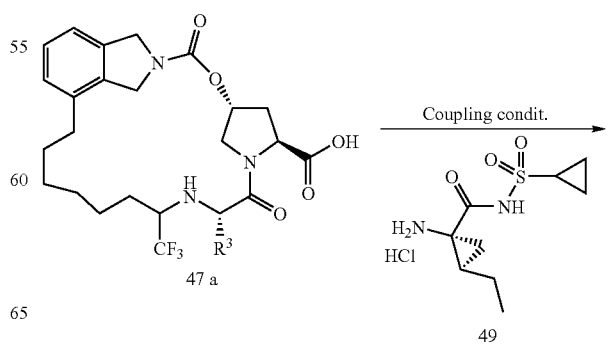

23
-continued
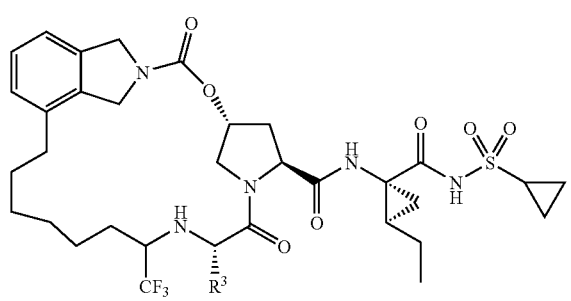
Scheme 3
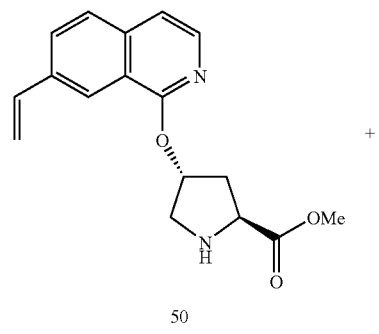
50
24
-continued
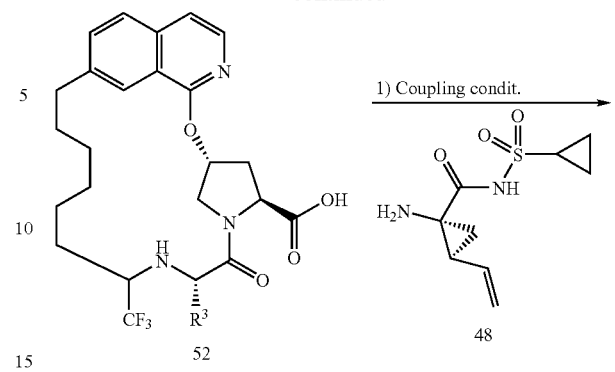
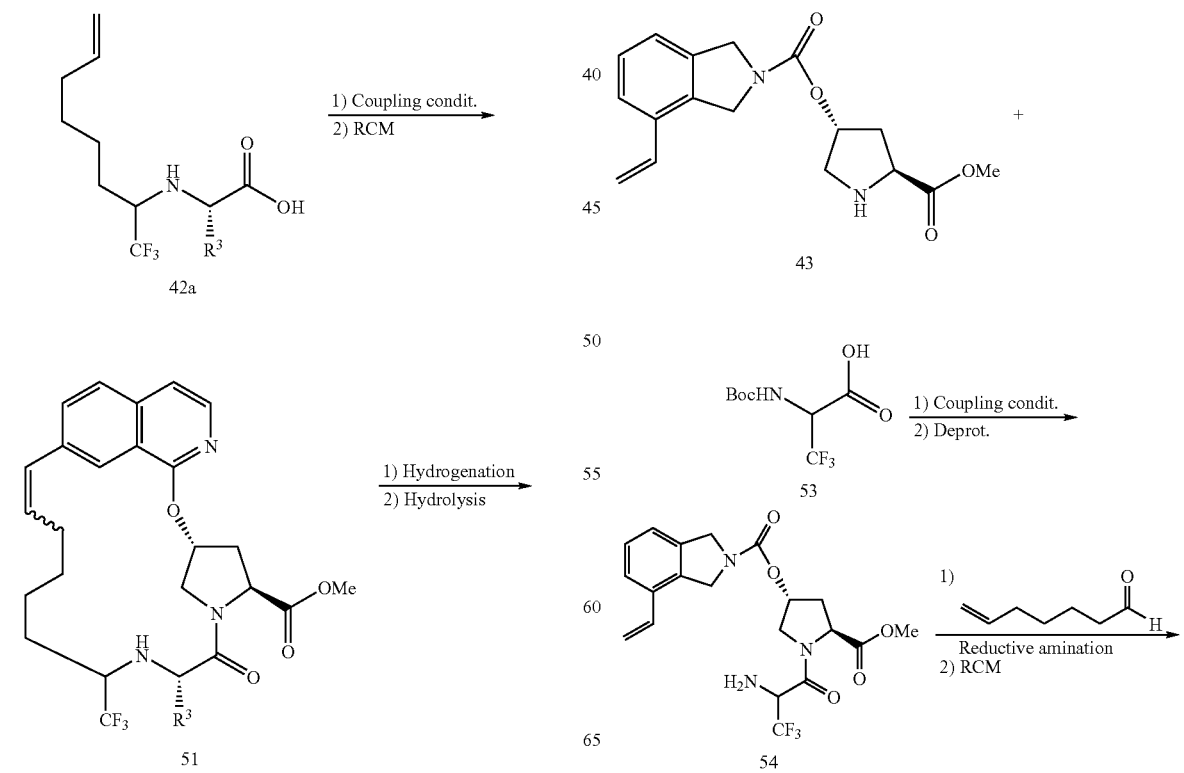

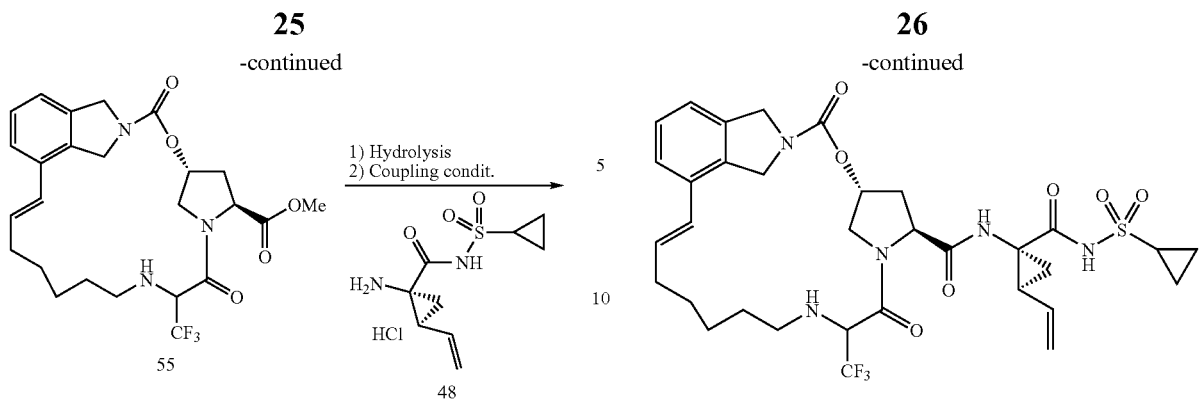
Scheme 5
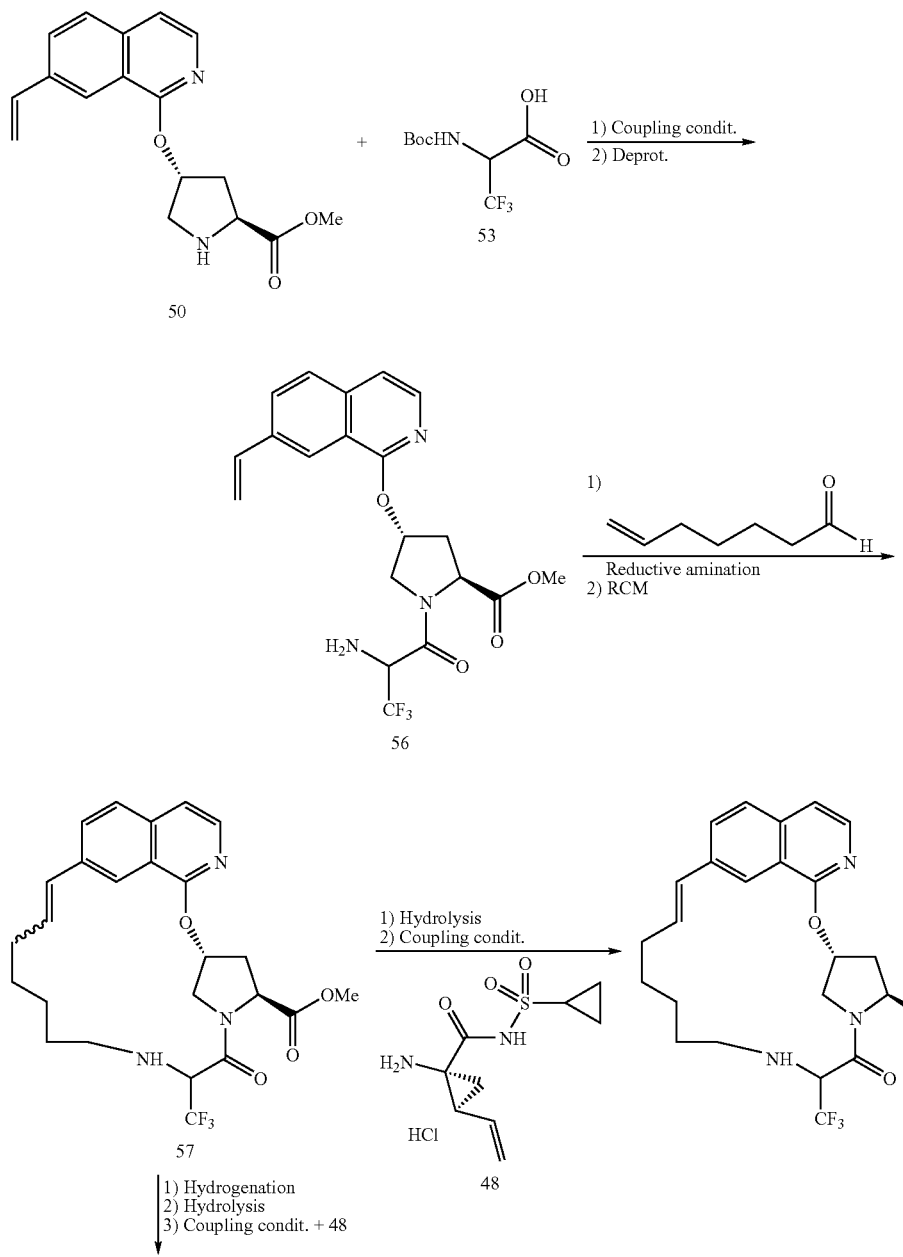

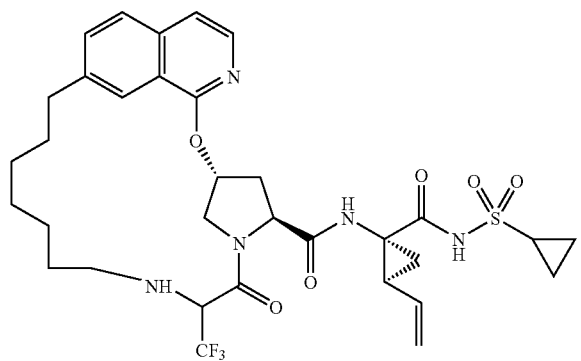
Scheme 6
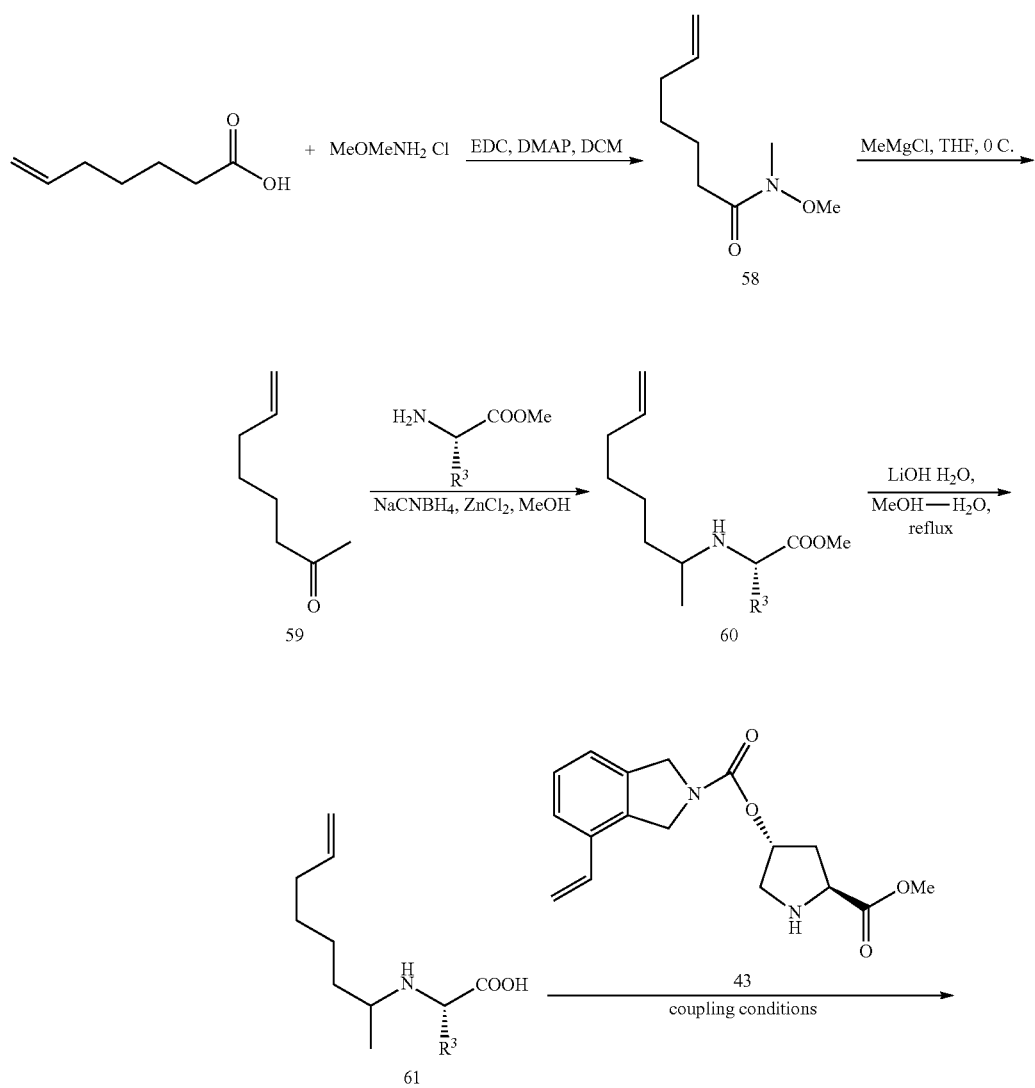

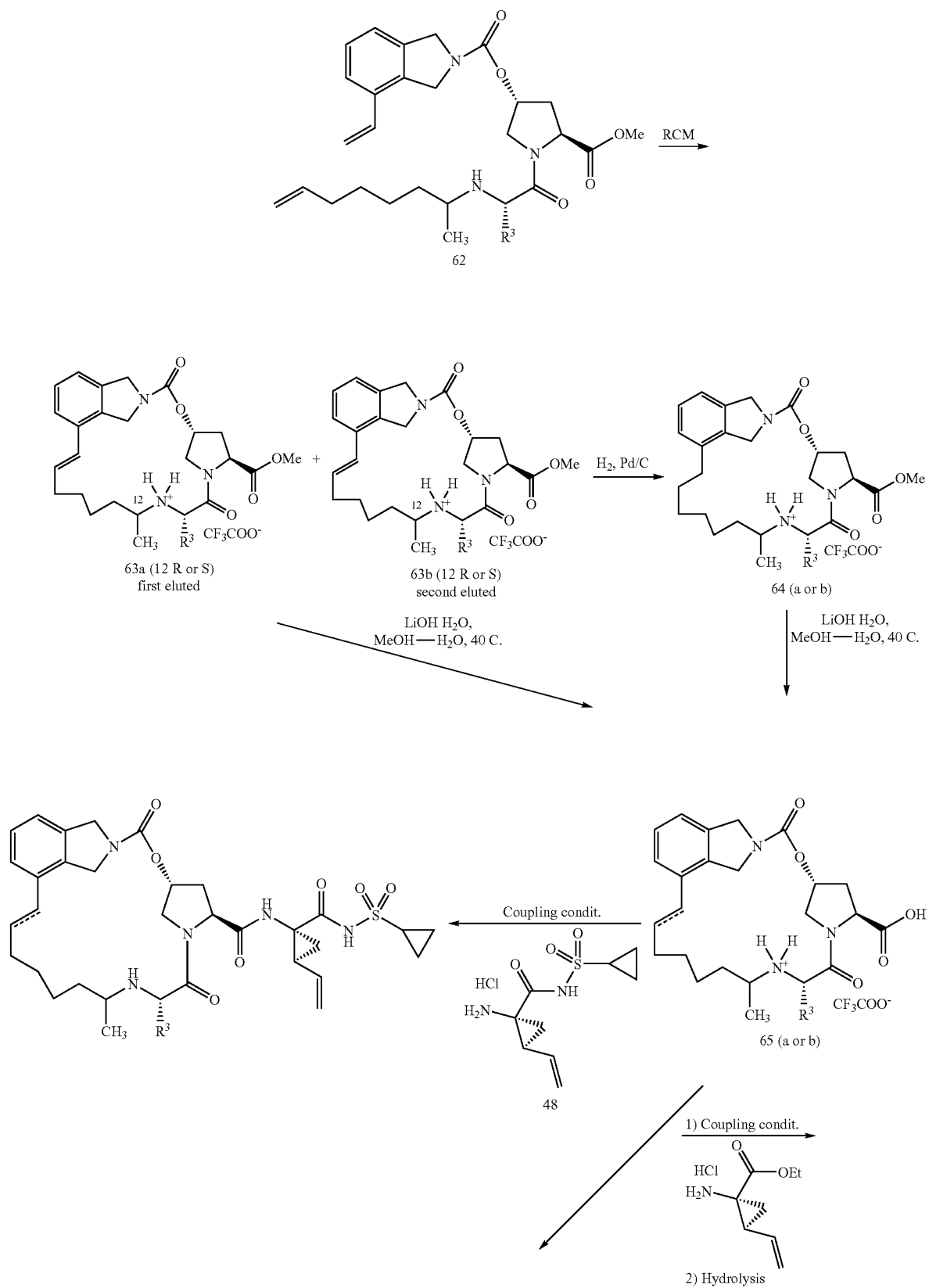

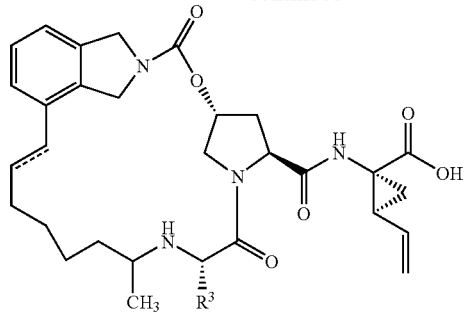

Compounds 10 and 25

10) (5R,7S,10S,12R or S)-N-((1R,2S)-1-{[(cyclopropylsulfonyl)amino]carbonyl}-2-vinylcyclopropyl)-10-isopropyl-12-methyl-3,9-dioxo-6,7,9,10,11,12,13,14,15,16,17,18-dodecahydro-1H,5H-2,22:5,8-dimethano-4,2,8,11-benzoxatriazacycloicosine-7-carboxamide 25) (5R,7S,10S,12R or S)-10-cyclohexyl-N-((1R,2S)-1-{[(cyclopropylsulfonyl)amino]carbonyl}-2-vinylcyclopropyl)-12-methyl-3,9-dioxo-6,7,9,10,11,12,13,14,15,16,17,18-dodecahydro-1H,5H-2,22:5,8-dimethano-4,2,8,11-benzoxatriazacycloicosine-7-carboxamide

Step 1: N-methoxy-N-methylhept-6-enamide 58

EDC (1.1 eq.) was added in small portions over 1.5 h to a stirred mixture of hept-6-enoic acid, methoxy(methyl)ammonium chloride (1.1 eq.) and DMAP (1.1 eq.) in CH$_2$Cl$_2$ (0.2 M). After 14 h, the mixture was diluted with CH$_2$Cl$_2$, then washed sequentially with hydrochloric acid (1 M), NaOH (1M), brine and dried (Na$_2$SO$_4$). Evaporation of the solvent afforded the title compound (97%) as a colorless oil. $^1$H NMR (400 MHz, CDCl$_3$, 300 K) δ 5.87-5.75 (m, 1H), 5.01 (d, J 17.1, 1H), 4.95 (d, J 10.1, 1H), 3.68 (s, 3H), 3.18 (s, 3H), 2.48-2.36 (m, 2H), 2.13-2.04 (m, 2H), 1.71-1.60 (m, 2H), 1.50-1.40 (m, 2H).

Step 2: oct-7-en-2-one 59

Methyl magnesium bromide (3M in ether, 3 eq.) was added dropwise to a stirred mixture of N-methoxy-N-methylhept-6-enamide 58 in THF (0.1 M) cooled at 0° C. After sting for 1 h at 0° C., the mixture was poured into sat. aq. NH$_4$Cl and diluted with EtOAc. The aqueous layer was further extracted with EtOAc, the combined organic layers were washed with brine and dried (Na$_2$SO$_4$). Evaporation of the solvent at 30 mbar afforded the title compound (96%) as a colorless oil. $^1$H NMR (400 MHz, CDCl$_3$, 300 K) δ 5.81 (ddt, J 17.1, 10.3, 6.7, 1H), 5.02 (dd, J 17.1, 1.5, 1H), 4.97 (d, J 10.3, 1H), 2.46-2.43 (m, 2H), 2.15 (s, 3H), 2.10-2.05 (m, 2H), 1.65-1.57 (m, 2H), 1.45-1.37 (m, 2H).

Step 3: Methyl (2S)-3-methyl-2-{[(1S and R)-1-methylhept-6-en-1-yl]amino}butanoate 60 (R$^3$=iPr)

A solution of NaCNBH$_3$ (1.2 eq.) and ZnCl$_2$ (0.6 eq.) in methanol (0.3 M with respect to NaCNBH$_3$) was added dropwise to a solution of L-valine methyl ester hydrochloride (1.1 eq.) and oct-7-en-2-one 59 in methanol (0.5 M). After sting for 2 days, volatiles were evaporated under reduced pressure and the residue partitioned between CH$_2$Cl$_2$ and sat. aq. NaHCO$_3$. The organic layer was dried (Na$_2$SO$_4$) and evaporated under reduced pressure affording the title compounds (57%) as a colorless oil. MS (ES$^+$) m/z 242 (M+H)$^+$.

Step 3: Methyl (2S)-cyclohexyl-{[(1R and S)-1-methylhept-6-en-1-yl)amino]acetate 60 (R$^3$=cHex)

A solution of NaCNBH$_3$ (1.2 eq.) and ZnCl$_2$ (0.6 eq.) in methanol (0.2 M with respect to NaCNBH$_3$) was added dropwise to a solution of (1S)-1-cyclohexyl-2-methoxy-2-oxoethanaminium chloride (1.1 eq.) and oct-7-en-2-one 59 in methanol (0.05 M). After sting overnight, volatiles were evaporated under reduced pressure and the residue partitioned between CH$_2$Cl$_2$ and sat. aq. NaHCO$_3$. The organic layer was dried (Na$_2$SO$_4$) and evaporated under reduced pressure. The title compounds (obtained as a mixture of two diastereoisomers in ratio 7:2) was used in the following step without further purification. MS (ES$^+$) m/z 282 (M+H)$^+$.

Step 4: (2S)-3-methyl-2-{[(1S and 1R)-1-methylhept-6-en-1-yl]amino}butanoic acid 61 (R$^3$=iPr)

Lithium hydroxide monohydrate (3.3 eq.) was added to a stirred mixture of methyl (2S)-3-methyl-2-{[(1S and R)-1-methylhept-6-en-1-yl]amino}butanoate 60 in MeOH and water (3/1 v/v, 0.03 M) and the mixture was stirred at reflux. After 22 h it was cooled to RT and MeOH was evaporated under reduced pressure. 1N HCl was added until pH=5, and the aq. phase was extracted with CH$_2$Cl$_2$. The organic layers were dried (Na$_2$SO$_4$) and evaporated under reduced pressure affording the title compound (65%) as a white solid. MS (ES$^+$) m/z 228 (M+H)$^+$.

Step 4: (2R and S)-N-[(S)-carboxy(cyclohexyl)methyl]oct-7-en-2-aminium chloride 61 (R$^3$=cHex)

Lithium hydroxide monohydrate (4 eq.) was added to a stirred mixture of methyl (2S)-cyclohexyl-{[(1R and S)-1-methylhept-6-en-1-yl)amino]acetate 60 in THF and water (3/2 v/v, 0.1 M) and the mixture was stirred at reflux. After 30 h, the mixture was cooled to RT and THF was evaporated under reduced pressure. 1N HCl was added until pH=5, and the aq. phase was extracted with EtOAc. HCl (4N) in dioxane (2 eq.) was added to the organic layers. Drying over Na$_2$SO$_4$, filtration and evaporation under reduced pressure afforded the title compounds as mixture of diastereomers that was used in the following step without further purification. MS (ES$^+$) m/z 268 (M+H)$^+$.

Step 5: (2R and S)-N-{(1S)-1-[((2S,4R)-2-(methoxy-carbonyl)-4-{[(4-vinyl-1,3-dihydro-2H-isoindol-2-yl)carbonyl]oxy}pyrrolidin-1-yl)carbonyl]-2-methylpropyl}oct-7-en-2-aminium trifluoroacetate 62 ($R^3$=iPr)

i-Pr$_2$EtN (4 eq.) followed by TBTU (1.2 eq.) were added to a stirred mixture of (2S)-3-methyl-2-{[(1S and 1R)-1-methylhept-6-en-1-yl]amino}butanoic acid 61 and (2S,4R)-2-(methoxycarbonyl)-4-{[(4-vinyl-1,3-dihydro-2H-isoindol-2-yl)carbonyl]oxy}pyrrolidinium chloride 43 (1 eq.) in CH$_2$Cl$_2$ (0.03 M) and the mixture was stirred at RT. After 3.5 h, sat. aq. NaHCO$_3$ was added, the organic layer was separated and dried (Na$_2$SO$_4$). Evaporation under reduced pressure afforded a residue, which was redissolved in DMSO and purified by RP-HPLC (stationary phase: column SYMMETRY C18, 7 μm, 19×300 mm. Mobile phase: MeCN/H$_2$O buffered with 0.1% TFA). Fractions containing the pure compounds were combined and freeze dried to afford the title compounds as a white powder (76%). MS (ES$^+$) m/z 526 (M+H)$^+$.

Step 5: (3R,5S)-1-{(2S)-2-cyclohexyl-2-[((1R and S)-1-methylhept-6-en-1-yl)amino]acetyl}-5-(methoxycarbonyl)pyrrolidin-3-yl-4-vinyl-1,3-dihydro-2H-isoindole-2-carboxylate 62 ($R^3$=cHex)

i-Pr$_2$EtN (5 eq.) followed by TBTU (1.2 eq.) were added to a stirred mixture of (2R and S)-N-[(S)-carboxy(cyclohexyl)methyl]oct-7-en-2-aminium chloride 61 and (2S,4R)-2-(methoxycarbonyl)-4{[(4-vinyl-1,3-dihydro-2H-isoindol-2-yl)carbonyl]oxy}pyrrolidinium chloride 43 (1 eq.) in CH$_2$Cl$_2$ (0.03 M) and the mixture was stirred at RT overnight. Saturated aq. NaHCO$_3$ was added, the organic layer was separated and dried (Na$_2$SO$_4$). Evaporation under reduced pressure afforded a residue that was purified by flash chromatography on silica gel (EtOAc/PE+0.05% TEA gradient from 10\90 to 35\65) to afford the title compound as a mixture of two diastereomers (45% over three steps). MS (ES$^+$) m/z 566 (M+H)$^+$.

Step 6: (5R,7S, 10S, 12R or S, 17E)-10-isopropyl-7-(methoxycarbonyl)-12-methyl-3,9-dioxo-6,7,9,10,11,12,13,14,15,16-dec-hydro-1H,5H-2, 22:5,8-dimethano-4,2,8,11-benzoxatriazacycloicosin-11-ium trifluoroacetate 63a ($R^3$=iPr)

Zhan catalyst I (0.2 eq.) was added to (2R and S)-N-{(1S)-1-[((2S,4R)-2-(methoxycarbonyl)-4-{[(4-vinyl-1,3-dihydro-2H-isoindol-2-yl)carbonyl]oxy}pyrrolidin-1-yl)carbonyl]-2-methylpropyl}oct-7-en-2-aminium trifluoroacetate 62 in CH$_2$Cl$_2$ (0.016 M) and the mixture was heated under microwave irradiation at 100° C. for 40 min. Undissolved material was filtered away and the resulting solution was evaporated under reduced pressure affording a residue, which was redissolved with DMSO and purified by RP-HPLC (stationary phase: column SYMMETRY C18, 7 μm, 19×300 mm. Mobile phase: MeCN/H$_2$O buffered with 0.1% TFA; the title compound 63a was the first diastereoisomer eluted). Fractions containing the pure compounds were combined and freeze dried to afford the title compounds as a white powder (37%). MS (ES$^+$) m/z 498 (M+H)$^+$.

Step 6: (5R,7S,10S,12R or S)-10-cyclohexyl-7-(methoxycarbonyl)-12-methyl-3,9-dioxo-6,7,9,10,11,12,13,14,15,16-decahydro-1H,5H-2, 22:5,8-dimethano-4,2,8,11-benzoxatriazacycloicosin-11-ium trifluoroacetate 63a ($R^3$=cHex)

Zhan catalyst I (0.2 eq.) was added to (3R,5S)-1-{(2S)-2-cyclohexyl-2-[((1R and S)-1-methylhept-6-en-1-yl)amino] acetyl}-5-(methoxycarbonyl)pyrrolidin-3-yl 4-vinyl-1,3-dihydro-2H-isoindole-2-carboxylate 62 in CH$_2$Cl$_2$ (0.02 M) and the mixture was heated under microwave irradiation at 100° C. for 40 min. Volatiles were evaporated under reduced pressure affording a residue, which was redissolved with DMSO and purified by RP-HPLC (stationary phase: column SYMMETRY C18, 7 μm, 19×300 mm. Mobile phase: MeCN/H$_2$O buffered with 0.1% TFA). The title compound 63a was The first diastereoisomer eluted. The fractions containing the pure compounds were combined and freeze dried to afford the title compounds as a white powder (31%).

63a) $^1$H NMR (300 MHz, DMSO-d$_6$, 300 K) δ 8.60 (br s, 2H), 7.35-7.15 (m, 3H), 6.27 (d, J 16.4, 1H,), 6.07 (dt, J 15.8, 5.7, 1H), 5.42 (br s, 1H), 4.89-4.54 (m, 4H), 4.46 (d, J 14.8, 1H), 4.40-4.31 (m, 1H), 4.26 (d, J 12.2, 1H), 3.76-3.60 (m, 4H), 2.95-2.77 (m, 1H), 2.47-2.40 (partially obscured by residual DMSO, 1H), 2.30-2.03 (m, 3H), 2.01-1.71 (m, 6H), 1.70-0.97 (m, 14H). MS (ES$^+$) m/z 538 (M+H)$^+$.

Step 7: (5R,7S,10S,12R or S)-10-isopropyl-7-(methoxycarbonyl)-12-methyl-3,9-dioxo-6,7,9,10,11,12,13,14,15,16,17,18-dodecahydro-1H,5H-2, 22:5,8-dimethano-4,2,8,11-benzoxatriazacycloicosin-11-ium trifluoroacetate 64a ($R^3$=iPr)

Palladium on carbon (10% Pd, 20% weight) and (5R,7S,10S,12R or S,17E)-10-isopropyl-7-(methoxycarbonyl)-12-methyl-3,9-dioxo-6,7,9,10,11,12,13,14,15,16-decahydro-1H,5H-2, 22:5,8-dimethano-4,2,8,11-benzoxatriazacycloicosin-11-ium trifluoroacetate 63a in MeOH (5 mM) were stirred under a hydrogen atmosphere. After 2 h, solids were filtered away on CELITE and the resulting solution was evaporated under reduced pressure affording the title compound (67%) as a pale brown oil. MS (ES$^+$) m/z 500 (M+H)$^+$.

Step 7: (5R,7S,10S,12R or S)-10-cyclohexyl-7-(methoxycarbonyl)-12-methyl-3,9-dioxo-6,7,9,10,11,12,13,14,15,16,17,18-dodecahydro-1H,5H-2, 22:5,8-dimethano-4,2,8,11-benzoxatriazacycloicosin-11-ium trifluoroacetate 64a ($R^3$=cHex)

Palladium on carbon (10% Pd, 20% weight) and (5R,7S,10S,12R or S)-10-cyclohexyl-7-(methoxycarbonyl)-12-methyl-3,9-dioxo-6,7,9,10,11,12,13,14,15,16-decahydro-1H,5H-2, 22:5,8-dimethano-4,2,8,11-benzoxatriazacycloicosin-11-ium trifluoroacetate 63a in methanol (0.013M) were stirred under a hydrogen atmosphere. After 3 h, solids were filtered away on CELITE and the resulting solution was evaporated under reduced pressure affording the title compound (88%) as a pale brown oil. MS (ES$^+$) m/z 540 (M+H)$^+$.

Step 8: (5R,7S,10S,12R or S)-7-carboxy-10-isopropyl-12-methyl-3,9-dioxo-6,7,9,10,11,12,13,14,15,16,17,18-dodecahydro-1H,5H-2, 22:5,8-dimethano-4,2,8,1-benzoxatriazacycloicosin-11-ium trifluoroacetate 65a ($R^3$=iPr)

Lithium hydroxide monohydrate (12 eq.) was added to a stirred mixture of (5R,7S,10S,12R or S)-10-isopropyl-7-(methoxycarbonyl)-12-methyl-3,9-dioxo-6,7,9,10,11,12,13,14,15,16,17,18-dodecahydro-1H,5H-2, 22:5,8-dimethano-4,2,8,11-benzoxatriazacycloicosin-11-ium trifluoroacetate 64a in MeOH and water (3/1 v/v, 0.01 M) and the mixture was stirred at 40° C. After 6 h, the mixture was cooled, TFA was added to pH=1 and the mixture was evaporated under reduced pressure affording a residue, which was redissolved with DMSO and purified by RP-HPLC (stationary phase: column SYMMETRY C18, 5 μm, 19×100 mm. Mobile phase: MeCN/H₂O buffered with 0.1% TFA). Fractions containing the pure compound were combined and freeze dried to afford the title compound 65a as a white powder (57%). MS (ES⁺) m/z 486 (M+H)⁺.

Step 8: (5R,7S,10S,12R or S)-7-carboxy-10-cyclohexyl-12-methyl-3,9-dioxo-6,7,9,10,11,12,13,14,15,16,17,18-dodecahydro-1H,5H-2, 22:5,8-dimethano-4,2,8,1-benzoxatriazacycloicosin-11-ium trifluoroacetate 65a (R³=cHex)

Lithium hydroxide monohydrate (5 eq.) was added to a stirred mixture of (5R,7S,10S,12R or S)-10-cyclohexyl-7-(methoxycarbonyl)-12-methyl-3,9-dioxo-6,7,9,10,11,12,13,14,15,16,17,18-dodecahydro-1H,5H-2, 22:5,8-dimethano-4,2,8,11-benzoxatriazacycloicosin-11-ium trifluoroacetate 64a in THF and water (2/1 v/v, 0.01 M) and the mixture was stirred at 40° C. After 6 h the mixture was cooled, TFA was added to pH=1 and the mixture was evaporated under reduced pressure affording a residue, which was redissolved with DMSO and purified by RP-HPLC (stationary phase: column SYMMETRY C18, 5 μm, 19×100 mm. Mobile phase: MeCN/H₂O buffered with 0.1% TFA). Fractions containing the pure compound were combined and freeze dried to afford the title compound as a white powder (44%). MS (ES⁺) m/z 526 (M+H)⁺.

Step 9: (5R,7S,10S,12R or S)-N-((1R,2S)-1-{[(cyclopropylsulfonyl)amino]carbonyl}-2-vinylcyclopropyl)-10-isopropyl-12-methyl-3,9-dioxo-6,7,9,10,11,12,13,14,15,16,17,18-dodecahydro-1H,5H-2, 22:5,8-dimethano-4,2,8,11-benzoxatriazacycloicosine-7-carboxamide 10 i-Pr₂EtN (7.5 eq.), DMAP (0.5 eq.) and TBTU (1.3 eq.) were added to a stirred mixture of (5R,7S,10S,12R or S)-10-isopropyl-7-(methoxycarbonyl)-12-methyl-3,9-dioxo-6,7,9,10,11,12,13,14,15,16,17,18-dodecahydro-1H,5H-2, 22:5,8-dimethano-4,2,8,11-benzoxatriazacycloicosin-11-ium trifluoroacetate 65a and (1R,2S)-1-{[(cyclopropylsulfonyl)amino]carbonyl}-2-vinylcyclopropanaminium chloride 48 (prepared as described in WO 03/099274) (1.5 eq.) in CH₂Cl₂ (0.02 M) and the mixture was stirred at RT. After 13 h, the mixture was evaporated under reduced pressure affording a residue, which was redissolved with DMSO and purified by RP-HPLC (stationary phase: column SYMMETRY C18, 7 μm, 19×300 mm. Mobile phase: MeCN/H₂O buffered with 0.1% TFA). Fractions containing the pure compound were combined and freeze dried to afford the title compound 10 (TFA salt) as a white powder 57%). ¹H NMR (600 MHz, DMSO-d₆, 300 K) δ 10.90 (br s, NH), 8.73 (br s, NH), 8.50-8.25 (m, NH₂), 7.26 (t, J 7.3, 1H), 7.18 (d, J 7.4, 1H), 7.14 (d, J 7.4, 1H), 5.56 (dt, J 17.5, 9.5, 1H), 5.41 (br s, 1H), 5.22 (d, J 17.5, 1H), 5.11 (d, J 11.1, 1H), 4.67 (m, 2H), 4.62-4.49 (m, 3H), 4.40-4.34 (m, 1H), 4.18 (d, J 12.2, 1H), 3.74 (dd, J 12.2, 2.5, 1H), 2.94-2.82 (m, 2H), 2.52-2.43 (obscured by residual DMSO, 2H), 2.42-2.34 (m, 1H), 2.23 (m, 1H), 2.15 (q, J 8.7, 1H), 2.06 (m, 1H), 1.74 (dd, J 7.6, 5.5, 1H), 1.71 (m, 1H), 1.63-1.44 (m, 3H), 1.41-0.97 (m, 20H). MS (ES⁺) m/z 698 (M+H)⁺.

Step 9: (5R,7S,10S,12R or S)-10-cyclohexyl-N-((1R,2S)-1-{[(cyclopropylsulfonyl)amino]carbonyl}-2-vinylcyclopropyl)-12-methyl-3,9-dioxo-6,7,9,10,11,12,13,14,15,16,17,18-dodecahydro-1H,5H-2,22:5,8-dimethano-4,2,8,11-benzoxatriazacycloicosine-7-carboxamide 25 i-Pr₂EtN (6.5 eq.), DMAP (0.5 eq.) and TBTU (1.3 eq.) were added to a stirred mixture of (5R,7S,10S,12R or S)-7-carboxy-10-cyclohexyl-12-methyl-3,9-dioxo-6,7,9,10,11,12,13,14,15,16,17,18-dodecahydro-1H,5H-2, 22:5,8-dimethano-4,2,8,11-benzoxatriazacycloicosin-11-ium trifluoroacetate 65a and (1R,2S)-1-{[(cyclopropylsulfonyl)amino]carbonyl}-2-vinylcyclopropanaminium chloride (prepared as described in WO 03/099274) (1.5 eq.) 48 in CH₂Cl₂ (0.02 M) and the mixture was stirred at RT overnight. Volatiles were evaporated under reduced pressure affording a residue, which was redissolved with DMSO and purified by RP-HPLC (stationary phase: column SYMMETRY C18, 7 μm, 19×300 mm. Mobile phase: MeCN/H₂O buffered with 0.1% TFA). Fractions containing the pure compound were combined and freeze dried to afford the title compound 25 (TFA salt) as a white powder (62%). ¹H NMR (400 MHz, DMSO-d₆, 300 K) δ 10.85 (br s, 1H), 8.73 (br s, 1H), 8.43 (br s, 1H), 8.34-8.20 (m, 1H), 7.26 (t, J 7.5, 1H,), 7.18 (d, J 7.6, 1H), 7.14 (d, J 7.4, 1H), 5.58 (dt, J 17.7, 9.1, 1H), 5.41 (br s, 1H), 5.21 (d, J 17.4, 1H), 5.11 (d, J 11.4, 1H), 4.72-4.45 (m, 5H), 4.48-4.39 (m, 1H), 4.17 (d, J 12.1, 1H), 3.76 (dd, J 12.9, 2.3, 1H), 2.97-2.78 (m, 2H), 2.47-2.34 (partially obscured by residual DMSO, 2H), 2.19-2.03 (m, 2H), 1.99-1.42 (m, 11H), 1.41-0.93 (m, 20H). MS (ES⁺) m/z 738 (M+H)⁺.

Scheme 7

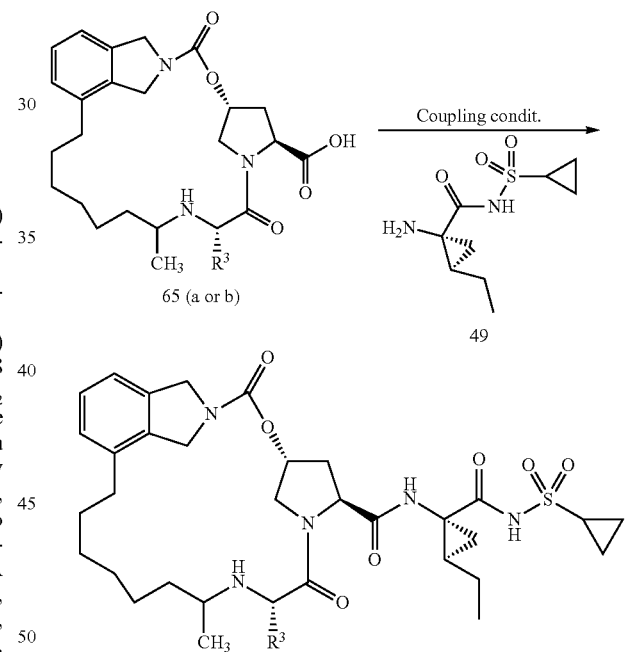

Scheme 8

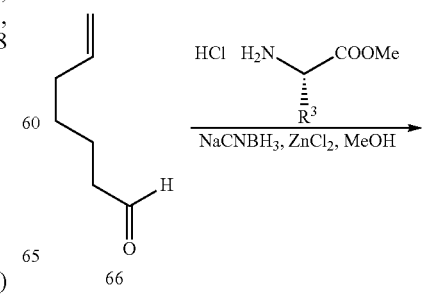

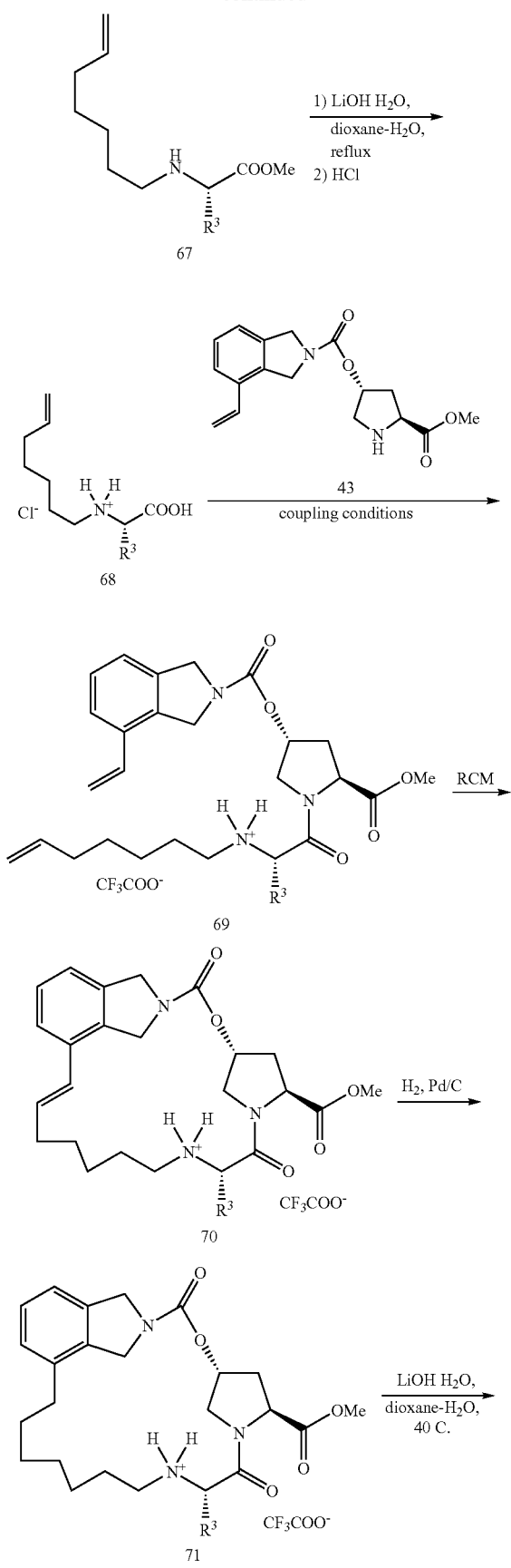
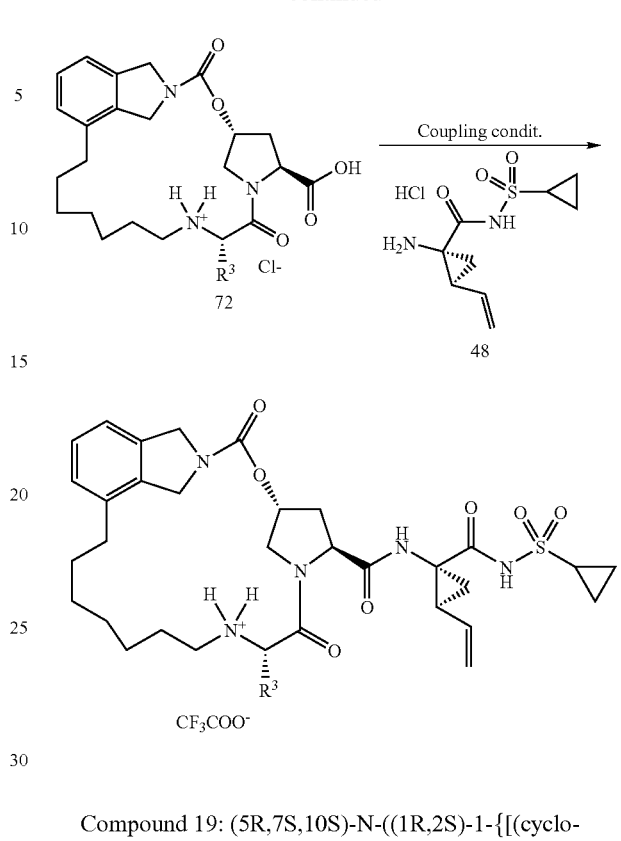

Compound 19: (5R,7S,10S)-N-((1R,2S)-1-{[(cyclo-propylsulfonyl)amino]carbonyl}-2-vinylcyclopropyl)-10-isopropyl-3,9-dioxo-6,7,9,10,11,12,13,14,15,16,17,18-dodecahydro-1H,5H-2,22:5,8-dimethano-4,2,8,11-benzoxatriazacycloicosine-7-carboxamide Step 1: Methyl (2S)-2-(hept-6-en-1-ylamino)-3-methylbutanoate 67 ($R^3$=iPr)

To a solution (0.3M) of L-valine, methyl ester, hydrochloride in dry MeOH was added $ZnCl_2$ (1.0 eq.), $NaCNBH_3$ (1.2 eq.), hept-6-enal 66 (1.2 eq.), and the reaction mixture was stirred at RT overnight. Then the volatiles were evaporated at reduced pressure and the residue taken-up in $CH_2Cl_2$ and washed with a saturated aq. solution of $NaHCO_3$. The organic layer was dried over $Na_2SO_4$ and evaporated at reduced pressure affording the title compound (98%) as yellow pale oil.

$^1$H NMR (400 MHz, $CDCl_3$, 300 K) δ 5.81 (ddt, J 17.0, 10.1, 6.7, 1H), 5.00 (dd, J 17.0, 1.5, 1H), 4.94 (d, J 10.1, 1H), 3.72 (s, 3H), 2.99 (d, J 5.6, 1H), 2.60-2.54 (m, 1H), 2.45-2.39 (m, 1H), 2.05 (dd, J 13.5, 6.6, 2H), 1.94-1.86 (m, 1H), 1.53-1.26 (m, 6H), 0.96 (d, J 7.1, 3H), 0.93 (d, J 6.8, 3H).

Step 2: N-[(1S)-1-carboxy-2-methylpropyl]hept-6-en-1-aminium chloride 68 ($R^3$=iPr)

To a solution (0.4M) of methyl (2S)-2-(hept-6-en-1-ylamino)-3-methylbutanoate 67 in a 1:1 mixture of dioxane and water, LiOH (4 eq.) was added, and the reaction mixture was stirred at reflux for 24 h. The reaction mixture was then cooled and brought to pH=2 by small additions of HCl$_{(aq)}$ 6N. The white precipitate was filtered and washed with H$_2$O and dried overnight. The title compound (71%) as a white precipitate was used in the next step without any further purification. $^1$H NMR (400 MHz, DMSO-d6, 300 K) δ 9.80 (bs, 1H), 8.95 (bs, 1H), 5.74 (ddt, J 17.0, 16.9, 6.7, 1H), 4.95 (d, J 17.0, 1H), 4.89 (d, J 10.2, 1H), 3.73-3.70 (m, 1H), 2.91-2.72 (m, 2H), 2.43-2.35 (m, 1H), 1.96 (q, J 6.7, 2H), 1.78-1.65 (m, 2H), 1.33-1.24 (m, 4H), 1.01 (d, J 7.1, 3H), 0.92 (d, J 6.8, 3H).

Step 3: N-{(1S)-1-[((2S,4R)-2-(methoxycarbonyl)-4-{[(4-vinyl-[3-dihydro-2H-isoindol-2-yl)carbonyl]oxy}pyrrolidin-1-yl)carbonyl]-2-methylpropyl}hept-6-en-1-aminium trifluoroacetate 69 (R$^3$=iPr)

To a solution (0.1M) of N-[(1S)-1-carboxy-2-methylpropyl]hept-6-en-1-aminium chloride 68 in dry CH$_2$Cl$_2$ was added (2S,4R)-2-(methoxycarbonyl)-4-{[(4-vinyl-1,3-dihydro-2H-isoindol-2-yl)carbonyl]oxy}pyrrolidinium chloride 43 (1.2 eq.), i-Pr$_2$Et(3.2 eq.) and TBTU (1.2 eq.). The reaction mixture was stirred at RT for 4 h, then taken up in DCM and washed with an aq. saturated solution of NaHCO$_3$. The organic phase was dried over Na$_2$SO$_4$ and the volatiles evaporated at reduced pressure. The crude was purified by flash chromatography eluting with a mixture of PE/EtOAc (7/3) in presence with 0.1% of TEA. The desired fractions were collected and the solvent evaporated. The compound was solubilized in CH$_2$Cl$_2$ and 1 eq. of TFA was added in order to obtain the complete formation of the trifluoroacetate salt. The procedure afforded the title compound (90%) as a white solid. MS (ES$^+$) m/z 512 (M+H)$^+$.

Step 4: N-(5R,7S,10S,17E)-10-isopropyl-7-(methoxycarbonyl)-3,9-dioxo-6,7,9,10,11,12,13,14,15,16-decahydro-1H,5H-2, 22:5,8-dimethano-4,2,8,11-benzoxatriazacycloicosin-11-ium trifluoroacetate 70 (R$^3$=iPr)

Zhan catalyst I (0.05 eq.) was added to N-{(1S)-1-[((2S,4R)-2-(methoxycarbonyl)-4-{[(4-vinyl-1,3-dihydro-2H-isoindol-2-yl)carbonyl]oxy}pyrrolidin-1-yl)carbonyl]-2-methylpropyl} hept-6-en-1-aminium trifluoroacetate 69 in DCE (0.04 M) and the mixture was heated at 90° C. for 1 h. The volatiles were then evaporated at reduced pressure and the crude crystallized from a mixture of PE/EtOAc 8/2. The precipitate was collected and dried overnight. The title compound (78%) was obtained as a brownish solid. MS (ES$^+$) m/z 484 (M+H)$^+$.

Step 5: (5R,7S,10S)-10-isopropyl-7-(methoxycarbonyl)-3,9-dioxo-6,7,9,10,11,12,13,14,15,16,17,18-dodecahydro-1H,5H-2, 22:5,8-dimethano-4,2,8,11-benzoxatriazacycloicosin-11-ium trifluoroacetate 71 (R$^3$=iPr)

Palladium on carbon (10% Pd, 20% weight) and N-(5R,7S,10S,17E)-10-isopropyl-7-(methoxycarbonyl)-3,9-dioxo-6,7,9,10,11,12,13,14,15,16-decahydro-1H,5H-2, 22:5,8-dimethano-4,2,8,11-benzoxatriazacycloicosin-11-ium trifluoroacetate 70 in MeOH (1 mM) were stirred overnight under hydrogen atmosphere. Then the catalyst was filtered-off and the volatiles evaporated. The title compound (95%) was recovered as a brown solid. MS (ES) m/z 487 (M+H)$^+$.

Step 6: (5R,7S,10S)-7-carboxy-10-isopropyl-3,9-dioxo-6,7,9,10,11,12,13,14,15,16,17,18-dodecahydro-1H,5H-2, 22:5,8-dimethano-4,2,8,11-benzoxatriazacycloicosin-11-ium trifluoroacetate 72 (R$^3$=iPr)

Lithium hydroxide monohydrate (5 eq.) was added to a stirred mixture of (5R,7S,10S)-10-isopropyl-7-(methoxycarbonyl)-3,9-dioxo-6,7,9,10,11,12,13,14,15,16,17,18-dodecahydro-1H,5H-2, 22:5,8-dimethano-4,2,8,11-benzoxatriazacycloicosin-11-ium trifluoroacetate 71 in a 1:1 mixture of dioxane and H$_2$O (3 mM). By small aliquots of HCl$_{(aq)}$ 6N the pH was brought to 6.5 and the volatiles evaporated. The crude was taken up in a mixture 95:5 H$_2$O:MeCN and the solid was collected by suction. The title compound (quantitative recovery) was obtained as a light grey solid. MS (ES$^+$) m/z 472 (M+H)$^+$.

Step 7: (5R,7S,10S)-N-((1R,2S)-1-{[(cyclopropylsulfonyl)amino]carbonyl}-2-vinylcyclopropyl)-10-isopropyl-3,9-dioxo-6,7,9,10,11,12,13,14,15,16,17,18-dodecahydro-1H,5H-2, 22:5,8-dimethano-4,2,8,11-benzoxatriazacycloicosine-7-carboxamide 19 i-Pr$_2$EtN (3.5 eq.), DMAP (0.5 eq.), TBTU (1.5 eq.) were added to a stirred mixture of (5R,7S,10S)-7-carboxy-10-isopropyl-3,9-dioxo-6,7,9,10,11,12,13,14,15,16,17,18-dodecahydro-1H,5H-2, 22:5,8-dimethano-4,2,8,11-benzoxatriazacycloicosin-11-ium trifluoroacetate 72 and (1R,2S)-1-{[(cyclopropylsulfonyl)amino]carbonyl}-2-vinylcyclopropanaminium chloride (prepared as described in WO 03/099274) (1.5 eq.) 48 (1.5 eq.) in CH$_2$Cl$_2$ (0.06 M) and the mixture was stirred at RT for 2 h. The mixture was evaporated under reduced pressure affording a residue, which was redissolved with DMSO and purified by RP-HPLC (stationary phase: column SYMMETRY C18, 7 μm, 19×300 mm. Mobile phase: MeCN/H$_2$O buffered with 0.1% TFA). Fractions containing the pure compound were combined and freeze dried to afford the title compound 19 (TFA salt) as a white solid (23%).

$^1$H NMR (400 MHz, DMSO-d6, 300 K) δ 10.74 (s, 1H), 8.74 (s, 1H), 8.70-8.56 (m, 2H), 7.25 (t, J 7.6, 1H), 7.17 (d, J 7.8, 1H), 7.13 (d, J 7.3, 1H), 5.56 (dt, J 17.1, 9.3, 1H), 5.39 (br s, 1H), 5.22 (d, J 17.4, 1H), 5.11 (d, J 11.3, 1H), 4.78-4.48 (m, 5H), 4.27 (br s, 1H), 3.74 (dd, J 11.6, 2.5, 1H), 2.95-2.89 (m, 2H), 2.69-2.66 (m, 1H), 2.38-2.32 (obscured by residual DMSO, 1H), 2.21-2.06 (m, 3H), 1.73 (dd, J 9.7, 6.9, 2H), 1.69-1.55 (m, 4H), 1.32-1.26 (m, 1H), 4.49-4.62 (m, 7H), 1.15-1.09 (m, 1H), 1.04 (dd, J 9.7, 6.9, 9H). MS (ES$^+$) m/z 685 (M+H)$^+$.

Scheme 9

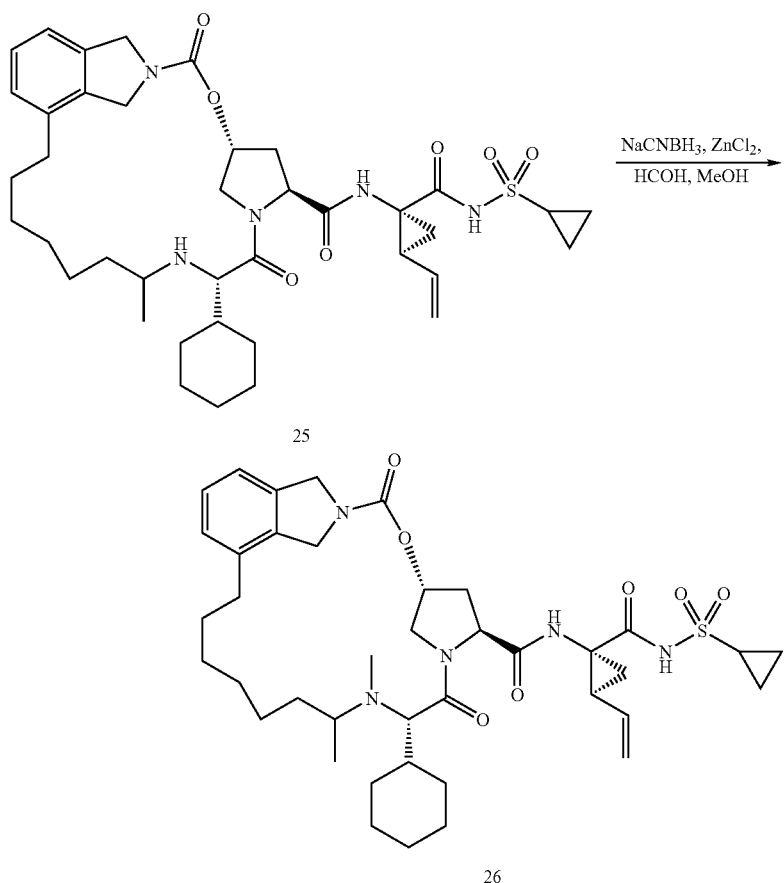

Compound 26: (5R,7S,10S,12R or S)-10-cyclohexyl-N-((1R,2S)-1-{[(cyclopropylsulfonyl)amino]carbonyl}-2-vinylcyclopropyl)-11,12-dimethyl-3,9-dioxo-6,7,9,10,11,12,13,14,15,16,17,18-dodecahydro-1H,5H-2, 22:5,8-dimethano-4,2,8,11-benzoxatriazacycloicosine-7-carboxamide A solution of NaCNBH$_3$ (1.2 eq.) and ZnCl$_2$ (0.6 eq.) in methanol (0.04 M with respect to NaCNBH$_3$) was added dropwise to a solution of 37% aq. formaldehyde (35 eq.) and (5R,7S, OS, 12R or S)-10-cyclohexyl-N-((1R,2S)-1-{[(cyclopropylsulfonyl)amino]carbonyl}-2-vinylcyclopropyl)-12-methyl-3,9-dioxo-6,7,9,10,11,12,13,14,15,16,17,18-dodecahydro-1H,5H-2, 22:5,8-dimethano-4,2,8,11-benzoxatriazacycloicosine-7-carboxamide 25 in MeOH (0.03 M). After stirring overnight, volatiles were evaporated under reduced pressure. The residue was redissolved with DMSO and purified by RP-HPLC (stationary phase: column SYMMETRY C18, 7 μm, 19×300 mm. Mobile phase: MeCN/H$_2$O buffered with 0.1% TFA). Fractions containing the pure compound were combined and freeze dried to afford the title compound 26 (TFA salt) as a white powder (55%). $^1$H NMR (400 MHz, DMSO-d6, 300 K) δ 10.88 (s, 1H), 8.73 (br s, 1H), 8.65 (br s, 1H), 7.26 (t, J 7.5, 1H), 7.19 (d, J 7.6, 1H), 7.13 (d, J 7.4, 1H), 5.60 (dt, J 17.3, 9.5, 1H), 5.37 (br s, 1H), 5.20 (d, J 17.0, 1H), 5.11 (d, J 11.1, 1H), 4.77-5.55 (m, 4H), 4.56-4.39 (m, 2H), 3.92 (d, J 12.1, 1H), 3.80 (dd, J 12.1, 2.5, 1H), 2.97-2.80 (m, 2H), 2.62 (d, J 4.0, 3H), 2.47-2.36 (partially obscured by residual DMSO, 3H), 2.15 (q, J 8.9, 1H), 2.10-1.93 (m, 2H), 1.92-1.41 (m, 12H), 1.40-1.81 (m, 11H), 1.17-0.94 (m, 6H). MS (ES) m/z 752 (M+H)$^+$.

Scheme 10

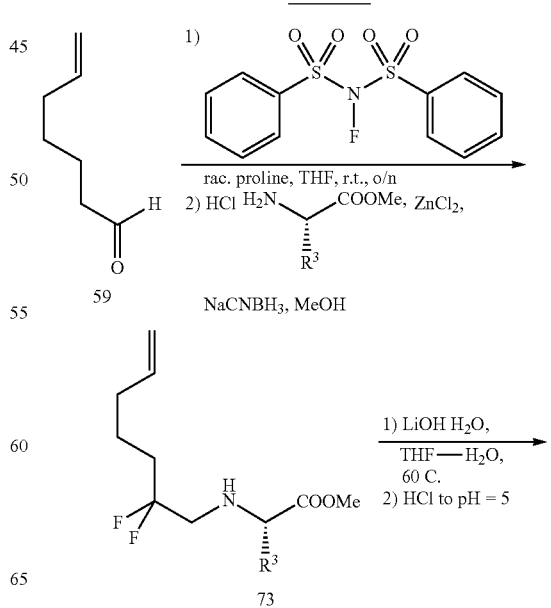

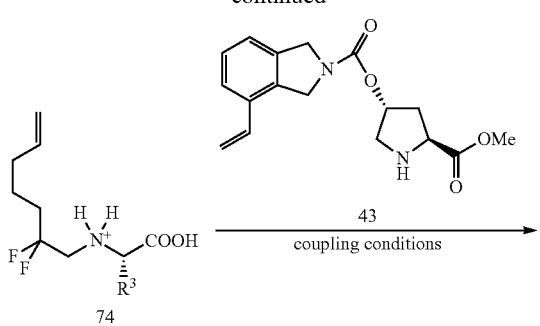

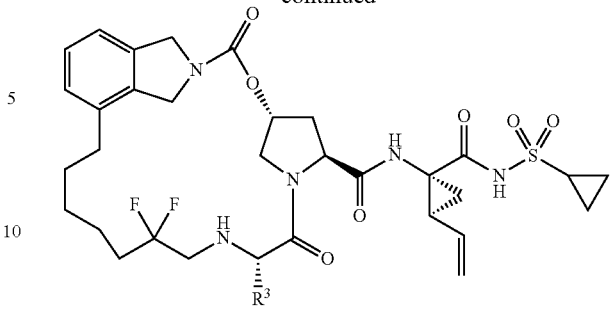

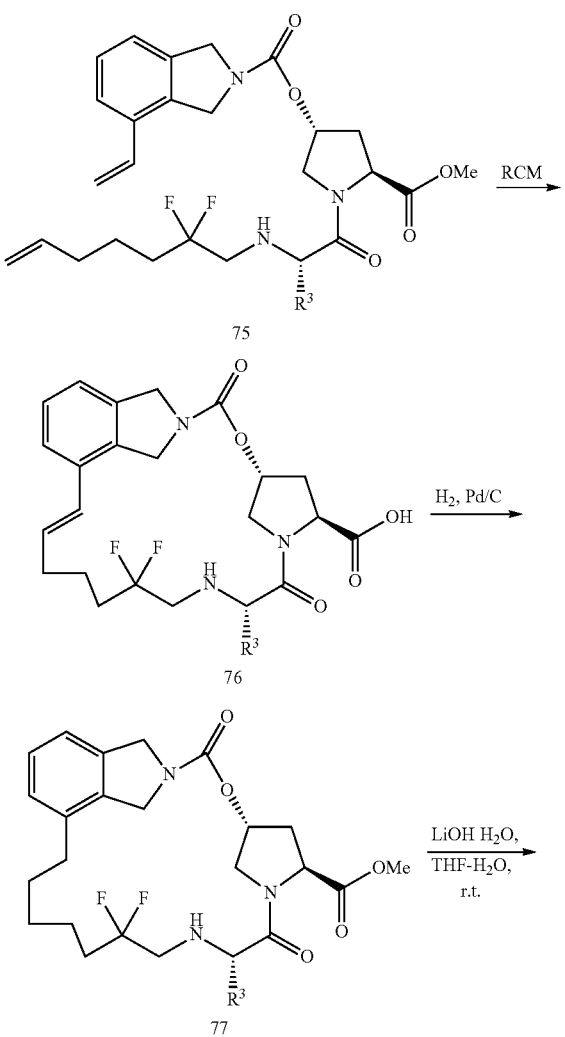

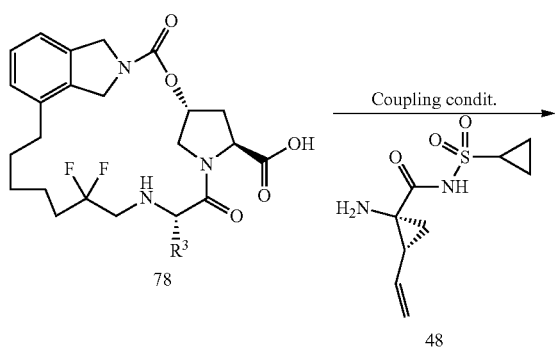

Compound 14: (5R,7S,10S)-N-((1R,2S)-1-{[(cyclo-propylsulfonyl)amino]carbonyl}-2-vinylcyclopropyl)-13,13-difluoro-10-isopropyl-3,9-dioxo-6,7,9,10,11,12,13,14,15,16,17,18-dodecahydro-1H,5H-2,22:5,8-dimethano-4,2,8,11-benzoxatriazacycloicosine-7-carboxamide Step 1: methyl N-(2,2-difluorohept-6-en-1-yl)-L-valinate 73

To hept-6-enal 59 dissolved in THF (0.09M), racemic proline, followed by N-fluoro-N-(phenylsulfonyl)benzenesulfonamide were added. The mixture was stirred at RT overnight. The reaction mixture was diluted with $Et_2O$ and washed with sat. aq. $NaHCO_3$. The organic layer was separated, dried over $Na_2SO_4$, filtered and concentrated. To the residue redissolved in MeOH (0.5 M), L-valine methyl ester hydrochloride (1.1 eq.) followed by a solution of $NaCNBH_3$ (1.2 eq.) and $ZnCl_2$ (0.6 eq.) in MeOH (0.3 M with respect to $NaCNBH_3$) were added dropwise. After sting overnight, volatiles were evaporated under reduced pressure and the residue partitioned between $CH_2Cl_2$ and sat. aq. $NaHCO_3$. The organic layer was dried ($Na_2SO_4$) and evaporated under reduced pressure. The residue was purified by flash chromatography on silica gel (EtOAc:PE=5:95) to afford the title compound as a yellow oil (25%). $^1H$ NMR (400 MHz, DMSO-$d_6$, 300 K) δ 5.86 (m, 1H), 5.03 (d, J 17.2, 1H), 5.0 (d, J 10.1, 1H), 3.65 (s, 3H), 3.05-2.87 (m, 2H), 2.76-2.60 (m, 1H), 2.25-2.15 (m, 1H), 2.13-1.99 (m, 2H), 1.97-1.77 (m, 3H), 1.56-1.40 (m, 2H), 0.86 (d, J 6.8, 6H). MS ($ES^+$) m/z 264 $(M+H)^+$.

Step 2: N-(2,2-difluorohept-6-en-1-yl)-L-valine 74

Lithium hydroxide monohydrate (6 eq.) was added to a stirred mixture of methyl N-(2,2-difluorohept-6-en-1-yl)-L-valinate 73 in THF and water (2/1 v/v, 0.013 M) and the mixture was stirred at 60° C. After 1 h, it was cooled to RT and THF was evaporated under reduced pressure. Aqueous 1N HCl was added until pH=5, and the aq. phase was extracted with EtOAc. Drying over $Na_2SO_4$, filtration and evaporation under reduced pressure afforded the title compound that was used in the following step without further purification. MS ($ES^+$) m/z 250 $(M+H)^+$.

Step 3: methyl N-(2,2-difluorohept-6-en-1-yl)-L-valyl-(4R)-4-{[(4-vinyl-13-dihydro-2H-isoindol-2-yl)carbonyl]oxy}-L-prolinate 75 i-$Pr_2EtN$ (2.2 eq.) followed by TBTU (1.2 eq.) was added to a stirred mixture of N-(2,2-difluorohept-6-en-1-yl)-L-valine 74 and (2S,4R)-2-(methoxycarbonyl)-4-{[(4-vinyl-1,3- dihydro-2H-isoindol-2-yl)carbonyl]oxy}pyrrolidinium chloride (1 eq.) in CH₂Cl₂ (0.06 M) and the mixture was stirred at RT overnight. Sat. aq. NaHCO₃ was added, the organic layer was separated and dried (Na₂SO₄). Evaporation under reduced pressure afforded a residue, which was purified by flash chromatography on silica gel (EtOAc:PE=1:9). The title compound was obtained as a yellow foam (39%). MS (ES⁺) m/z 548 (M+H)⁺.

Step 4: Methyl (5R,7S,10S,17Z)-13,13-difluoro-10-isopropyl-3,9-dioxo-6,7,9,10,11,12,13,14,15,16-decahydro-1H,5H-2, 22:5,8-dimethano-4,2,8,11-benzoxatriazacycloicosine-7-carboxylate 76

Zhan catalyst I (0.2 eq.) was added to methyl N-(2,2-difluorohept-6-en-1-yl)-L-valyl-(4R)-4-{[(4-vinyl-1,3-dihydro-2H-isoindol-2-yl)carbonyl]oxy}-L-prolinate 75 in CH₂Cl₂ (0.02 M) and the mixture was heated under microwave irradiation at 100° C. for 15 min. Volatiles were evaporated under reduced pressure affording a residue, which was purified by flash chromatography on silica gel (EtOAc:PE=2: 8). The title compound was obtained as a yellow foam (66%). MS (ES⁺) m/z 520 (M+H)⁺.

Step 5: methyl-(5R,7S,10S)-13,13-difluoro-10-isopropyl-3,9-dioxo-6,7,9,10,11,12,13,14,15,16,17,18-dodecahydro-1H,5H-2, 22:5,8-dimethano-4,2,8,11-benzoxatriazacycloicosine-7-carboxylate 77

Palladium on carbon (10% Pd, 20% weight) and methyl (5R,7S,10S,17Z)-13,13-difluoro-10-isopropyl-3,9-dioxo-6,7,9,10,11,12,13,14,15,16-decahydro-1H,5H-2, 22:5,8-dimethano-4,2,8,11-benzoxatriazacycloicosine-7-carboxylate 76 in MeOH (0.02M) were stirred under a hydrogen atmosphere. After 4 h solids were filtered on CELITE and the resulting solution was evaporated under reduced pressure affording the title compound as a pale brown oil. MS (ES⁺) m/z 522 (M+H)⁺.

Step 6: (5R,7S,10S)-13,13-difluoro-10-isopropyl-3,9-dioxo-6,7,9,10,11,12,13,14,15,16,17,18-dodecahydro-1H,5H-2, 22:5,8-dimethano-4,2,8,11-benzoxatriazacycloicosine-7-carboxylic acid 79

Lithium hydroxide monohydrate (3 eq.) was added to a stirred mixture of methyl (5R,7S,10S)-13,13-difluoro-10-isopropyl-3,9-dioxo-6,7,9,10,11,12,13,14,15,16,17,18-dodecahydro-1H,5H-2, 22:5,8-dimethano-4,2,8,11-benzoxatriazacycloicosine-7-carboxylate 77 in THF and water (2/1 v/v, 0.02 M) and the mixture was stirred at RT overnight. Aqueous HCl (1N) was added to reach pH=5 and the mixture was extracted with EtOAc. The organic layer was separated, dried over Na₂SO₄, filtered and concentrated to obtain the crude product which was used in the following step without further purification. MS (ES⁺) m/z 508 (M+H)⁺.

Step 7: (5R,7S,10S)-N-((1R,2S)-1-{[(cyclopropylsulfonyl)amino]carbonyl}-2-vinylcyclopropyl)-13,13-difluoro-10-isopropyl-3,9-dioxo-6,7,9,10,11,12,13,14,15,16,17,18-dodecahydro-1H,5H-2, 22:5,8-dimethano-4,2,8,11-benzoxatriazacycloicosine-7-carboxamide 14 i-Pr₂EtN (6.5 eq.), DMAP (0.5 eq.) and TBTU (1.3 eq.) were added to a stirred mixture of (5R,7S,10S)-13,13-difluoro-10-isopropyl-3,9-dioxo-6,7,9,10,11,12,13,14,15,16,17,18-dodecahydro-1H,5H-2, 22:5,8-dimethano-4,2,8,11-benzoxatriazacycloicosine-7-carboxylic acid 78 and (1R,2S)-1-{[(cyclopropylsulfonyl)amino]carbonyl}-2-vinylcyclopropanaminium chloride (prepared as described in WO 03/099274) (1.5 eq.) 48 (1.5 eq.) in CH₂Cl₂ (0.02 M) and the mixture was stirred at RT. After 13 h, the mixture was evaporated under reduced pressure affording a residue, which was redissolved in DMSO and purified by RP-HPLC (stationary phase: column SYMMETRY C18, 7 µm, 19×300 mm. Mobile phase: MeCN/H₂O buffered with 0.1% TFA). Fractions containing the pure compound were combined and freeze dried to afford the title compound 14 as a white powder (15% over three steps). ¹H NMR (400 MHz, DMSO-d₆, 300 K) δ 10.66 (s, 1H), 8.97 (br s, 1H), 7.25 (t, J 7.5, 1H), 7.17 (d, J 7.3, 1H), 7.13 (d, J 7.6, 1H), 5.61 (dt, J 17.3, 9.5, 1H), 5.38 (br s, 1H), 5.25 (d, J 16.9, 1H), 5.11 (d, J 11.4, 1H), 4.73-4.54 (m, 4H), 4.45 (dd, J 10.1, 7.3, 1H), 4.04 (d, J 12.1, 1H), 3.75 (dd, J 12.0, 3.2, 1H), 3.50-3.02 (m, 3H), 2.96-2.85 (m, 1H), 2.45-2.34 (partially obscured by residual DMSO, 3H), 2.24-1.67 (m, 6H), 1.66-1.48 (m, 2H), 1.49-1.20 (m, 5H), 1.14-0.91 (m, 10H). MS (ES⁺) m/z 720 (M+H)⁺.

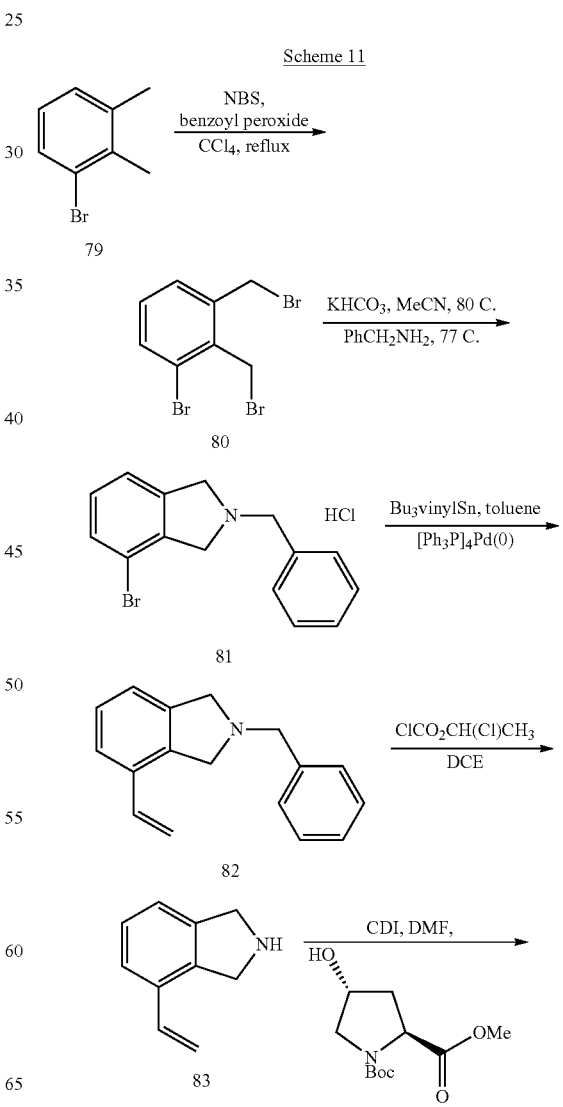

Scheme 11

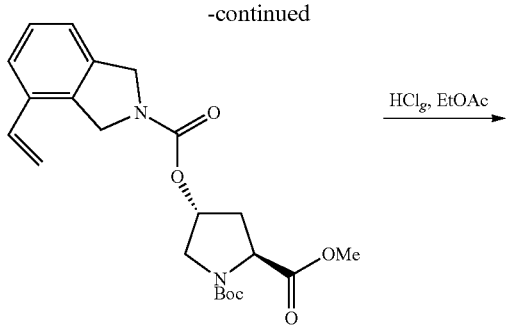

84

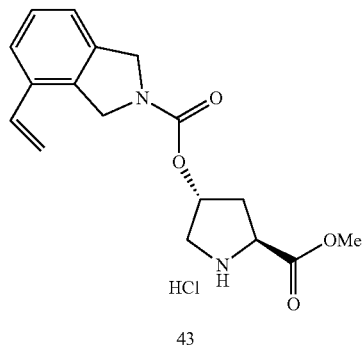

43

Compound 43: (3R,5S)-5-(methoxycarbonyl)pyrrolidin-3-yl-4-vinyl-1,3-dihydro-2H-isoindole-2-carboxylate hydrochloride Step 1: 1-bromo-2,3-bis(bromomethyl)benzene 80

A suspension of 3-bromo-o-xylene (1.0 eq.), N-bromosuccinimide (2.15 eq.) and benzoyl peroxide (1.0 eq.) in $CCl_4$ (0.55 M) was heated to reflux under nitrogen for 15 h. The contents of the reaction flask were cooled, filtered, and the filtrate evaporated. The crude material was distilled under high vacuum. Major fractions were distilled between 88° C. and 152° C. Pure material was recovered in 85% yield. $^1$H NMR ($CDCl_3$) δ (ppm) 7.56 (d, J 8.0, 1H), 7.31 (d, J 8.0, 1H), 7.26 (s, 1H), 7.16 (t, J 8.0, 1H), 4.84 (s, 2H), 4.64 (s, 2H).

Step 2: 2-benzyl-4-bromoisoindoline 81

Potassium bicarbonate (2.5 eq.) was suspended in MeCN (0.17 M) and the mixture was heated to 80° C. Solutions of 1-bromo-2,3-bis(bromomethyl)benzene 80 (1.0 eq.) in MeCN (1.64 M) and benzylamine (1.0 eq.) in MeCN (1.64 M) were added concurrently via addition funnels over 1 h. The reaction mixture was stirred at 77° C. for 16 h. The contents of the reaction flask were cooled, filtered and the solvent removed by evaporation. The reaction was partitioned between 1 M $K_2CO_3$ and EtOAc. The organics were washed with brine, dried with anhydrous $Na_2SO_4$, filtered, and evaporated. Flash column chromatography (gradient elution: heptane to 10% EtOAc in heptane) gave after evaporation the title compound 81 as a pale oil. $^1$H NMR ($CDCl_3$) δ (ppm) 7.41-7.39 (m, 2H), 7.37-7.34 (m, 2H), 7.32-7.27 (m, 2H), 7.10-7.03 (m, 2H), 4.02 (s, 2H), 3.97 (s, 2H), 3.91 (s, 2H). LRMS (ESI) m/z 289 (M+H)$^+$.

Converted to HCl salt in HCl/MeOH by adding MTBE and filtering solid to give the corresponding HCl salt.

Step 3: 2-benzyl-4-vinylisoindoline 82

A solution of 2-benzyl-4-bromoisoindoline 81 (1.0 eq.) and tributyl(vinyl)tin (1.2 eq.) in toluene (4 M) was degassed by bubbling nitrogen gas through the solution for 0.25 h. Tetrakis(triphenylphosphine)palladium(0) (0.02 eq.) was added and the resulting solution heated in a 100° C. oil bath under nitrogen for 24 h. The contents of the reaction flask were cooled, evaporated and subjected to flash column chromatography eluting with hexane/EtOAc 95/5 to give after evaporation the title compound as a pale oil that turned pink on standing. LRMS (ESI) m/z 236 (M+H)$^+$.

Step 4: 4-vinylisoindoline 83

A solution of 2-benzyl-4-vinylisoindoline 82 (1.0 eq.) in DCE (0.38 M) was placed in a round bottom flask under nitrogen. To this was attached an addition funnel containing a solution of 1-chloroethyl chloroformate (1.2 eq.) in DCE. The reaction flask was cooled in an ice bath and the contents of the addition funnel were added dropwise over 20 min keeping the internal reaction temperature <5° C. After the addition was complete the reaction flask was allowed to warm to RT then heated to reflux for 45 min. The contents of the reaction flask were cooled to RT then the solvent removed by evaporation. MeOH was added and the contents of the reaction flask were heated to reflux for 30 min. The reaction flask was cooled and the solvent removed by evaporation. Water was added and the resulting mixture washed with EtOAc. The aqueous layer was made basic with 2N sodium hydroxide then extracted with DCM (4×250 mL). The combined organic extracts were dried with anhydrous sodium sulfate, filtered and the filtrate evaporated. The remaining residue was subjected to flash column chromatography eluting with DCM/MeOH/ammonium hydroxide 97/3/0.3 to 95/5/0.5. Evaporation of fractions gave the title compound 83 as a brown oil, (71% for two steps). LRMS (ESI) m/z 146 (M+H)$^+$.

Step 5: 1-tert-butyl 2-methyl (2S,4R)-4-{[(4-vinyl-1,3-dihydro-2H-isoindol-2-yl)carbonyl]oxy}pyrrolidine-1,2-dicarboxylate 84

A solution of 1-tert-butyl 2-methyl (2S,4R)-4-hydroxypyrrolidine-1,2-dicarboxylate (1.0 eq.) in DMF (0.5 M) under nitrogen was cooled to 0° C. Solid 1,1'-carbonyldiimidazole (1.0 eq.) was added to the reaction. The contents of the reaction flask were warmed to RT and after 2 h a solution of 4-vinylisoindoline (1.0 eq.) in DMF (4 M) was added. The reaction was heated in a 60° C. oil bath for 2 h then cooled and poured into water and 5% potassium bisulfate. The resulting mixture was extracted with EtOAc. Combined organics were washed with brine, dried with anhydrous sodium sulfate, filtered and evaporated. Flash column chromatography eluting with hexane/EtOAc 70/30 gave the title compound as a white foam (81%). LRMS (ESI) m/z 417 (M+H).

Scheme 12

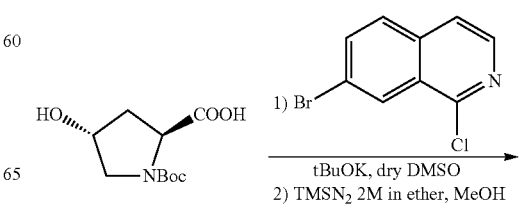

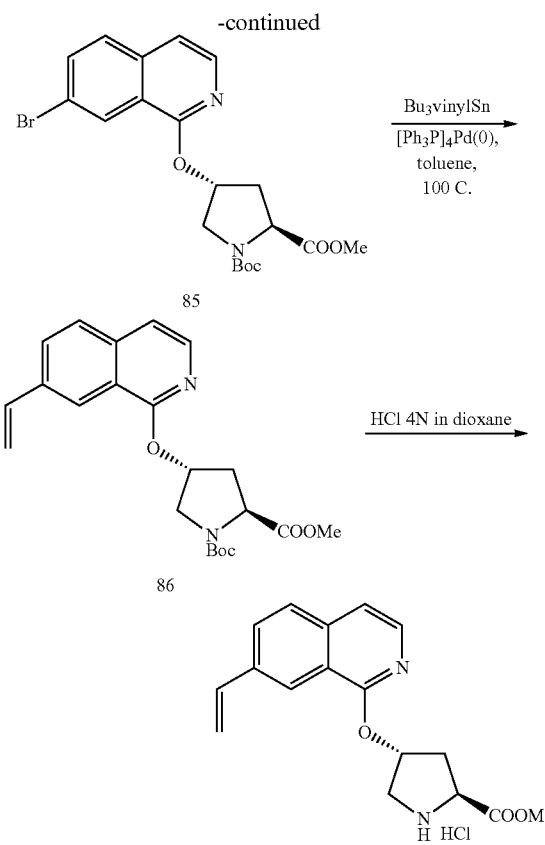

Compound 50: (2S,4R)-2-(methoxycarbonyl)-4-[(7-vinylisoquinolin-1-yl)oxy]pyrrolidinium chloride Step 1: 1-tert-butyl 2-methyl (2S,4R)-4-[(7-bromoisoquinolin-1-yl)oxy]pyrrolidine-1,2-dicarboxylate 85

To a solution of trans 4-hydroxy L-BOC-proline (1 eq) in DMSO (0.2 M) at RT was added 'BuOK (3 eq) in a single portion. The reaction mixture was stirred at RT for 30 min, cooled to 10° C. and 7-bromo-1-chloroisoquinoline was added (1 eq). The resulting mixture was allowed to warm to RT and stirred overnight. The organic layer was washed with citric acid 10% solution, water and brine and the aqueous phases were back extracted with EtOAc. The combined organic phases were dried ($Na_2SO_4$) and the solvent evaporated under reduced pressure to give a dark solid that was dissolved in MeOH. To the stirred solution, trimethylsilyldiazomethane 2.0 M in hexanes (4.0 eq.) was added dropwise at 15° C. The resulting mixture was stirred for 15 min after gas evolution has ceased. Volatiles were removed by rotary evaporation and the residue was purified by flash chromatography (HORIZON system, column $SiO_2$, eluent: PE:EtOAc with EtOAc (from 60 to 80%) to give the title product 85 as a solid (71%). MS (ES$^+$) m/z 452 (M+H$^+$).

Step 2: 1-tert-butyl 2-methyl (2S,4R)-4-[(7-vinylisoquinolin-1-yl)oxy]pyrrolidine-12-dicarboxylate 86

Aryl bromide 85 (1.0 eq.) was dissolved in toluene (0.2 M) and treated with tributylvinyltin (1.5 eq) and [$Ph_3P$]$_4$Pd(0) (0.1 eq). The reaction mixture was stirred at 80° C. under $N_2$ atmosphere for 2 h. After cooling to RT, the reaction mixture was poured into EtOAc and washed with brine. The organic phase was separated, dried ($Na_2SO_4$) and concentrated under reduced pressure. The residue was purified by flash chromatography (HORIZON system, column $SiO_2$, eluent: PE:EtOAc with EtOAc from 20 to 40%) to give the title compound 86 as a viscous oil (74%). MS (ES$^+$) m/z 399 (M+H$^+$).

Step 3: (2S,4R)-2-(methoxycarbonyl)-4-[(7-vinylisoquinolin-1-yl)oxy]pyrrolidinium chloride 50

Carbamate 86 was dissolved in a 4.0 M HCl solution in dioxane. The resulting mixture was stirred at RT for 0.5 h, during which time the product precipitated. The title compound 50 was filtered off and washed with hexane/EtOAc 1/1 v/v (96%). $^1$H NMR (400 MHz, DMSO-d$_6$, 300 K) δ 8.30 (s, 1H), 8.01-7.98 (m, 2H), 7.89 (d, J 8.5, 1H), 7.43 (d, J 5.8, 1H), 6.93 (dd, J 17.6, 10.9, 1H), 6.07 (d, J 17.6, 1H), 5.85 (bs, 1H), 5.43 (d, J 11.0, 1H), 4.86 (dd, J 10.4, 7.7, 1H), 3.81 (s, 3H), 3.78-3.74 (m, 1H), 3.60 (d, J 12.8, 1H), 2.71-2.66 (m, 1H), 2.57-2.50 (m, partially obscured by residual DMSO, 1H). MS (ES$^+$) m/z 299 (M+H$^+$).

Scheme 13

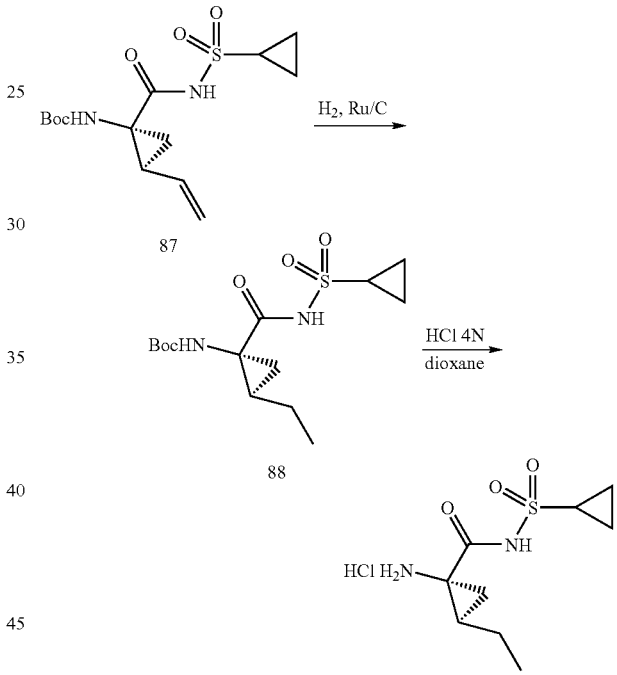

Compound 49: (1R,2S)-1-amino-N-(cyclopropylsulfonyl)amino-2-ethylcyclopropane carboxamide hydrochloride Step 1: tert-butyl ((1R,2R)-1-{[(cyclopropylsulfonyl)amino]carbonyl}-2-ethylcyclopropyl)carbamate 88

A hydrogenation vessel was charged with a solution of tert-butyl ((1R,2S)-1-{[(cyclopropylsulfonyl)amino]carbonyl}-2-vinylcyclopropyl)carbamate 87 (prepared as described in WO 03/099274) in MeOH followed by Ru/C (7.5 wt %). The vessel was placed under $N_2$ (20 psig) and vented to atmospheric pressure three times to remove residual oxygen. The vessel was then placed under $H_2$ (50 psig) and the reaction was complete in <5 h based on $H_2$ consumption. After 20 h, the vessel was vented to atmospheric pressure. The reaction slurry was then filtered and evaporated to a yellow oil which was brought to the following step without further purification. MS (ES$^+$) m/z 333 (M+H$^+$).

Step 2: (1R,2S)-1-amino-N-(cyclopropylsulfonyl) amino-2-ethylcyclopropane carboxamide hydrochloride 49
A 0.33 M solution of carbamate in 4N HCl/dioxane was stirred at RT for 12 h. The volatiles were then removed under reduced pressure to give the title compound 49 as a pale yellow solid that was used directly in the next step. $^1$H NMR (300 MHz, DMSO-$d_6$) δ 8.83 (bs, 2H), 3.03 (m, 1H), 1.71-1.37 (m, 5H), 1.16-1.09 (m, 4H), 0.97 (t, J 7.3, 3H).
Scheme 14
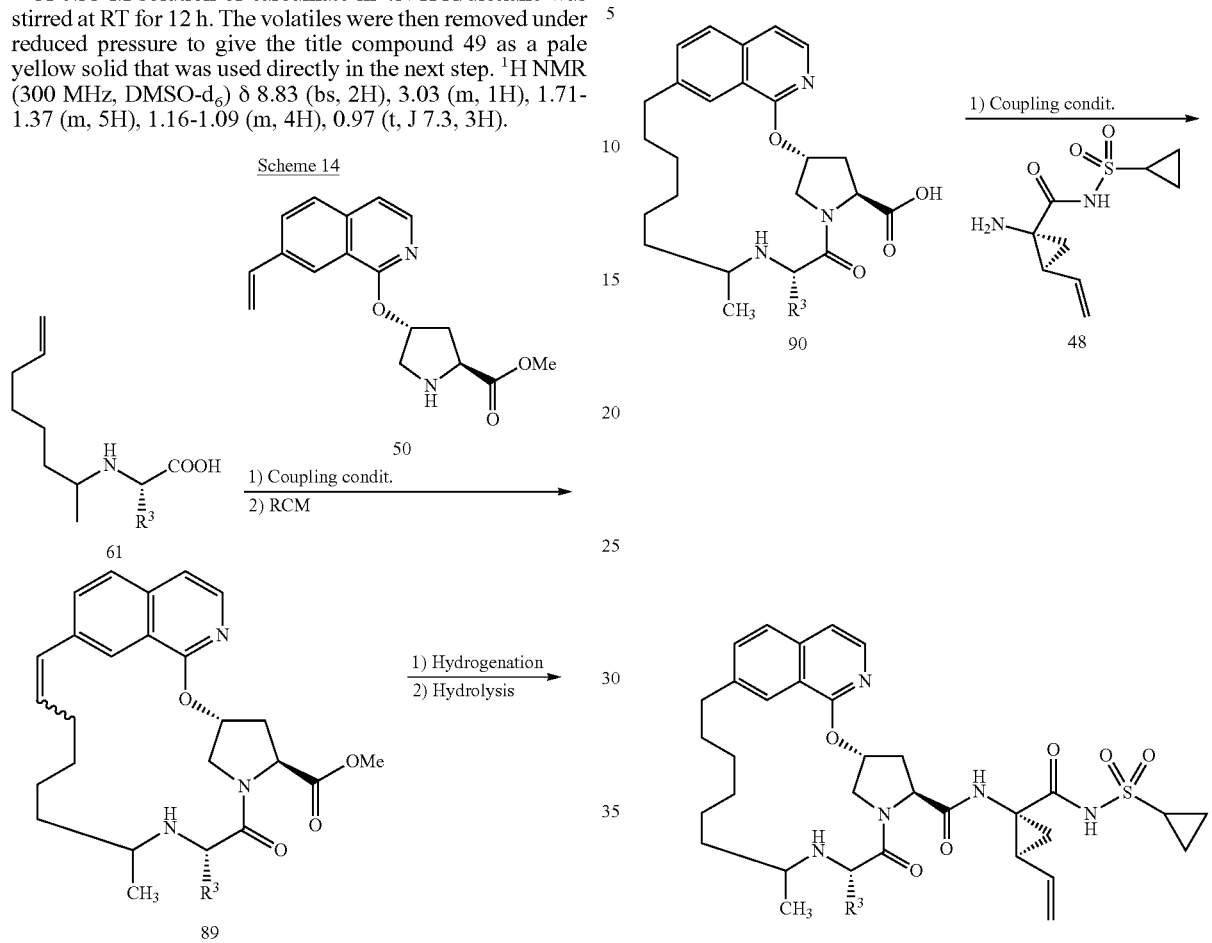
Scheme 15
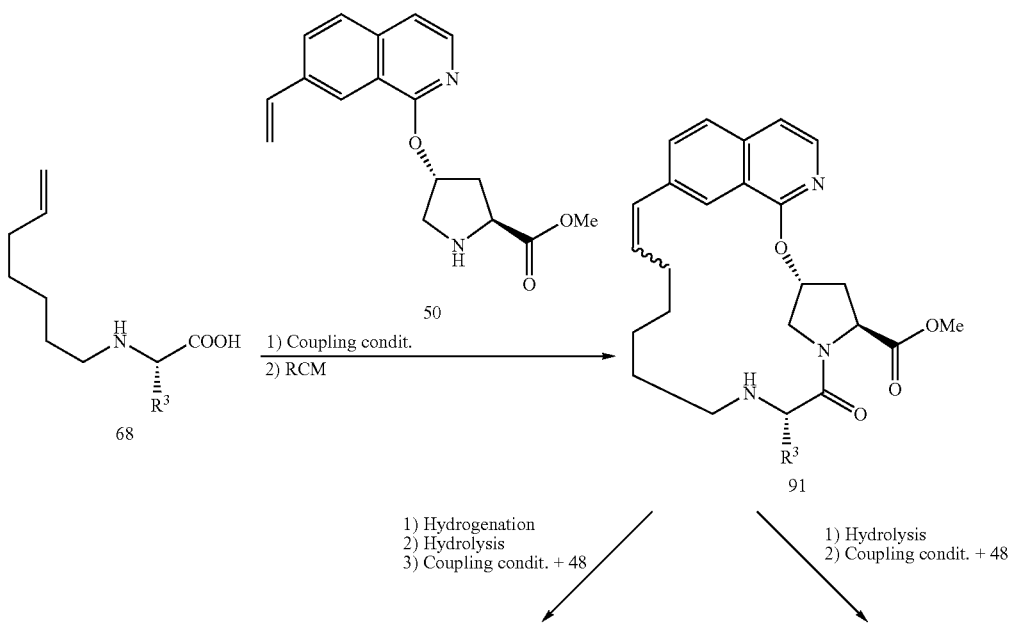

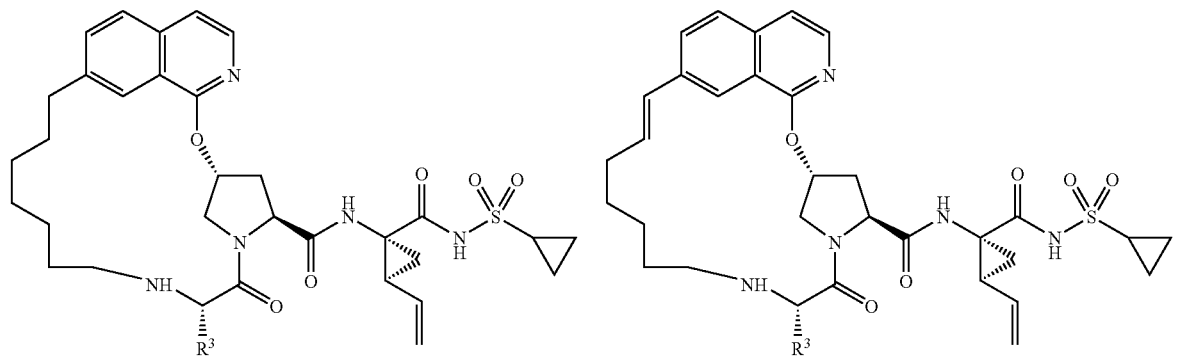
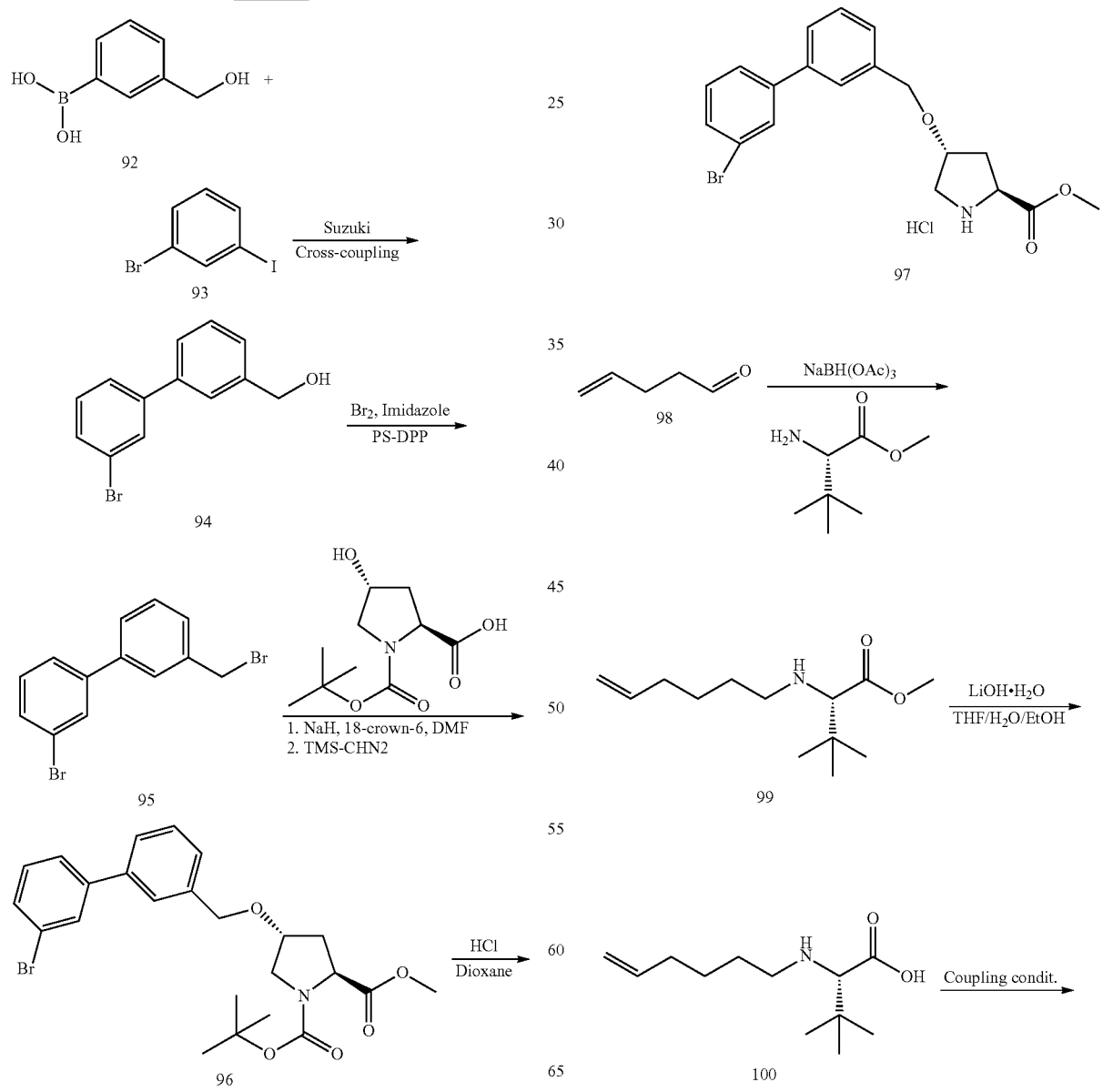
Scheme 16

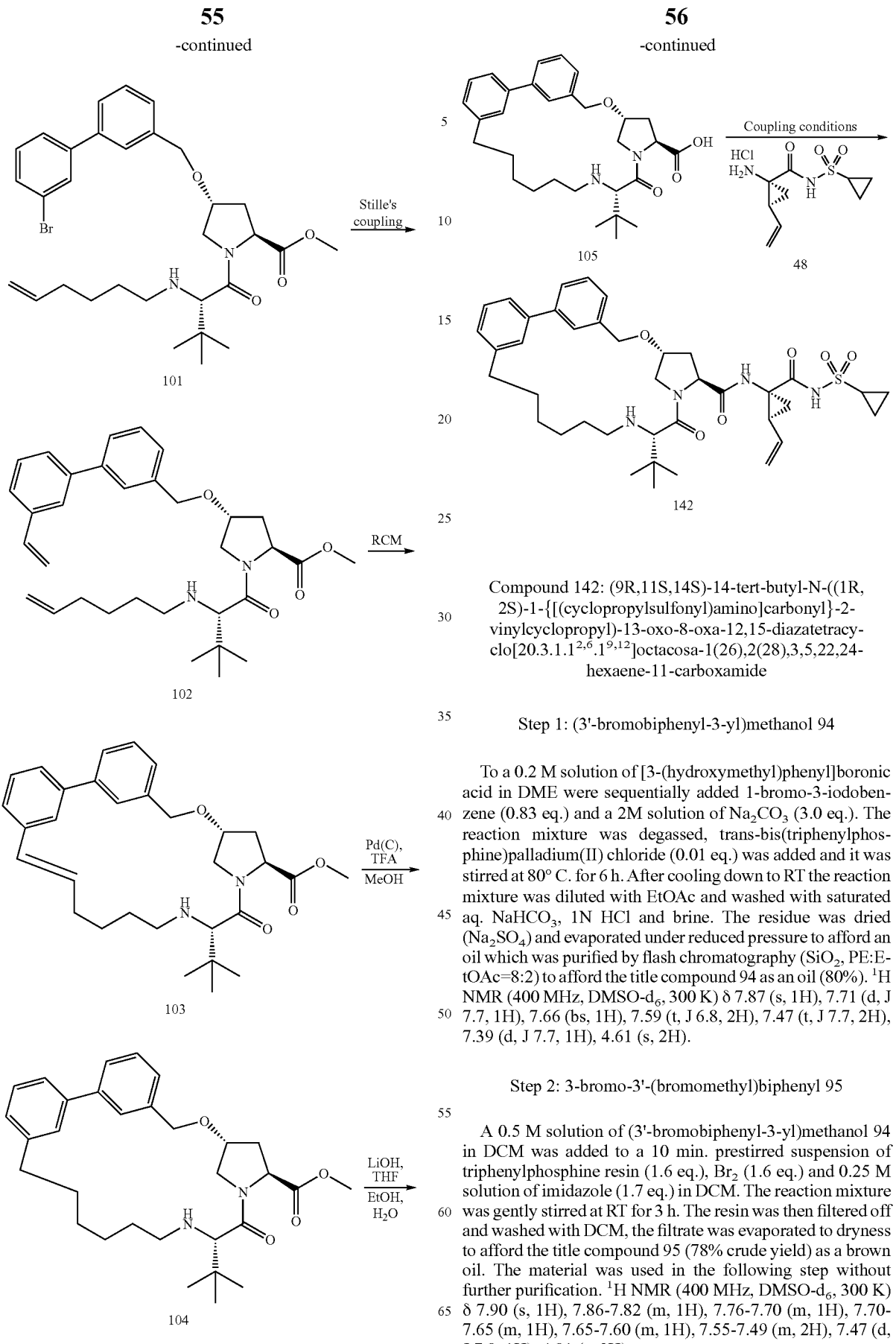

Compound 142: (9R,11S,14S)-14-tert-butyl-N-((1R,2S)-1-{[(cyclopropylsulfonyl)amino]carbonyl}-2-vinylcyclopropyl)-13-oxo-8-oxa-12,15-diazatetracyclo[20.3.1.1$^{2,6}$.1$^{9,12}$]octacosa-1(26),2(28),3,5,22,24-hexaene-11-carboxamide Step 1: (3'-bromobiphenyl-3-yl)methanol 94

To a 0.2 M solution of [3-(hydroxymethyl)phenyl]boronic acid in DME were sequentially added 1-bromo-3-iodobenzene (0.83 eq.) and a 2M solution of Na$_2$CO$_3$ (3.0 eq.). The reaction mixture was degassed, trans-bis(triphenylphosphine)palladium(II) chloride (0.01 eq.) was added and it was stirred at 80° C. for 6 h. After cooling down to RT the reaction mixture was diluted with EtOAc and washed with saturated aq. NaHCO$_3$, 1N HCl and brine. The residue was dried (Na$_2$SO$_4$) and evaporated under reduced pressure to afford an oil which was purified by flash chromatography (SiO$_2$, PE:EtOAc=8:2) to afford the title compound 94 as an oil (80%). $^1$H NMR (400 MHz, DMSO-d$_6$, 300 K) δ 7.87 (s, 1H), 7.71 (d, J 7.7, 1H), 7.66 (bs, 1H), 7.59 (t, J 6.8, 2H), 7.47 (t, J 7.7, 2H), 7.39 (d, J 7.7, 1H), 4.61 (s, 2H).

Step 2: 3-bromo-3'-(bromomethyl)biphenyl 95

A 0.5 M solution of (3'-bromobiphenyl-3-yl)methanol 94 in DCM was added to a 10 min. prestirred suspension of triphenylphosphine resin (1.6 eq.), Br$_2$ (1.6 eq.) and 0.25 M solution of imidazole (1.7 eq.) in DCM. The reaction mixture was gently stirred at RT for 3 h. The resin was then filtered off and washed with DCM, the filtrate was evaporated to dryness to afford the title compound 95 (78% crude yield) as a brown oil. The material was used in the following step without further purification. $^1$H NMR (400 MHz, DMSO-d$_6$, 300 K) δ 7.90 (s, 1H), 7.86-7.82 (m, 1H), 7.76-7.70 (m, 1H), 7.70-7.65 (m, 1H), 7.65-7.60 (m, 1H), 7.55-7.49 (m, 2H), 7.47 (d, J 7.8, 1H), 4.81 (s, 2H).

Step 3: 1-tert-butyl 2-methyl (2S,4R)-4-[(3'-bromo-biphenyl-3-yl)methoxy]pyrrolidine-1,2-dicarboxylate 96

(4R)-1-(tert-butoxycarbonyl)-4-hydroxy-L-proline (1.0 eq.) in DMF was added to a 0° C. cooled suspension of 18-crown-6 (0.1 eq.) and NaH (3.0 eq.) in DMF (0.5 M final concentration). The reaction mixture was allowed to warm up to RT and stirred for 1 h. A 0.5M solution of 3-bromo-3'-(bromomethyl)biphenyl 95 (1.0 eq.) in DMF was added dropwise and the reaction mixture was stirred at RT overnight. The reaction mixture was quenched with aqueous HCl (1N) at 0° C. and diluted with EtOAc. The organic layer was separated, washed with aqueous HCl (1N) and brine, dried (Na$_2$SO$_4$) and evaporated to a solid. MS (ES$^+$) m/z 498, 500 (M+Na)$^+$. A 0.5 M solution of the crude material in a mixture of toluene:MeOH (2:1) was cooled to 0° C. and treated dropwise with TMS-diazomethane (1.5 eq.). The reaction mixture was allowed to warm up to RT and stirred for 1 h. The solvents were evaporated under reduced pressure and the residue was purified by flash chromatography (SiO$_2$, PE:EtOAc=8:2) to afford the title compound 96 as a yellow oil (78%). $^1$H NMR (400 MHz, DMSO-d$_6$, 300 K) δ 7.90-7.86 (m, 1H), 7.71 (d, J 7.7, 1H), 7.69-7.58 (m, 3H), 7.54-7.44 (m, 2H), 7.40 (d, J 7.7, 1H), 4.66-4.55 (m, 2H), 4.31-4.21 (m, 2H), 3.74-3.65 (m, 3H), 3.60-3.45 (m, 2H), 2.51-2.37 (m, 1H), 2.10-2.00 (m, 1H), 1.44-1.31 (m, 9H). MS (ES$^+$) m/z 512, 514 (M+Na)$^+$.

Step 4: (2S,4R)-4-[(3'-bromobiphenyl-3-yl)methoxy]-2-(methoxycarbonyl)pyrrolidinium chloride 97

1-tert-Butyl 2-methyl (2S,4R)-4-[(3'-bromobiphenyl-3-yl)methoxy]pyrrolidine-1,2-dicarboxylate 96 (1.0 eq.) was dissolved at 0° C. in a 4M solution of HCl in dioxane (3.0 eq.) to give a 1.0 M solution. The reaction mixture was stirred at RT for 2 h then the solvent was evaporated under reduced pressure to afford the title compound 97 as a white foam (96%). $^1$H NMR (400 MHz, DMSO-d$_6$, 300 K) δ 10.33-9.33 (bs, 1H), 7.89 (s, 1H), 7.77-7.71 (m, 2H), 7.67 (d, J 7.7, 1H), 7.62 (d, J 7.7, 1H), 7.54-7.43 (m, 3H), 4.63 (s, 2H), 4.55 (dd, J 10.7, 7.4 Hz, 1H), 4.41 (bs, 1H), 3.81 (s, 3H), 3.51-3.40 (m, 2H), 2.59-2.51 (m, 1H), 2.27-2.16 (m, 1H). MS (ES) m/z 390, 392 (M+H)$^+$.

Step 5: methyl N-hex-5-en-1-yl-3-methyl-L-valinate 99

Hex-5-enal 98 (obtained from hex-5-en-1-ol via a PCC oxidation) (0.95 eq.) was added at RT to a 0.11 M solution of (2S)-1-methoxy-3,3-dimethyl-1-oxobutan-2-aminium chloride (1.0 eq.) and TEA (1.0 eq.) in DCE. Sodium triacetoxyborohydride (1.0 eq.) was added in one portion and the reaction mixture was stirred at RT overnight. The reaction mixture was diluted with DCM/saturated aqueous NaHCO$_3$. The phases were separated; the organic layer was washed with brine, dried (Na$_2$SO$_4$) and filtered though a short path of silica gel (PE:EtOAc=9:1) to afford the title compound 99 as a pale yellow liquid (72%). $^1$H NMR (300 MHz, CDCl$_3$, 300 K) δ 5.89-5.71 (m, 1H), 5.07-4.88 (m, 2H), 3.71 (s, 3H), 2.88 (s, 1H), 2.62-2.48 (m, 1H), 2.45-2.31 (m, 1H), 2.13-1.98 (m, 2H), 1.67-1.54 (m, 1H), 1.53-1.35 (m, 4H), 0.95 (s, 9H).

Step 6: N-hex-5-en-1-yl-3-methyl-L-valine 100

A 0.25M solution of methyl N-hex-5-en-1-yl-3-methyl-L-valinate 99 in a mixture of MeOH:water (3:1) was treated with LiOH (3.0 eq.) at RT. The reaction mixture was stirred at 70° C. for 3 h. The organic solvent was removed under reduced pressure and the residue was acidified with aqueous HCl (1N). The water phase was repeatedly extracted with EtOAc, dried (Na$_2$SO$_4$) and concentrated under reduced pressure to afford the crude product, which was used in the following step without further purification. MS (ES$^+$) m/z 214 (M+H)$^+$

Step 7: methyl N-hex-5-en-1-yl-3-methyl-L-valyl-(4R)-4-[(3'-bromobiphenyl-3-yl)methoxy]-L-prolinate 101

N-hex-5-en-1-yl-3-methyl-L-valine (1.2 eq.), DIPEA (3.7 eq.) and HATU (1.2 eq.) were sequentially added to a 0.10 M solution of (2S,4R)-4-[(3'-bromobiphenyl-3-yl)methoxy]-2-(methoxycarbonyl)pyrrolidinium chloride in DMF. The reaction mixture was stirred at RT overnight then it was diluted with H$_2$O/EtOAc and extracted. The collected organic layers were washed with brine, dried (Na$_2$SO$_4$) and evaporated under reduced pressure. The residue was purified by flash chromatography (SiO$_2$, PE:EtOAc with EtOAc from 30 to 100%) to afford the title compound 101 as a solid (50%). $^1$H NMR (400 MHz, DMSO-d$_6$, 300 K) δ 7.85 (bs, 1H), 7.69 (d, J 7.8, 1H), 7.66-7.58 (m, 3H), 7.51-7.43 (m, 2H), 7.37 (d, J 7.8, 1H), 5.76-5.64 (m, 1H), 4.97-4.87 (m, 2H), 4.63 (s, 2H), 4.45 (t, J 8.6, 1H), 4.31 (bs, 1H), 4.07 (d, J 11.7, 1H), 3.66 (s, 3H), 3.73-3.55 (m, 2H), 2.50-2.41 (m, 1H), 2.40-2.32 (m, 1H), 2.31-2.23 (m, 1H), 2.08-1.96 (m, 1H), 1.94-1.85 (m, 2H), 1.34-1.18 (m, 3H), 0.96 (s, 9H), 0.94-0.85 (m, 2H). MS (ES$^+$) m/z 585, 587 (M+H)$^+$.

Step 8: methyl N-hex-5-en-1-yl-3-methyl-L-valyl-(4R)-4-[(3'-vinylbiphenyl-3-yl)methoxy]-L-prolinate 102

Vinyltri-n-butyltin (1.5 eq.) was added to a 0.08 M degassed solution of methyl N-hex-5-en-1-yl-3-methyl-L-valyl-(4R)-4-[(3'-bromobiphenyl-3-yl)methoxy]-L-prolinate 101 in toluene. Tetrakis (triphenylphosphine) palladium (0) (0.15 eq.) was added and the reaction mixture was stirred in a preheated oil bath (100° C.) for 2 h. The crude mixture was cooled down to RT and evaporated under reduced pressure to give a residue that was purified by flash chromatography (SiO$_2$, PE:EtOAc=7:3) to afford the title compound 102 as a yellow oil (38%). $^1$H NMR (400 MHz, DMSO-d$_6$, 300K) δ 7.74 (bs, 1H), 7.69-7.60 (m, 2H), 7.57 (d, J 7.7, 1H), 7.52 (t, J 7.7, 1H), 7.50-7.44 (m, 2H), 7.34 (d, J 7.7, 1H), 6.86 (dd, J 17.7, 10.9, 1H), 5.97 (d, J 17.7, 1H), 5.76-5.64 (m, 1H), 5.36 (d, J 10.9, 1H), 4.97-4.86 (m, 2H), 4.63 (s, 2H), 4.46 (t, J 8.6, 1H), 4.31 (bs, 1H), 3.74-3.55 (m, 2H), 3.66 (s, 3H), 2.50-2.41 (m, 1H), 2.40-2.31 (m, 1H), 2.31-2.23 (m, 1H), 1.94-1.85 (m, 2H), 1.70-1.53 (m, 3H), 1.41-1.30 (m, 4H), 1.00-0.85 (m, 8H), 0.96 (s, 9H). MS (ES$^+$) m/z 533 (M+H)$^+$

Step 9: Methyl (9R,11S,14S,20E)-14-tert-butyl-13-oxo-8-oxa-12,15-diazatetracyclo[20.3.1.1$^{2,6}$.1$^{9,12}$]octacosa-1(26),2(28),3,5,20,22,24-heptaene-11-carboxylate 103

Zhan catalyst I (0.15 eq.) was added to a 0.01 M solution of methyl N-hex-5-en-1-yl-3-methyl-L-valyl-(4R)-4-[(3'-vinylbiphenyl-3-yl)methoxy]-L-prolinate 102 in DCM containing trifluoroacetic acid (1.3 eq.). The reaction mixture was stirred under microwave irradiation at 100° C. for 20 min. The crude material was evaporated under reduced pressure affording a black residue which was used without further purification. MS (ES+) m/z 505 (M+H)+.

Step 10: methyl (9R,11S,14S)-14-tert-butyl-13-oxo-8-oxa-12,15-diazatetracyclo[20.3.1.1$^{2,6}$.1$^{9,12}$]octacosa-1(26),2(28),3,5,22,24-hexaene-11-carboxylate 104

Pd/C 10% (20% w/w) was added to a 0.025 M solution of methyl (9R,11S,14S,20E)-14-tert-butyl-13-oxo-8-oxa-12,15-diazatetracyclo[20.3.1.1$^{2,6}$.1$^{9,12}$]octacosa-1(26),2(28),3,5,20,22,24-heptaene-11-carboxylate 103 in MeOH containing trifluoroacetic acid (1.0 eq.). The reaction mixture was stirred under a hydrogen atmosphere for 6 h. Solids were filtered off and the resulting solution was evaporated under reduced pressure. The residue was used without further purification in the following step. MS (ES+) m/z 507 (M+H)+.

Step 11: (9R,11S,14S)-14-tert-butyl-13-oxo-8-oxa-12,15-diazatetracyclo[20.3.1.1$^{2,6}$.1$^{9,12}$]octacosa-1(26),2(28),3,5,22,24-hexaene-11-carboxylic acid 105

LiOH (3.0 eq.) was added to a 0.05 M solution of methyl (9R,11S,14S)-14-tert-butyl-13-oxo-8-oxa-12,15-diazatetracyclo[20.3.1.1$^{2,6}$.1$^{9,12}$]octacosa-1(26),2(28),3,5,22,24-hexaene-11-carboxylate 104 in a mixture of THF:EtOH:H$_2$O (2:1:1). The reaction mixture was stirred at 40° C. for 2 h then the solvent was evaporated under reduced pressure. Aqueous HCl (1N) was added to reach pH=6 and the mixture was evaporated to dryness to yield a dark solid which was used without further purification. MS (ES+) m/z 493 (M+H)+.

Step 12: (9R,11S, 14S)-14-tert-butyl-N-((1R,2S)-1-{[(cyclopropylsulfonyl)amino]carbonyl}-2-vinyl-cyclopropyl)-13-oxo-8-oxa-12,15-diazatetracyclo[20.3.1.1$^{2,6}$.1$^{9,12}$]octacosa-1(26),2(28),3,5,22,24-hexaene-11-carboxamide 142

(1R,2S)-1-{[(cyclopropylsulfonyl)amino]carbonyl}-2-vinylcyclopropanaminium chloride 48 (prepared as described in WO 03/099274) (1.2 eq.) and HATU (1.2 eq.) were added to a 0.1M solution of (9R,11S,14S)-14-tert-butyl-13-oxo-8-oxa-12,15-diazatetracyclo[20.3.1.1$^{2,6}$.1$^{9,12}$]octacosa-1(26),2(28),3,5,22,24-hexaene-11-carboxylic acid 105 in DMF containing DIPEA (4.0 eq.). The reaction mixture was stirred at RT overnight. The reaction mixture was concentrated to dryness, dissolved in DMSO and purified by RP-HPLC (stationary phase: column WATERS XTERRA C$_{18}$, 5 μm, 19×150. Mobile phase: MeCN/H$_2$O buffered with 0.1% TFA from 30% to 90% of MeCN in 14 minutes, run time 18 minutes). Fractions containing the pure compound were combined and freeze dried to afford compound 142 (TFA salt) as an off white solid (30% over 4 steps). $^1$H NMR (400 MHz, DMSO-d$_6$, 300 K) δ 10.65 (s, 1H), 8.89 (s, 1H), 8.65-8.49 (bs, 1H), 8.25-8.11 (bs, 1H), 7.62-7.56 (m, 2H), 7.51-7.38 (m, 4H), 7.31 (d, J 7.3, 1H), 7.24 (d, J 7.3, 1H), 5.69-5.53 (m, 1H), 5.24 (d, J 17.2, 1H), 5.14 (d, J 11.9, 1H), 4.71 (d, J 12.4, 1H), 4.61 (d, J 12.4, 1H), 4.31 (bt, 1H), 4.37 (bs, 1H), 4.16 (d, J 8.8, 1H), 4.04 (d, J 11.9, 1H), 3.79 (dd, J 11.5, 3.9, 1H), 3.00-2.91 (m, 1H), 2.91-2.81 (m, 1H), 2.80-2.68 (m, 2H), 2.22 (q, J 17.5, 8.8, 1H), 2.02-1.91 (m, 1H), 1.83-1.69 (m, 2H), 1.68-1.56 (m, 2H), 1.41-1.24 (m, 5H), 1.22-1.02 (m, 13H), 0.91 (t, J 7.3, 4H). MS (ES+) m/z 705 (M+H)+.

Scheme 17

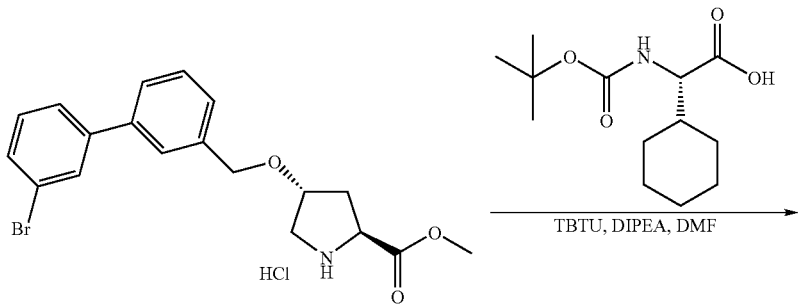

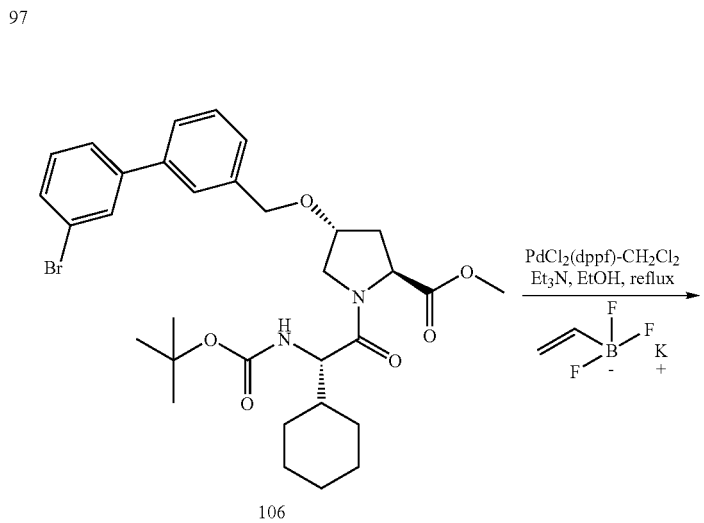

-continued
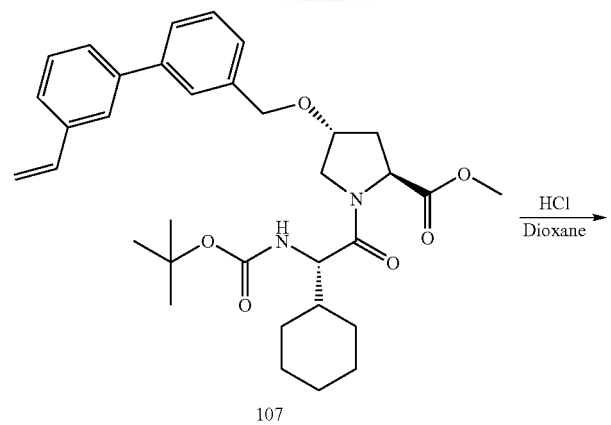
107
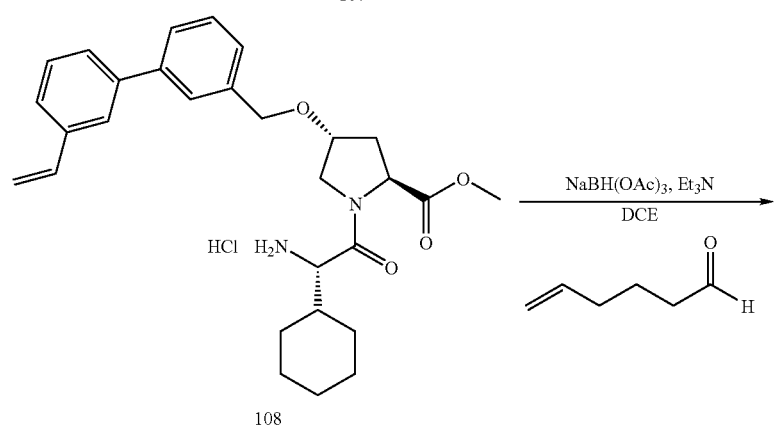
108
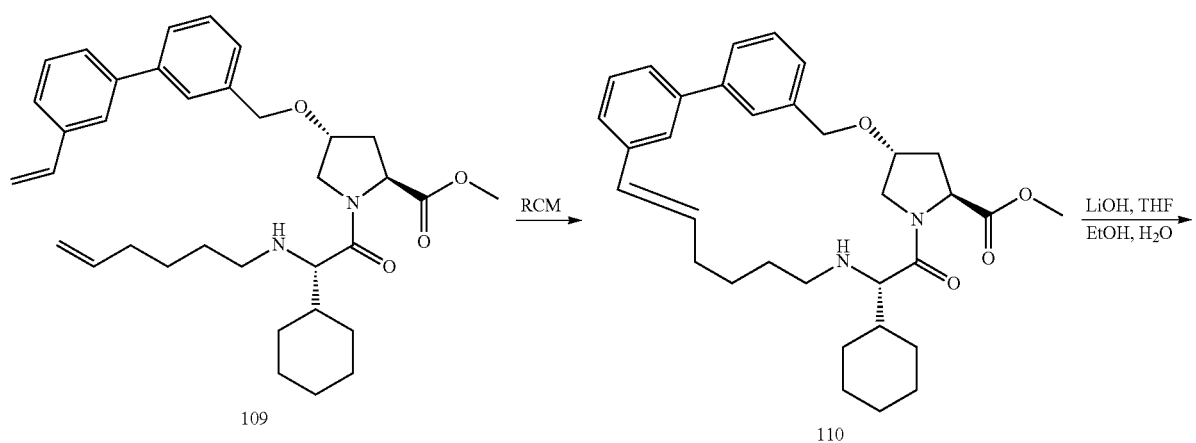
109 110
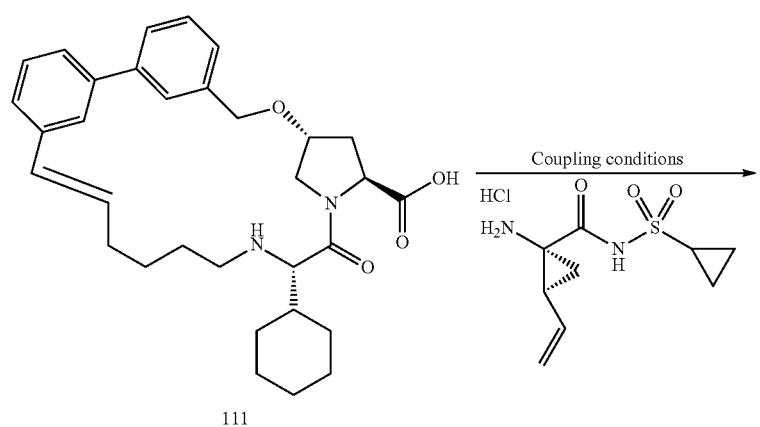
111

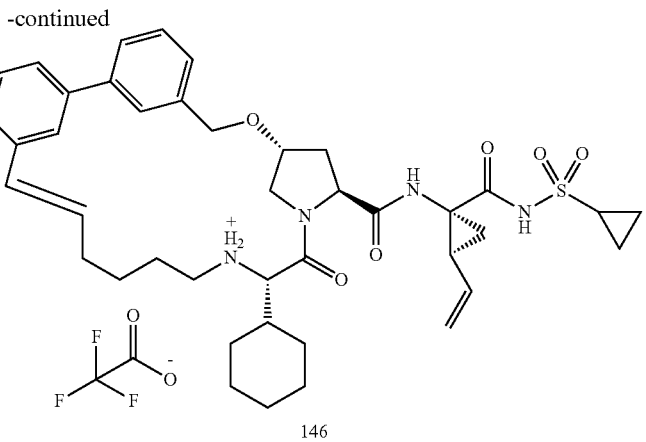

146

Compound 146: (9R,11S,14S,20E)-14-cyclohexyl-N-((1R,2S)-1-{[(cyclopropylsulfonyl)amino]carbonyl}-2-vinylcyclopropyl)-13-oxo-8-oxa-12,15-diazatetracyclo[20.3.1.1[2,6].1[9,12]]octacosa-1(26),2(28),3,5,20,22,24-heptaene-11-carboxamide Step 1: methyl (4R)-4-[(3'-bromobiphenyl-3-yl)methoxy]-1-{(2S)-2-[(tert-butoxycarbonyl)amino]-2-cyclohexylacetyl}-L-prolinate 106

(2S)-[(tert-butoxycarbonyl)amino](cyclohexyl)acetic acid (1.05 eq.), DIPEA (3.2 eq.) and TBTU (1.1 eq.) were added to a 0.12M solution of methyl (4R)-4-[(3'-bromobiphenyl-3-yl)methoxy]-L-prolinate hydrochloride 97 in DMF. The reaction mixture was stirred at RT for 2 h then it was diluted with EtOAc:$H_2O$ and acidified with aqueous (1N) HCl. The phases were separated and the organic layer was washed sequentially with aqueous (1N) HCl, aqueous (2N) NaOH and brine, dried ($Na_2SO_4$) and evaporated under reduced pressure to afford the title compound 106 (95% crude yield) as a pale yellow foam which was used without further purification. $^1$H NMR (400 MHz, DMSO-$d_6$, 300 K) δ 7.86 (s, 1H), 7.70 (d, J 7.8, 1H), 7.66-7.57 (m, 3H), 7.54-7.33 (m, 3H), 6.94 (d, J 8.6, 1H), 4.65 (d, J 11.6, 1H), 4.58 (d, J 11.6, 1H), 4.36 (t, J 8.5, 1H), 4.32 (bs, 1H), 4.19 (d, J 11.1, 1H), 4.11 (t, J 11.1, 1H), 3.74-3.66 (m, 1H), 3.65 (s, 3H), 2.48-2.35 (m, 1H), 2.08-1.97 (m, 1H), 1.83-1.55 (m, 6H), 1.44-1.37 (m, 1H), 1.34 (s, 9H), 1.22-1.09 (m, 2H), 1.08-0.93 (m, 2H). MS (ES$^+$) m/z 629, 631 (M+H)$^+$ Step 2: methyl (4R)-1-{(2S)-2-[(tert-butoxycarbonyl)amino]-2-cyclohexylacetyl}-4-[(3'-vinylbiphenyl-3-yl)methoxy]-L-prolinate 107

Potassium vinyltrifluoroborate (2.0 eq.), $Et_3N$ (2.0 eq.) and $PdCl_2$(dppf)-DCM adduct (0.05 eq.) were sequentially added to a 0.12 M solution of methyl (4R)-4-[(3'-bromobiphenyl-3-yl)methoxy]-1-{(2S)-2-[(tert-butoxycarbonyl)amino]-2-cyclohexylacetyl}-L-prolinate 106 in EtOH. The reaction mixture was stirred with heating at reflux for 3 h then it was cooled down to RT and diluted with $H_2O$:EtOAc. The phases were separated and the organic layer was washed with brine, dried ($Na_2SO_4$) and evaporated under reduced pressure. The residue was purified by flash chromatography ($SiO_2$, PE:EtOAc=8:2) to afford the title compound 107 (72%) as a foam. $^1$H NMR (400 MHz, DMSO-$d_6$, 300 K) δ 7.75 (s, 1H), 7.71-7.61 (m, 2H), 7.59 (d, J 7.3, 1H), 7.56-4.43 (m, 3H), 7.39 (d, J 7.3, 1H), 6.94 (d, J 8.6, 1H), 6.86 (dd, J 17.7, 10.9, 1H), 5.98 (d, J 17.7, 1H), 5.36 (d, J 10.9, 1H), 4.66 (d, J 11.7, 1H), 4.58 (d, J 11.7, 1H), 4.36 (t, J 8.6, 1H), 4.32 (bs, 1H), 4.19 (d, J 10.9, 1H), 4.15-4.07 (m, 1H), 3.73-3.66 (m, 1H), 3.65 (s, 3H), 2.46-2.35 (m, 1H), 2.07-1.98 (m, 1H), 1.82-1.57 (m, 6H), 1.42-1.36 (m, 1H), 1.34 (s, 9H), 1.20-1.12 (m, 2H), 1.07-0.94 (m, 2H). MS (ES$^+$) m/z 577 (M+H)$^+$ Step 3: methyl (4R)-1-[(2S)-2-amino-2-cyclohexylacetyl]-4-[(3'-vinylbiphenyl-3-yl)methoxy]-L-prolinate hydrochloride 108

Methyl (4R)-1-{(2S)-2-[(tert-butoxycarbonyl)amino]-2-cyclohexylacetyl}-4-[(3'-vinylbiphenyl-3-yl)methoxy]-L-prolinate 107 was suspended in 4M solution of HCl in dioxane (final conc. 1.3 M) and stirred at RT for 2 h. The solvent was removed under reduced pressure, the residue was taken up with $Et_2O$ and evaporated to dryness to afford the title compound 108 (95% crude yield) as a white foam. $^1$H NMR (400 MHz, DMSO-$d_6$, 300 K) δ 8.15 (bs, 3H), 7.46 (s, 1H), 7.72-7.64 (m, 2H), 7.60 (d, J 7.6, 1H), 7.57-7.46 (m, 3H), 7.40 (d, J 7.6, 1H), 6.87 (dd, J 17.7, 11.1, 1H), 5.98 (d, J 17.7, 1H), 5.37 (d, J 11.1, 1H), 4.65 (s, 2H), 4.46 (t, J 8.5, 1H), 4.36 (bs, 1H), 4.25-4.18 (m, 1H), 4.10 (d, J 11.4, 1H), 3.72-3.65 (m, 1H), 3.68 (s, 3H), 2.60-2.55 (m, partially obscured by residual DMSO-$d_6$, 1H), 2.11-2.00 (m, 1H), 1.89-1.61 (m, 6H), 1.32-1.02 (m, 5H). MS (ES$^+$) m/z 477 (M+H)$^+$ Step 4: methyl (4R)-1-[(2S)-2-cyclohexyl-2-(hex-5-en-1-ylamino)acetyl]-4-[(3'-vinylbiphenyl-3-yl)methoxy]-L-prolinate 109

$Et_3N$ (2.0 eq.), hex-5-enal (1.0 eq.) (obtained from hex-5-en-1-ol via a PCC oxidation and sodium triacetoxyborohydride (1.3 eq.) were sequentially added to a 0.07 M solution of methyl (4R)-1-[(2S)-2-amino-2-cyclohexylacetyl]-4-[(3'-vinylbiphenyl-3-yl)methoxy]-L-prolinate hydrochloride 108 in DCE. The reaction mixture was stirred at RT for 2 h then it was diluted with DCM, saturated aqueous $NaHCO_3$ and extracted. The collected organic layers were washed with brine, dried ($Na_2SO_4$) and evaporated under reduced pressure to yield a residue that was purified by flash chromatography ($SiO_2$, PE:EtOAc=7:3) to afford the title compound 109 (67%) as a colourless oil.

$^1$H NMR (400 MHz, DMSO-$d_6$, 300 K) δ 7.74 (s, 1H), 7.70-7.43 (m, 7H), 7.35 (d, J 7.6, 1H), 6.86 (dd, J 17.7, 10.9, 1H), 5.97 (d, J 17.7, 1H), 5.79-5.76 (m, 1H), 5.36 (d, J 10.9, 1H), 4.99-4.87 (m, 2H), 4.64 (s, 2H), 4.43 (t, J 8.3, 1H), 4.32

(bs, 1H), 4.00 (d, J 11.4, 1H), 3.64 (s, 3H), 3.64-3.57 (m, 1H), 3.21-3.13 (m, 1H), 2.49-2.34 (m, 2H), 2.33-2.22 (m, 1H), 2.06-1.97 (m, 1H), 1.97-1.83 (m, 3H), 1.75-1.57 (m, 5H), 1.34-1.06 (m, 9H). MS (ES$^+$) m/z 559 (M+H)$^+$

Step 5: methyl (9R, 11S, 14S,20E)-14-cyclohexyl-13-oxo-8-oxa-12,15-diazatetracyclo[20.3.1.1$^{2,6}$.1$^{9,12}$]octacosa-1(26),2(28),3,5,20,22,24-heptaene-11-carboxylate 110

To a 0.01M solution of methyl (4R)-1-[(2S)-2-cyclohexyl-2-(hex-5-en-1-ylamino)acetyl]-4-[(3'-vinylbiphenyl-3-yl)methoxy]-L-prolinate 109 in DCM was added TFA (1.3 eq.) and Zhan I (0.15 eq.). The reaction mixture was stirred under microwave irradiation for 20 min. at 100° C. The solvent was evaporated under reduced pressure and the crude material was used in the following step without further purification. MS (ES$^+$) m/z 531 (M+H)$^+$ Step 6: (9R,11S,14S,20E)-14-cyclohexyl-13-oxo-8-oxa-12,15-diazatetracyclo[20.3.1.1$^{2,6}$.1$^{9,12}$]octacosa-1(26),2(28),3,5,20,22,24-heptaene-11-carboxylic acid 111

LiOH (3.0 eq.) was added to a 0.04M solution of methyl (9R,11S,14S,20E)-14-cyclohexyl-13-oxo-8-oxa-12,15-diazatetracyclo[20.3.1.1$^{2,6}$.1$^{9,12}$]octacosa-1(26),2(28),3,5,20,22,24-heptaene-11-carboxylate 110 in a mixture of THF:EtOH:H$_2$O (2:1:1) and the reaction mixture was stirred at 40° C. for 2 h. The solvents were removed under reduced pressure, the residue was suspended in EtOAc/H$_2$O, aqueous (1N) HCl was added to acidic pH and the phases separated. The collected organic layers were dried (Na$_2$SO$_4$) and evaporated under reduced pressure to afford a residue which was used without further purification. MS (ES$^+$) m/z 517 (M+H)$^+$ Step 7: (9R,11S, 14S,20E)-14-cyclohexyl-N-((1R,2S)-1-{[(cyclopropylsulfonyl)amino]carbonyl}-2-vinylcyclopropyl)-13-oxo-8-oxa-12,15-diazatetracyclo[20.3.1.1$^{2,6}$.1$^{9,12}$]octacosa-1(26),2(28),3,5,20,22,24-heptaene-11-carboxamide 146

48 (1.2 eq.) and HATU (1.2 eq.) were added to a 0.12M solution of (9R,11S,14S,20E)-14-cyclohexyl-13-oxo-8-oxa-12,15-diazatetracyclo[20.3.1.1$^{2,6}$.1$^{9,12}$]octacosa-1(26),2(28),3,5,20,22,24-heptaene-11-carboxylic acid 111 in DMF containing DIPEA (4.0 eq.). The reaction mixture was stirred at RT overnight then it was concentrated to dryness and the residue was dissolved in DMSO and purified by RP-HPLC (stationary phase: column WATERS XBRIDGE 19×150 mm, 5 µm; mobile phase: MeCN/H$_2$O buffered with 0.1% TFA from 50% to 90% of MeCN in 14 min., run time 18 min.). Fractions containing the pure compound were combined and freeze dried to afford compound 146 (TFA salt) as an offwhite solid (4.0% over 3 steps). $^1$H NMR (400 MHz, DMSO-d$_6$, 300 K) δ 10.73 (s, 1H), 8.83 (s, 1H), 8.80-8.68 (m, 1H), 8.58-8.42 (m, 1H), 7.92 (s, 2H), 7.68 (d, J 7.6, 1H), 7.62 (d, J 7.6, 1H), 7.51-7.40 (m, 2H), 7.29 (t, J 8.1, 2H), 6.58 (d, J 15.7, 1H), 6.49-6.37 (m, 1H), 5.68-5.54 (m, 1H), 5.27 (d, J 16.9, 1H), 5.16 (d, J 11.6, 1H), 4.74 (d, J 11.9, 1H), 4.60 (d, J 11.9, 1H), 4.50-4.33 (m, 3H), 4.19 (d, J 11.1, 1H), 3.86 (dd, J 11.1, 3.8, 1H), 3.18-2.91 (m, 3H), 2.60-2.46 (m, partially obscured by residual DMSO-d6, 1H), 2.43-2.24 (m, 2H), 2.19 (q, J 8.8, 1H), 2.09-1.97 (m, 1H), 1.92-1.65 (m, 9H), 1.64-1.52 (m, 1H), 1.38-1.02 (m, 11H). MS (ES) m/z 729 (M+H)$^+$.

Scheme 18

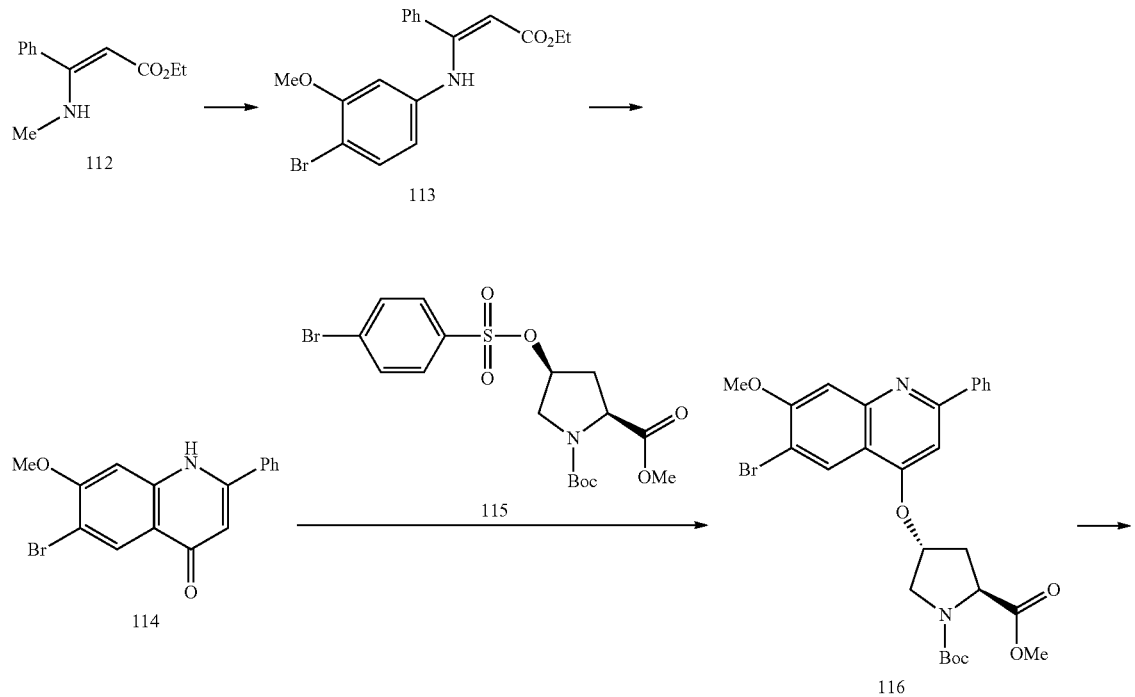

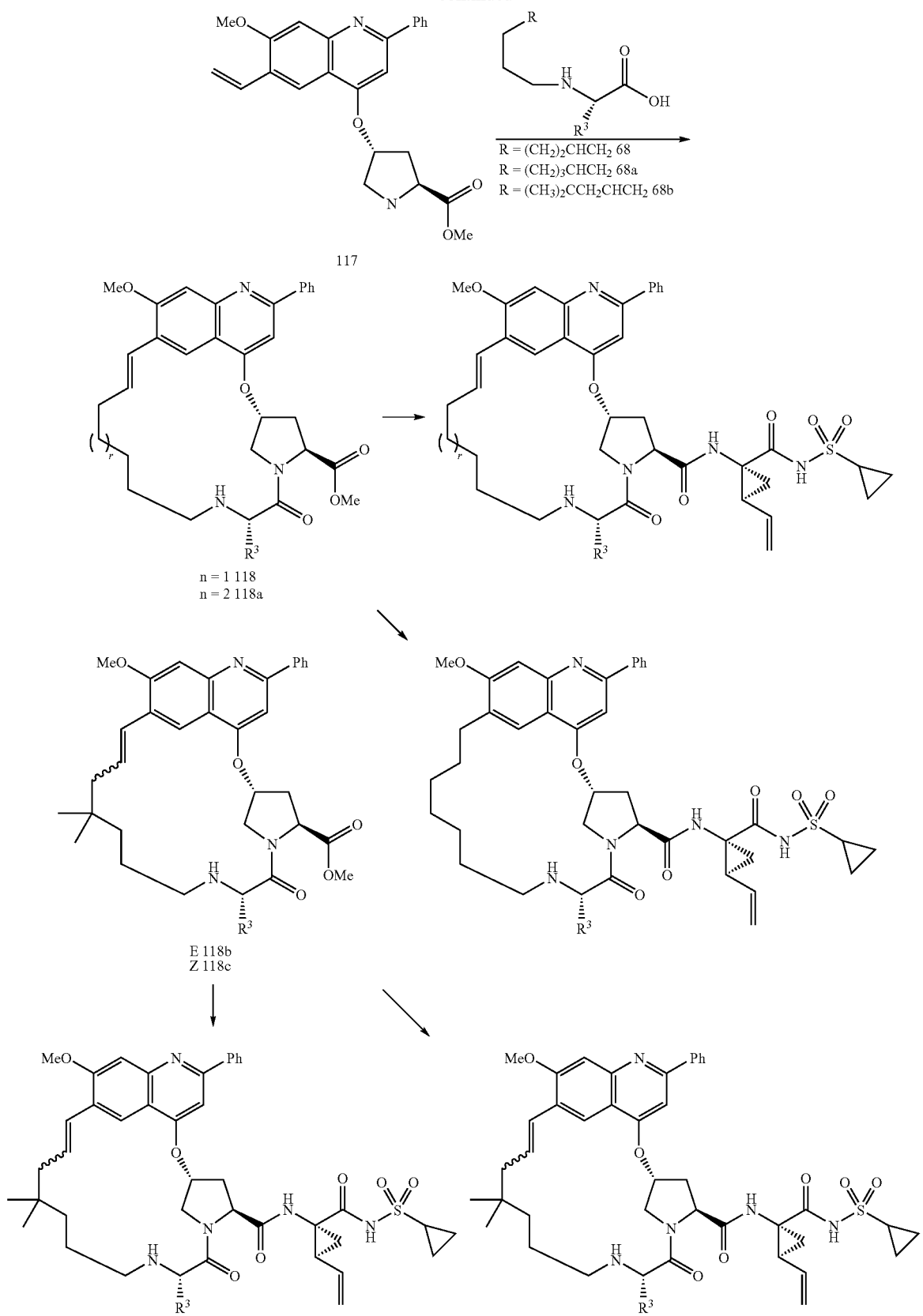

Compound 138: (2R,4S,7S,14E)-7-cyclohexyl-N-((1R,2S)-1-{[(cyclopropylsulfonyl)amino]carbonyl}-2-vinylcyclopropyl)-23-methoxy-6-oxo-20-phenyl-3,4,6,7,8,9,10,11,12,13-decahydro-2H-16,18-etheno-2,5-methanopyrido[3,4-r][1,5,8] oxadiazacyclononadecine-4-carboxamide (2S)-Cyclohexyl(hept-6-en-1-ylamino)acetic acid 68 ($R^3$=cHex)

Following the procedure described above for Compound 19 Steps 1-2, treatment of cyclohexylglycine tert-butyl ester hydrochloride with hept-6-enal afforded the title compound 68 (76%) as an oil. MS (ES$^+$) m/z 254 (M+H)$^+$.

Ethyl 3-(methylamino)-3-phenylacrylate (112)

To a solution of ethyl benzoylacetate and methylamine (2M in THF, 8 eq.) in EtOH (1 M) was added acetic acid (8 eq.). The reaction mixture was heated to reflux and stirred for three days. The reaction mixture was concentrated and partition between DCM and 1N HCl. The layers were separated and the organic layer was dried ($Na_2SO_4$), filtered and concentrated to give the title compound 112 (20%) which was used with no further purification.

Step 1: Ethyl 3-[(4-bromo-3-methoxyphenyl)amino]-3-phenylacrylate 113

To a solution of compound 112 and 4-bromo-3-methoxyaniline (1 eq.) in DCM (0.15 M) was added PPTS (1 eq.). The mixture was heated to reflux and stirred for one day. The mixture was cooled and the solids were removed by filtration and washed with dichloromethane. The filtrate was concentrated and purified by column chromatography ($SiO_2$, PE:EtOAc with EtOAc from 1 to 15%) to give the title compound 113 (80%). $^1$H NMR (CDCl$_3$) δ (ppm) 10.32 (br s, 1H), 7.32 (m, 5H), 7.20 (d, J 8.5, 1H), 6.19 (dd, J 8.5, 2.5, 1H), 6.11 (d, J 2.5, 1H), 5.03 (s, 1H), 4.21 (q, J 7.0, 2H), 3.50 (s, 3H), 1.32 (t, J 7.0, 3H).

Step 2: 6-Bromo-7-methoxy-2-phenylquinolin-4(1H)-one 114

DOWTHERM A (0.19 M) was heated to reflux (~300° C.). A mixture of the product 113 in DOWTHERM A (2.5 M) was added to the heated DOWTHERM A solution portionwise. The mixture was stirred at reflux for 1 h after the addition was complete. The mixture was cooled to RT, filtered, and the solid was washed with hexane to give the title compound 114 (86%). $^1$H NMR (DMSO-d$_6$) δ(ppm) 11.69 (s, 1H), 8.19 (s, 1H), 7.82 (m, 2H), 7.59 (m, 3H), 7.35 (s, 1H), 6.33 (s, 1H), 3.96 (s, 3H).

1-tert-Butyl 2-methyl (2S,4S)-4-{[(4-bromophenyl)sulfonyl]oxy}pyrrolidine-12-dicarboxylate 115

To a solution of 1-tert-butyl 2-methyl (2S,4S)-4-hydroxypyrrolidine-1,2-dicarboxylate and DABCO (1.6 eq.) in toluene (0.20 M) at 0° C. was added a solution of brosyl chloride (3.14 g, 12.3 mmol) in toluene (0.41 M) and stirring was continued at RT. EtOAc was added and a white precipitate formed, the reaction mixture was stirred for 20 min and filtered. The filtrate was partitioned between EtOAc and 2.5% aqueous NaHCO$_3$. The layers were separated and the organic was washed with 5% aqueous potassium bisulfate and brine, dried (Na$_2$SO$_4$), filtered and concentrated. The resulting oil was triturated with hexane/ether and the resulting white solid recovered by filtration affording the title compound 115 (67%), which was then used without further purification. MS (ES) m/z 464 and 466 (M+H)$^+$.

Step 3: 1-tert-Butyl 2-methyl (2S,4R)-4-[(6-bromo-7-methoxy-2-phenylquinolin-4-yl)oxy]pyrrolidine-1,2-dicarboxylate 116

To a solution of compounds 115 and 114 in N-methylpyrrolidine (0.36 M), cesium carbonate (2 eq.) was added. The reaction mixture was heated to 50° C. and stirred for 3 h and cooled. The reaction mixture was diluted with EtOAc, washed with saturated aqueous NaHCO$_3$, water and brine, dried (Na$_2$SO$_4$), filtered and concentrated. The residue was purified by column chromatography (SiO$_2$, PE:EtOAc with EtOAc from 1 to 60%) to give the title compound 116 (99%) as a pale yellow solid. MS (ES$^+$) m/z 557 and 559 (M+H)$^+$.

Step 4: Methyl (4R)-4-[(7-methoxy-2-phenyl-6-vinylquinolin-4-yl)oxy]-L-prolinate hydrochloride 117

Tributylvinylstannane (1.15 eq.) and tetrakis(triphenylphosphine) palladium(0) (0.07 eq.) were added to a solution of compound 116 in toluene (0.09 M) and the reaction mixture was heated at 100° C. After 20 h volatiles were removed in vacuo and the residue was purified by column chromatography (SiO$_2$, PE:EtOAc with EtOAc from 1 to 60%) to give a pale yellow solid, that was taken up in a 4N solution of HCl in dioxane (0.31 M). The reaction mixture was stirred for 1 h and the resulting white solid recovered by filtration, washed with EtOAc/petroleum ether affording the title compound 117 (99%) as a pale yellow solid. MS (ES$^+$) m/z 405 (M+H)$^+$.

Step 5: (2R,4S,7S,14E)-7-cyclohexyl-23-methoxy-4-(methoxycarbonyl)-6-oxo-20-phenyl-3,4,6,7,8,9,10,11,12,13-decahydro-2H-16,18-etheno-2,5-methanopyrido[3,4-r][1,58]oxadiazacyclononadecin-8-ium trifluoroacetate 118 ($R^3$=cHex)

Following the procedure described for Compound 19 Step 3, treatment of the compounds 117 and 68 with TBTU and DIPEA afforded methyl (4R)-1-[(2S)-2-cyclohexyl-2-(hept-6-en-1-ylamino)acetyl]-4-[(7-methoxy-2-phenyl-6-vinylquinolin-4-yl)oxy]-L-prolinate (35%) as an oil. MS (ES$^+$) m/z 640 (M+H)$^+$. Treatment of this material as described for compound 19 Step 4 afforded the title compound 118 (65%) as a solid.

Step 6: (2R,4S,7S,14E)-7-cyclohexyl-N-((1R,2S)-1-{[(cyclopropylsulfonyl)amino]carbonyl}-2-vinylcyclopropyl)-23-methoxy-6-oxo-20-phenyl-3,4,6,7,8,9,10,11,12,13-decahydro-2H-16,18-etheno-2,5-methanopyrido[3,4-r][1,5,8] oxadiazacyclononadecine-4-carboxamide 138

Treatment of the compound 118 as described for Compound 19 Steps 6-7 afforded the title compound 138 (54%, TFA salt) as a white solid. MS (ES$^+$) m/z 810 (M+H)$^+$.

Compound 139: (2R,4S,7S)-7-cyclohexyl-N-((1R,2S)-1-{[(cyclopropylsulfonyl)amino]carbonyl}-2-vinlcyclopropyl)-23-methoxy-6-oxo-20-phenyl-3,4,6,7,8,9,10,11,12,13,14,15-dodecahydro-2H-16,18-etheno-2,5-methanopyrido[3,4-r][1,5,8]oxadiazacyclononadecine-4-carboxamide Treatment of compound 118 as described for Compound 19 Steps 5-7 afforded the title compound 139 (38%, TFA salt) as a white solid. MS (ES$^+$) m/z 812 (M+H)$^+$.

Compound 140: (2R,4S,7S,15E)-7-cyclohexyl-N-((1R,2S)-1-{[(cyclopropylsulfonyl)amino]carbonyl}-2-vinylcyclopropyl)-24-methoxy-6-oxo-21-phenyl-3,4,7,8,9,10,11,12,13,14-decahydro-2H,6H-17,19-etheno-2,5-methanopyrido[3,4-s][1,5,8]oxadiazacycloicosine-4-carboxamide N-[(S)-carboxy(cyclohexyl)methyl]oct-7-en-1-aminium trifluoroacetate (68a)

Following the procedure described above for Compound 19 Steps 1-2, treatment of cyclohexylglycine tert-butyl ester hydrochloride with oct-7-enal afforded the title compound 68a (19%) as a white solid. MS (ES$^+$) m/z 268 (M+H)$^+$.

Step 5: (2R,4S,7S,15E)-7-cyclohexyl-24-methoxy-4-(methoxycarbonyl)-6-oxo-21-phenyl-3,4,7,8,9,10,11,12,13,14-decahydro-2H,6H-17,19-etheno-2,5-methanopyrido[3,4-s][1,5,8]oxadiazacycloicosin-8-ium trifluoroacetate 118a (n=2 R$^3$=cHex)

Following the procedure described for Compound 118, treatment of compounds 68a and 117 afforded the title compound 118a (19%) as an oil. MS (ES$^+$) m/z 626 (M+H)$^+$.

Step 6: (2R,4S,7S,15E)-7-cyclohexyl-N-((1R,2S)-1-{[(cyclopropylsulfonyl)amino]carbonyl}-2-vinylcyclopropyl)-24-methoxy-6-oxo-21-phenyl-3,4,7,8,9,10,11,12,13,14-decahydro-2H,6H-17,19-etheno-2,5-methanopyrido[3,4-s][1,5,8]oxadiazacycloicosine-4-carboxamide 140

Treatment of compound 118a as described for Compound 138 afforded the title compound 140 (43%, TFA salt) as a solid. MS (ES$^+$) m/z 824 (M+H)$^+$.

Compound 141: (2R,4S,7S)-7-cyclohexyl-N-((1R,2S)-1-{[(cyclopropylsulfonyl)amino]carbonyl}-2-vinylcyclopropyl)-24-methoxy-6-oxo-21-phenyl-3,4,7,8,9,10,11,12,13,14,15,16-dodecahydro-2H,6H-17,19-etheno-2,5-methanopyrido[3,4-s][1,5,8]oxadiazacycloicosine-4-carboxamide Treatment of compound 118a as described for Compound 19 Steps 5-7 afforded the title compound 141 (47%, TFA salt) as a white solid. MS (ES$^+$) m/z 826 (M+H)$^+$.

Compound 147: (2R,4S,7S,14E)-7-cyclohexyl-N-((1R,2S)-1-{[(cyclopropylsulfonyl)amino]carbonyl}-2-vinylcyclopropyl)-23-methoxy-12,12-dimethyl-6-oxo-20-phenyl-3,4,6,7,8,9,10,11,12,13-decahydro-2H-16,18-etheno-2,5-methanopyrido[3,4-r][1,5,8]oxadiaza cyclononadecine-4-carboxamide (2S)-cyclohexyl[(4,4-dimethylhept-6-en-1-yl)amino]acetic acid 68b Following the procedure described above for Compound 19 Steps 1-2, treatment of cyclohexylglycine methyl ester hydrochloride with 4,4-dimethylhept-6-enal afforded the title compound 68b (56%) as a solid. $^1$H NMR (CD$_3$OD) δ (ppm) 5.84 (m, 1H), 5.06-4.99 (m, 2H), 3.28 (d, J 4.3, 1H), 2.98-2.83 (m, 2H), 1.99 (m, 2H), 1.88-1.65 (m, 8H), 1.36-1.16 (m, 7H), 1.99 (s, 6H). MS (ES$^+$) m/z 282 (M+H)$^+$.

Step 5: (2R,4S,7S,14E)-7-cyclohexyl-23-methoxy-4-(methoxycarbonyl)-12,12-dimethyl-6-oxo-20-phenyl-3,4,6,7,8,9,10,11,12,13-decahydro-2H-16,18-etheno-2,5-methanopyrido[3,4-r][1,5,8]oxadiazacyclononadecin-8-ium trifluoroacetate 118b and (2R,4S,7S,14Z)-7-cyclohexyl-23-methoxy-4-(methoxycarbonyl)-12,12-dimethyl-6-oxo-20-phenyl-3,4,6,7,8,9,10,11,12,13-decahydro-2H-16,18-etheno-2,5-methanopyrido[3,4-r][1,5,8]oxadiazacyclononadecin-8-ium trifluoroacetate 118c Following the procedure described for compound 118, treatment of compounds 117 and 68b afforded after chromatography compounds 118b (80%) and 118c (2%) as oils. MS (ES$^+$) m/z 640 (M+H)$^+$.

Step 6: (2R,4S,7S,14E)-7-cyclohexyl-N-((1R,2S)-1-{[(cyclopropylsulfonyl)amino]carbonyl}-2-vinylcyclopropyl)-23-methoxy-12,12-dimethyl-6-oxo-20-phenyl-3,4,6,7,8,9,10,11,12,13-decahydro-2H-16,18-etheno-2,5-methanopyrido[3,4-r][1,5,8]oxadiazacyclononadecine-4-carboxamide 147

Treatment of compound 118b following Step 6 for compound 138 afforded the title compound 147 (41%, TFA salt) as a solid. $^1$H NMR (DMSO-d$_6$) δ (ppm) 10.78 (br s, 1H), 8.93-8.68 (br m, 2H), 8.66 (s, 1H), 8.30-8.20 (m, 2H), 8.11 (s, 1H), 7.67-7.54 (m, 5H), 7.47 (s, 1H), 6.76 (d, J 15.7, 1H), 6.33-6.23 (m, 1H), 5.76 (br s, 1H), 5.56 (dt, J 17.1, 9.5, 1H), 5.18 (d, J 17.1, 1H), 5.09 (d, J 11.9, 1H), 4.63 (d, J 11.9, 1H), 4.50-4.40 (m, 2H), 4.00 (s, 3H), 4.01-3.90 (m, 1H), 3.23-3.12 (m, 1H), 2.90 (m, 1H), 2.81-2.68 (m, 2H), 2.26-2.06 (m, 4H), 2.00-1.66 (m, 8H), 1.32-0.95 (m, 12H), 0.93 (s, 3H), 0.91 (s, 3H). MS (ES$^+$) m/z 838 (M+H)$^+$.

Compound 148: (2R,4S,7S)-7-cyclohexyl-N-((1R,2S)-1-{[(cyclopropylsulfonyl)amino]carbonyl}-2-vinylcyclopropyl)-23-methoxy-12,12-dimethyl-6-oxo-20-phenyl-3,4,6,7,8,9,10,11,12,13,14,15-dodecahydro-2H-16,18-etheno-2,5-methanopyrido[3,4-r][1,5,8]oxadiazacyclononadecine-4-carboxamide Treatment of compound 118c as described for Compound 19 Steps 5-7 afforded the title compound 148 (37%, TFA salt) as a white solid. $^1$H NMR (DMSO-d$_6$) δ (ppm) 10.83 (br s, 1H), 8.79 (s, 1H), 8.65-8.55 (br s, 1H), 8.51-8.41 (br s, 1H), 8.28-8.20 (m, 2H), 7.83 (s, 1H), 7.67-7.54 (m, 5H), 7.47 (s, 1H), 5.85 (br s, 1H), 5.58 (dt, J 16.7, 9.5, 1H), 5.22 (d, J 16.7, 1H), 5.12 (d, J 11.6, 1H), 4.63 (dd, J 9.2, 8.2, 1H), 4.41 (d, J 12.1, 1H), 4.38-4.31 (br m, 1H), 3.98 (s, 3H), 4.01-3.89 (m, 1H), 2.97-2.84 (m, 3H), 2.80-2.73 (m, 1H), 2.68-2.57 (m, 2H), 2.35-2.25 (m, 1H), 2.14 (q, J 8.7, 1H), 2.01-1.90 (m, 1H), 1.81-0.99 (m, 22H), 0.85 (s, 3H), 0.77 (s, 3H). MS (ES$^+$) m/z 840 (M+H)$^+$.

Compound 149: (2R,4S,7S,14Z)-7-cyclohexyl-N-((1R,2S)-1-{[(cyclopropylsulfonyl)amino]carbonyl}-2-vinylcyclopropyl)-23-methoxy-12,12-dimethyl-6-oxo-20-phenyl-3,4,6,7,8,9,10,11,12,13-decahydro-2H-16,18-etheno-2,5-methanopyrido[3,4-r][1,5,8]oxadiaza cyclononadecine-4-carboxamide Treatment of compound 118c as described for Compound 19 Steps 6-7 afforded the title compound 149 (24%, TFA salt) as a white solid. MS (ES$^+$) m/z 838 (M+H)$^+$.

Scheme 19

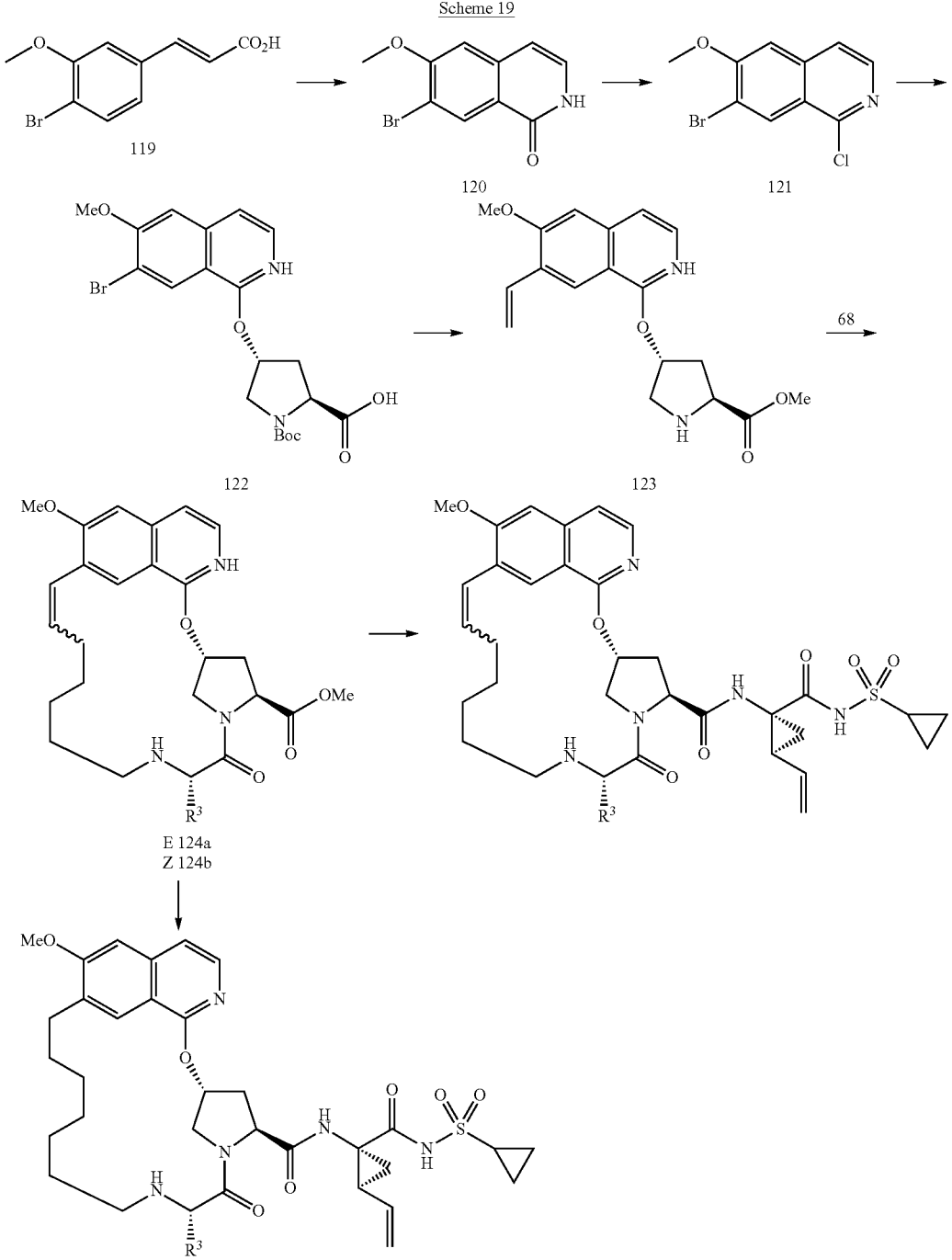

Compound 143: (2R,4S,7S,14Z)-7-cyclohexyl-N-((1R,2S)-1-{[(cyclopropylsulfonyl)amino]carbonyl}-2-vinylcyclopropyl)-23-methoxy-6-oxo-3,4,6,7,8,9,10,11,12,13-decahydro-2H-16,18-(ethanediylidene)-2,5-methanopyrido[3,2-r][1,5,8]oxadiazacyclononadecine-4-carboxamide (2E)-3-(4-Bromo-3-methoxyphenyl)acrylic acid 119

To a solution of 1-bromo-4-iodo-2-methoxybenzene (L. A. Hasvold et al., US 2004/0254159) in MeCN (1.1 M) was added acrylic acid (1.24 eq.), TEA (2.5 eq.) and palladium acetate (0.03 eq). The reaction mixture was heated to 90° C. for 40 min, cooled to RT and poured into 1N HCl. After sting for 30 min, the solid was filtered, heated to reflux in EtOH (2.3 M), allowed to cool to RT and stirred overnight. The solid was filtered and washed with 1:1 EtOH:hexane to give the desired product 119. LRMS ESI$^+$ (M+H)$^+$ 257.0.

Step 1: 7-Bromo-6-methoxisoquinolin-1(2H)-one 120

Compound 119 was azeotroped with benzene, suspended in benzene (0.5 M) with TEA (1.4 eq.), diphenylphosphoryl azide (1 eq.) was added and the reaction mixture stirred at RT for 1 h. The mixture was filtered through a pad of silica and eluted with toluene, the volatiles evaporated, the residue resuspended in diphenylmethane (0.5 M) and the mixture heated to reflux for 3 h (internal temperature 250° C.). The reaction mixture was allowed to cool to RT, stirred overnight, filtered and the solid washed with hexanes to give a tan solid (60%). LRMS ESI+ (M+H)+ 254.1.

Step 2: 7-Bromo-1-chloro-6-methoxisoquinoline 121

A mixture of compound 120 in phosphorus oxychloride (0.6 M) was heated to reflux for 2 h, cooled to RT, the volatiles evaporated and the residue partitioned between 3N NaOH and DCM. The organic phase was dried ($Na_2SO_4$), solvent evaporated and the solid triturated with $Et_2O$ and filtered to give a solid (74%). LRMS ESI+ (M+H)+ 274.0.

Step 3: (4R)-4-[(7-bromo-6-methoxyisoquinolin-1-yl)oxy]-1-(tert-butoxycarbonyl)-L-proline 122

To a solution of trans 4-hydroxy L-BOC-proline in DMSO (0.23 M) at RT potassium t-butoxide (3 eq.) was added. The reaction mixture was stirred at RT for 30 min, cooled to 15° C. and compound 121 (1 eq) was added as a solution DMSO (0.9 M), the reaction mixture was allowed to warm to RT and stirred for 30 min. The reaction mixture was quenched with ice-cold 10% citric acid solution and partitioned with EtOAc. The organic layer was washed with aqueous citric acid solution, water and brine and the aqueous phases back extracted with EtOAc. The combined organic phases were dried ($Na_2SO_4$) and the solvent evaporated. LRMS ESI+ (M+H-tBu)+ 411.2.

Step 4: (2S,4R)-2-(methoxycarbonyl)-4-[(6-methoxy-7-vinylisoquinolin-yl)oxy]pyrrolidinium chloride 123

To a solution of compound 122 in MeOH (0.1 M) was added TMS-diazomethane (4.2 eq.) and the mixture was stirred at RT for 20 min. Volatiles were evaporated and the crude purified by chromatography to obtain 1-tert-butyl 2-methyl (2S,4R)-4-[(7-bromo-6-methoxyisoquinolin-1-yl)oxy]pyrrolidine-1,2-dicarboxylate as a pale orange foam (79%). To the previous compound dissolved in toluene (0.1 M) tetrakis-(triphenylphospin)-palladium(0) (0.1 eq.) and vinyltri-N-butyltin (1 eq) were added and the mixture was heated at 100° C. for 20 h. Volatiles were evaporated and the residue purified by chromatography to obtain 1-tert-butyl 2-methyl (2S,4R)-4-[(6-methoxy-7-vinylisoquinolin-1-yl)oxy]pyrrolidine-1,2-dicarboxylate as a pale yellow foam (45%) that was treated with HCl 4N in dioxane (26 eq) at RT. After 30 min volatiles were evaporated to obtain the title compound 123 in quantitative yield. MS (ES+) m/z 329 (M+H)+.

Step 5: (2R,4S,7S,14E)-7-cyclohexyl-23-methoxy-4-(methoxycarbonyl)-6-oxo-3,4,6,7,8,9,10,11,12,13-decahydro-2H-16,18-(ethanediylidene)-2,5-methanopyrido[3,2-r][1,5,8]oxadiazacyclononadecin-8-ium trifluoroacetate 124a (11% yield) and (2R,4S,7S,14z)-7-cyclohexyl-23-methoxy-4-(methoxycarbonyl)-6-oxo-3,4,6,7,8,9,10,11,12,13-decahydro-2H-1618-(ethanediylidene)-2,5-methanopyrido[3,2-r][1,5,8]oxadiazacyclononadecin-8-ium trifluoroacetate 124b Following the procedure described for compound 19 Step 3, treatment of compound 123 and 68 ($R^3$=cHex) with TBTU and DIPEA afforded methyl (4R)-1-[(2S)-2-cyclohexyl-2-(hept-6-en-1-ylamino)acetyl]-4-[(6-methoxy-7-vinylisoquinolin-1-yl)oxy]-L-prolinate (57%) as a oil. Treatment of this material as described for 19 Step 4 afforded after purification by preparative RP-HPLC (stationary phase: column WATERS XBRIDGE C18, 19×100 mm, mobile phase MeCN/water buffered with 0.1% TFA) the two title compounds: 124a (first eluted, 59% yield) and 124b (second eluted, 11% yield). MS (ES+) m/z 536 (M+H)+.

Step 6: (2R,4S,7S,14Z)-7-cyclohexyl-N-((1R,2S)-1-{[(cyclopropylsulfonyl)amino]carbonyl}-2-vinylcyclopropyl)-23-methoxy-6-oxo-3,4,6,7,8,9,10,11,12,13-decahydro-2H-16,18-(ethanediylidene)-2,5-methanopyrido[3,2-r][1,5,8]oxadiazacyclononadecine-4-carboxamide 143

Treatment of compound 124b as described for compound 138 Step 6 afforded the title compound 143 (23%, TFA salt) as a solid. MS (ES+) m/z 734 (M+H)+.

Compound 144: (2R,4S,7S,14E)-7-cyclohexyl-N-((1R,2S)-1-{[(cyclopropylsulfonyl)amino]carbonyl}-2-vinylcyclopropyl)-23-methoxy-6-oxo-3,4,6,7,8,9,10,11,12,13-decahydro-2H-16,18-(ethanediylidene)-2,5-methanopyrido[3,2-r][1,5,8]oxadiazacyclo nonadecine-4-carboxamide Treatment of ((2R,4S,7S,14E)-7-cyclohexyl-23-methoxy-4-(methoxycarbonyl)-6-oxo-3,4,6,7,8,9,10,11,12,13-decahydro-2H-16,18-(ethanediylidene)-2,5-methanopyrido [3,2-r][1,5,8]oxadiazacyclononadecin-8-ium trifluoroacetate as described for Compound 138 Step 6 afforded the title compound 144 (25%, TFA salt) as a solid. MS (ES+) m/z 734 (M+H)+.

Compound 145: (2R,4S,7S)-7-cyclohexyl-N-((1R,2S)-1-{[(cyclopropylsulfonyl)amino]carbonyl}-2-vinylcyclopropyl)-23-methoxy-6-oxo-3,4,6,7,8,9,10,11,12,13,14,15-dodecahydro-2H-16,18-(ethanediylidene)-2,5-methanopyrido[3,2-r][1,5,8]oxadiazacyclononadecine-4-carboxamide Treatment of compound 124a as described for Compound 19 Steps 5-7 afforded the title compound 145 (25%, TFA salt) as a white solid. MS (ES+) m/z 736 (M+H)+.

Compound 150: (2R,4S,7S,14E)-7-cyclohexyl-N-((1R,2S)-1-{[(cyclopropylsulfonyl)amino]carbonyl}-2-vinylcyclopropyl)-23-methoxy-12,12-dimethyl-6-oxo-3,4,6,7,8,9,10,11,12,13-decahydro-2H-16,18-(ethanediylidene)-2,5-methanopyrido[3,2-r][1,5,8]oxadiaza cyclononadecine-4-carboxamide Following the procedures described for compound 143 Steps 5-6, treatment of (2S,4R)-2-(methoxycarbonyl)-4-[(6-methoxy-7-vinylisoquinolin-1-yl)oxy]pyrrolidinium chloride with compound 68b afforded the title compound 150 (14%, TFA salt) as a white solid. MS (ES+) m/z 762 (M+H)+.

Compound 134: (3S,3aR,6S,8R)-N-((1R,2S)-1-{[(cyclopropylsulfonyl)amino]carbonyl}-2-vinylcyclopropyl)-3-methyl-4,10-dioxo-2,3,3a,4,7,8,12,17,18,19,20,21,22,23-tetradecahydro-1H,6H-5, 8:11,13-dimethanopyrrolo[2,1-j][4,2,8,11]benzoxatriazacycloicosine-6-carboxamide (3S)-1-hept-6-en-1-yl-3-methyl-L-proline 125

Following the procedure described above for Compound 19 Steps 1-2, treatment of methyl (3S)-3-methyl-L-prolinate with hept-6-enal afforded the title compound 125 (80%) as an oil. $^1$H NMR (400 MHz, DMSO-$d_6$, 300 K) δ 5.78 (m, 1H), 5.03-4.92 (m, 2H), 3.58-3.48 (m, 2H), 3.19-3.01 (m, 2H), 3.07-2.95 (m, 1H), 2.34-2.22 (m, 1H), 2.12-2.00 (m, 3H), 1.69-1.55 (m, 3H), 1.41-1.22 (m, 4H), 1.18 (d, J 8.8, 3H).

(3S,3aS,6S,8R)-6-{[((1R,2S)-1-{[(cyclopropylsulfonyl)amino]carbonyl}-2-vinylcyclopropyl)amino]carbonyl}-3-methyl-4,10-dioxo-2,3,3a,4,7,8,12,17,18,19,20,21,22,23-tetradecahydro-1H,6H-5, 8:11,13-dimethanopyrrolo[2,1-j][4,2,8,11]benzoxatriazacycloicosin-24-ium trifluoroacetate Following the procedures described for Compound 19, Steps 3-7, treatment of compound 125 with (2S,4R)-2-(methoxycarbonyl)-4-{[(4-vinyl-1,3-dihydro-2H-isoindol-2-yl)carbonyl]oxy}pyrrolidinium chloride afforded the title compound 134 (24%, TFA salt) as a solid. MS (ES⁺) m/z 696 (M+H)⁺.

Table 1 lists specific compounds of the present invention including the compounds described in the experimental section. The table provides the structure and name of each compound and the mass of its molecular ion plus 1 (M+1) as determined via mass spectrometry (ES–MS). The synthetic scheme employed to prepare the compound is indicated in the last column.

TABLE 1

| Cmp no. | Chemical name | Structure | Mass spec. (M + 1) | Procedure (Scheme no.) |
|---|---|---|---|---|
| 1 | (5R,7S,10S,12R or S)-N-((1R,2S)-1-{[(cyclopropylsulfonyl)amino]carbonyl}-2-vinylcyclopropyl)-10-isopropyl-3,9-dioxo-12-(trifluoromethyl)-6,7,9,10,11,12,13,14,15,16,17,18-dodecahydro-1H,5H-2,22:5,8-dimethano-4,2,8,11-benzoxatriazacycloicosine-7-carboxamide | 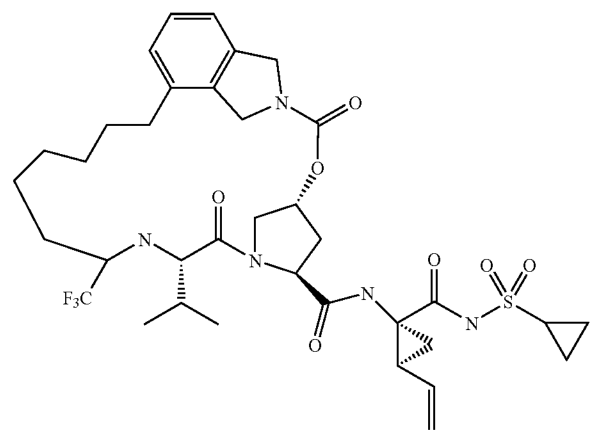 | 752 | 1 |
| 2 | (2R,4S,7S,9R or S)-N-((1R,2S)-1-{[(cyclopropylsulfonyl)amino]carbonyl}-2-vinylcyclopropyl)-7-isopropyl-6-oxo-9-(trifluoromethyl)-3,4,6,7,8,9,10,11,12,13,14,15-dodecahydro-2H-16,18-(ethanediylidene)-2,5-methanopyrido[3,2-r][1,5,8]oxadiazacyclononadecine-4-carboxamide | 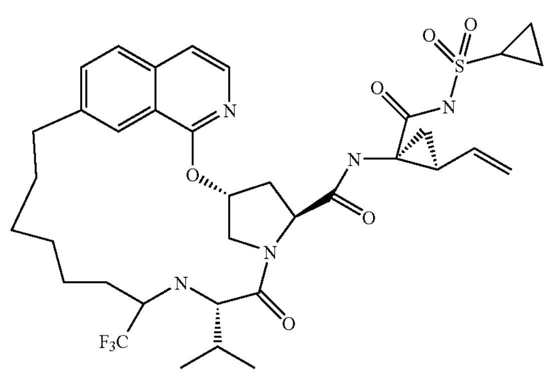 | 734 | 3 |
| 3 | (5R,7S,10R,17E)-N-((1R,2S)-1-{[(cyclopropylsulfonyl)amino]carbonyl}-2-vinylcyclopropyl)-3,9-dioxo-10-(trifluoromethyl)-6,7,9,10,11,12,13,14,15,16-decahydro-1H,5H-2,22:5,8-dimethano-4,2,8,11-benzoxatriazacyclicosine-7-carboxamide | 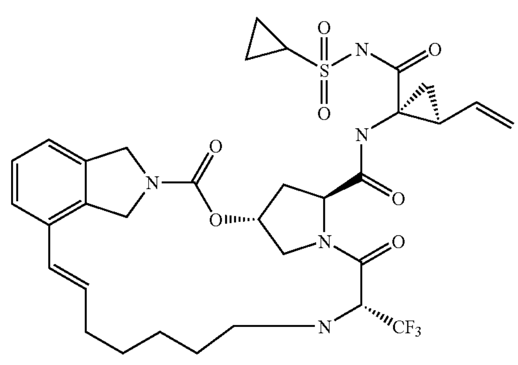 | 708 | 4 |

TABLE 1-continued

| Cmp no. | Chemical name | Structure | Mass spec. (M + 1) | Procedure (Scheme no.) |
|---|---|---|---|---|
| 4 | (5R,7S,10S,12R or S)-N-((1R,2S)-1-{[(cyclopropylsulfonyl)amino]carbonyl}-2-vinylcyclopropyl)-10-isopropyl-3,9-dioxo-12-(trifluoromethyl)-6,7,9,10,11,12,13,14,15,16,17,18-dodecahydro-1H,5H-2,22:5,8-dimethano-4,2,8,11-benzoxatriaza-cycloicosine-7-carboxamide | 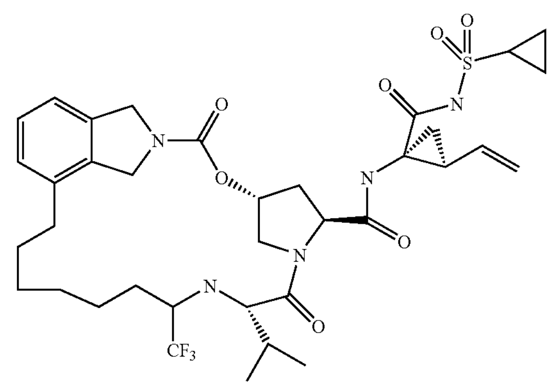 | 752 | 1 |
| 5 | (5R,7S,10S,12R or S)-10-cyclohexyl-N-((1R,2S)-1-{[(cyclopropylsulfonyl)amino]carbonyl}-2-vinylcyclopropyl)-3,9-dioxo-12-(trifluoromethyl)-6,7,9,10,11,12,13,14,15,16,17,18-dodecahydro-1H,5H-2,22:5,8-dimethano-4,2,8,11-benzoxatriaza-cycloicosine-7-carboxamide | 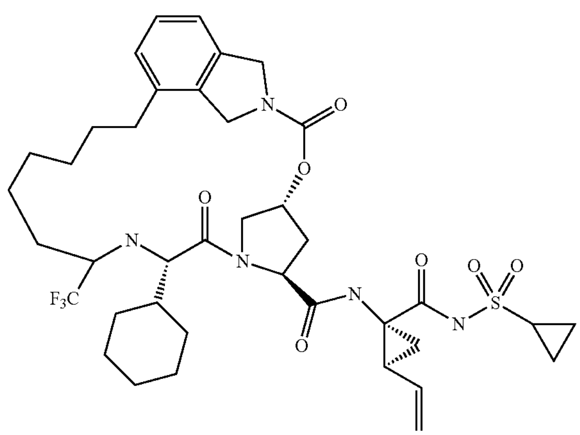 | 792 | 1 |
| 6 | (5R,7S,10S,12R or S)-10-cyclohexyl-N-((1R,2R)-1-{[(cyclopropylsulfonyl)amino]carbonyl}-2-ethylcyclopropyl)-3,9-dioxo-12-(trifluoromethyl)-6,7,9,10,11,12,13,14,15,16,17,18-dodecahydro-1H,5H-2,22:5,8-dimethano-4,2,8,11-benzoxatriaza-cycloicosine-7-carboxamide | 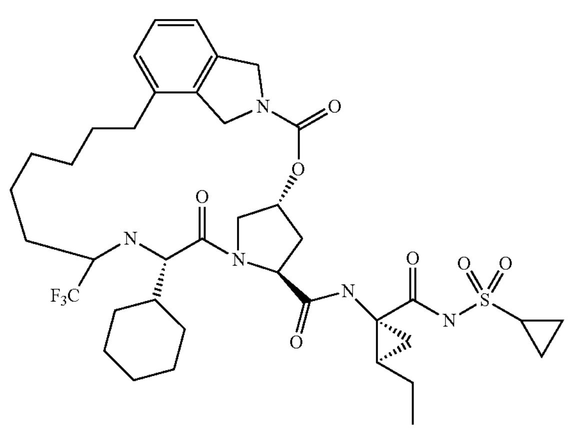 | 794 | 2 |

TABLE 1-continued

| Cmp no. | Chemical name | Structure | Mass spec. (M + 1) | Procedure (Scheme no.) |
|---|---|---|---|---|
| 7 | (5R,7S,10S,12R or S)-10-cyclohexyl-N-((1R,2S)-1-{[(cyclopropylsulfonyl)amino]carbonyl}-2-vinylcyclopropyl)-3,9-dioxo-12-(trifluoromethyl)-1,6,7,9,10,11,12,13,14,15,16,17-dodecahydro-5H-2,21:5,8-dimethano-4,2,8,11-benzoxatriazacyclononadecine-7-carboxamide | 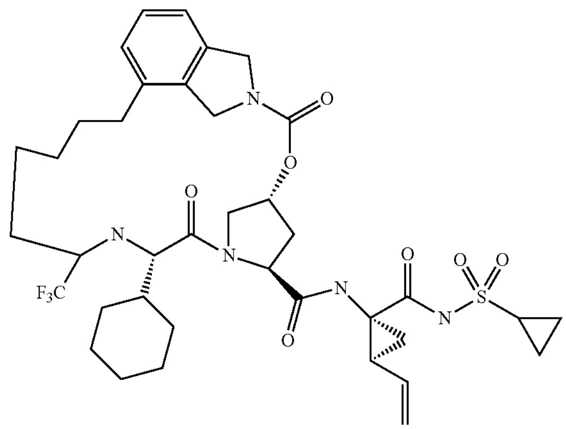 | 778 | 1 |
| 8 | (2R,4S,7R,14E)-N-((1R,2S)-1-{[(cyclopropylsulfonyl)amino]carbonyl}-2-vinylcyclopropyl)-6-oxo-7-(trifluoromethyl)-3,4,6,7,8,9,10,11,12,13-decahydro-2H-16,18-(ethanediylidene)-2,5-methanopyrido[3,2-r][1,5,8]oxadiazacyclononadecine-4-carboxamide | 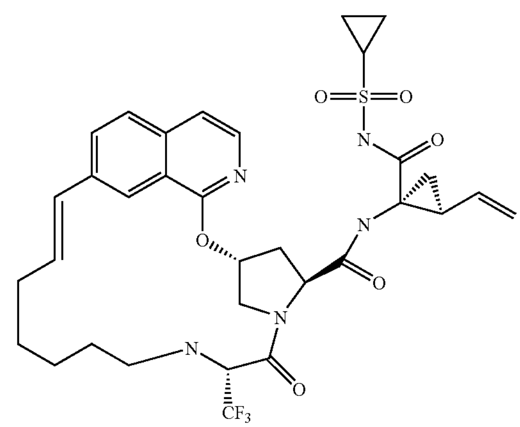 | 690 | 5 |
| 9 | (2R,4S,7R)-N-((1R,2S)-1-{[(cyclopropylsulfonyl)amino]carbonyl}-2-vinylcyclopropyl)-6-oxo-7-(trifluoromethyl)-3,4,6,7,8,9,10,11,12,13,14,15-dodecahydro-2H-16,18-etheno-2,5-methanopyrido[3,2-r][1,5,8]oxadiazacyclononadecine-4-carboxamide | 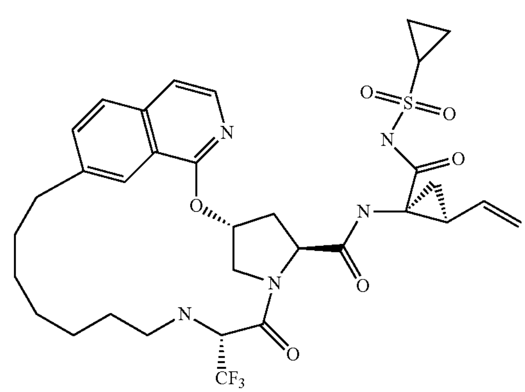 | 692 | 5 |

TABLE 1-continued

| Cmp no. | Chemical name | Structure | Mass spec. (M + 1) | Procedure (Scheme no.) |
|---|---|---|---|---|
| 10 | (5R,7S,10S,12R or S)-N-((1R,2S)-1-{[(cyclopropylsulfonyl)amino]carbonyl}-2-vinylcyclopropyl)-10-isopropyl-12-methyl-3,9-dioxo-6,7,9,10,11,12,13,14,15,16,17,18-dodecahydro-1H,5H-2,22:5,8-dimethano-4,2,8,11-benzoxatriazacycloicosine-7-carboxamide | 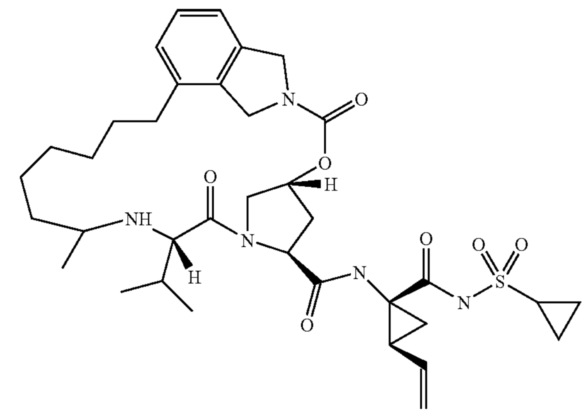 | 698 | 6 |
| 11 | (5R,7S,10S,12R or S)-N-((1R,2S)-1-{[(cyclopropylsulfonyl)amino]carbonyl}-2-vinylcyclopropyl)-10-isopropyl-12-methyl-3,9-dioxo-6,7,9,10,11,12,13,14,15,16,17,18-dodecahydro-1H,5H-2,22:5,8-dimethano-4,2,8,11-benzoxatriazacycloicosine-7-carboxamide | 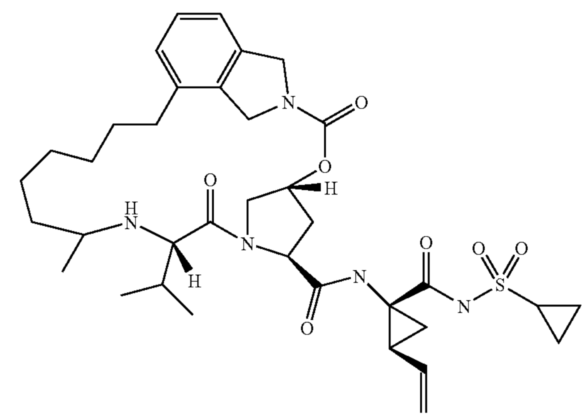 | 698 | 6 |
| 12 | (5R,7S,10S,17E)-N-((1R,2S)-1-{[(cyclopropylsulfonyl)amino]carbonyl}-2-vinylcyclopropyl)-10-methyl-3,9-dioxo-6,7,9,10,11,12,13,14,15,16-decahydro-1H,5H-2,22:5,8-dimethano-4,2,8,11-benzoxatriazacycloicosine-7-carboxamide | 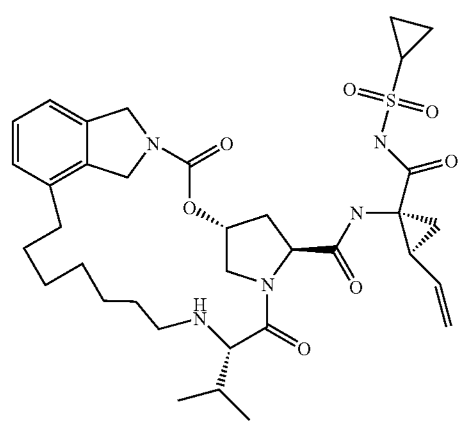 | 684 | 8 |
| 13 | (5R,7S,10S,17E)-N-((1R,2S)-1-{[(cyclopropylsulfonyl)amino]carbonyl}-2-vinylcyclopropyl)-13,13-difluoro-10-isopropyl-3,9-dioxo-6,7,9,10,11,12,13,14,15,16-decahydro-1H,5H-2,22:5,8-dimethano-4,2,8,11-benzoxatriazacycloicosine-7-carboxamide | Chiral | 718 | 10 |

TABLE 1-continued

| Cmp no. | Chemical name | Structure | Mass spec. (M + 1) | Procedure (Scheme no.) |
|---|---|---|---|---|
| 14 | (5R,7S,10S)-N-((1R,2S)-1-{[(cyclopropylsulfonyl)amino]carbonyl}-2-vinylcyclopropyl)-13,13-difluoro-10-isopropyl-3,9-dioxo-6,7,9,10,11,12,13,14,15,16,17,18-dodecahydro-1H,5H-2,22:5,8-dimethano-4,2,8,11-benzoxatriaza-cycloicosine-7-carboxamide | Chiral | 720 | 10 |
| 15 | (5R,7S,10S,12R or S,17E)-N-((1R,2S)-1-{[(cyclopropylsulfonyl)amino]carbonyl}-2-vinylcyclopropyl)-10-isopropyl-12-methyl-3,9-dioxo-6,7,9,10,11,12,13,14,15,16-decahydro-1H,5H-2,22:5,8-dimethano-4,2,8,11-benzoxatriazacycloicosine-7-carboxamide | 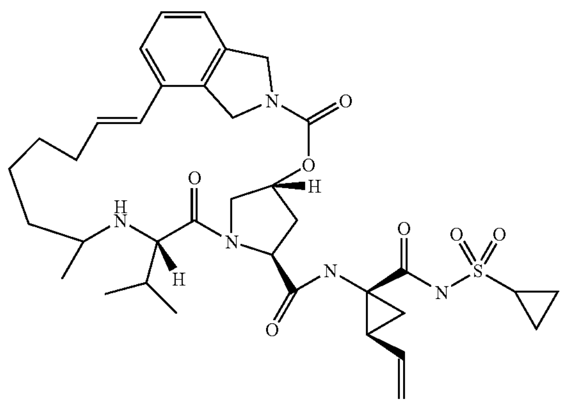 | 696 | 6 |
| 16 | (5R,7S,10S,12R or S)-N-((1R,2S)-1-{[(cyclopropylsulfonyl)amino]carbonyl}-2-vinylcyclopropyl)-10-isopropyl-3,9-dioxo-12-(pentafluoroethyl)-6,7,9,10,11,12,13,14,15,16,17,18-dodecahydro-1H,5H-2,22:5,8-dimethano-4,2,8,11-benzoxatriaza-cycloicosine-7-carboxamide | 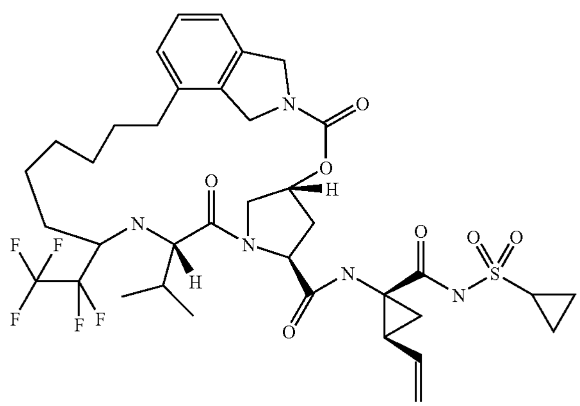 | 802 | 1 |
| 17 | (5R,7S,10S,12R or S)-N-((1R,2R)-1-{[(cyclopropylsulfonyl)amino]carbonyl}-2-ethylcyclopropyl)-10-isopropyl-12-methyl-3,9-dioxo-6,7,9,10,11,12,13,14,15,16,17,18-dodecahydro-1H,5H-2,22:5,8-dimethano-4,2,8,11-benzoxatriaza-cycloicosine-7-carboxamide | 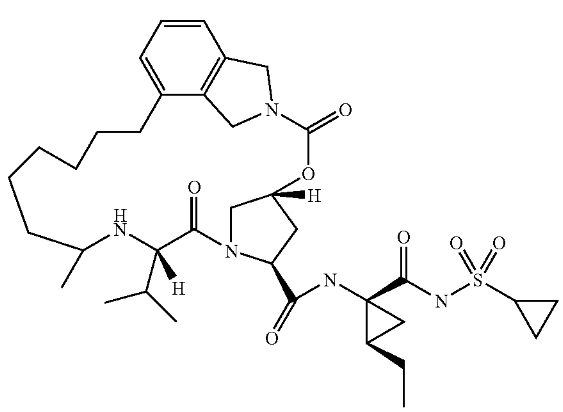 | 700 | 6 |

TABLE 1-continued

| Cmp no. | Chemical name | Structure | Mass spec. (M + 1) | Procedure (Scheme no.) |
|---|---|---|---|---|
| 18 | (5R,7S,10S)-N-((1R,2S)-1-{[(cyclopropylsulfonyl)amino]carbonyl}-2-vinylcyclopropyl)-10-methyl-3,9-dioxo-6,7,9,10,11,12,13,14,15,16,17,18-dodecahydro-1H,5H-2,22:5,8-dimethano-4,2,8,11-benzoxatriaza-cycloicosine-7-carboxamide | 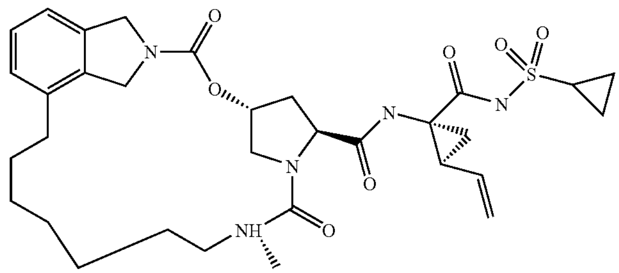 | 656 | 8 |
| 19 | (5R,7S,10S)-N-((1R,2S)-1-{[(cyclopropylsulfonyl)amino]carbonyl}-2-vinylcyclopropyl)-10-isopropyl-3,9-dioxo-6,7,9,10,11,12,13,14,15,16,17,18-dodecahydro-1H,5H-2,22:5,8-dimethano-4,2,8,11-benzoxatriaza-cycloicosine-7-carboxamide | 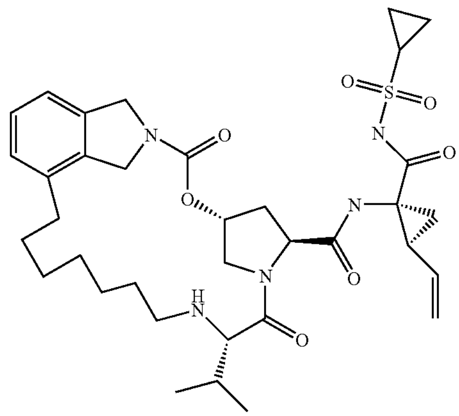 | 684 | 8 |
| 20 | (5R,7S,10S,17E)-N-((1R,2S)-1-{[(cyclopropylsulfonyl)amino]carbonyl}-2-vinylcyclopropyl)-10-isopropyl-3,9-dioxo-6,7,9,10,11,12,13,14,15,16-decahydro-1H,5H-2,22:5,8-dimethano-4,2,8,11-benzoxatriazacycloicosine-7-carboxamide | 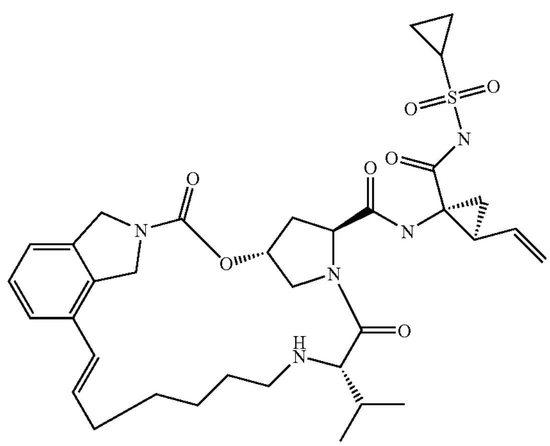 | 682 | 8 |
| 21 | (5R,7S,10S,12R or S)-10-cyclohexyl-N-((1R,2S)-1-{[(cyclopropylsulfonyl)amino]carbonyl}-2-vinylcyclopropyl)-12-methyl-3,9-dioxo-6,7,9,10,11,12,13,14,15,16,17,18-dodecahydro-1H,5H-2,22:5,8-dimethano-4,2,8,11-benzoxatriaza-cycloicosine-7-carboxamide | 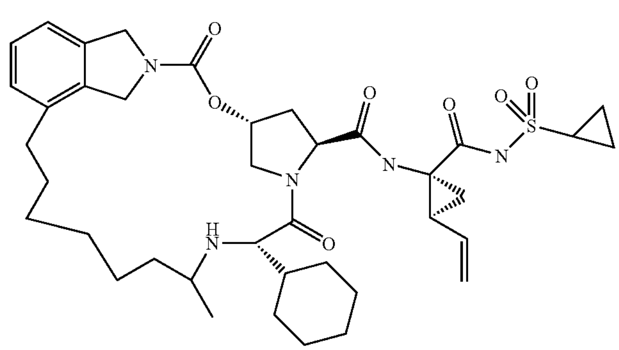 | 738 | 6 |

TABLE 1-continued

| Cmp no. | Chemical name | Structure | Mass spec. (M + 1) | Procedure (Scheme no.) |
|---|---|---|---|---|
| 22 | (2R,4S,7S,9R or S)-N-((1R,2S)-1-{[(cyclopropylsulfonyl)amino]carbonyl}-2-vinylcyclopropyl)-7-isopropyl-9-methyl-6-oxo-3,4,6,7,8,9,10,11,12,13,14,15-dodecahydro-2H-16,18-etheno-2,5-methanopyrido[3,2-r][1,5,8]oxadiazacyclononadecine-4-carboxamide | 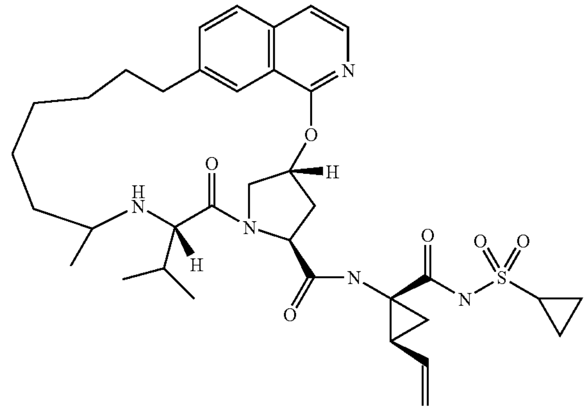 | 680 | 14 |
| 23 | (2R,4S,7S,9S or R)-N-((1R,2S)-1-{[(cyclopropylsulfonyl)amino]carbonyl}-2-vinylcyclopropyl)-7-isopropyl-9-methyl-6-oxo-3,4,6,7,8,9,10,11,12,13,14,15-dodecahydro-2H-16,18-etheno-2,5-methanopyrido[3,2-r][1,5,8]oxadiazacyclononadecine-4-carboxamide | 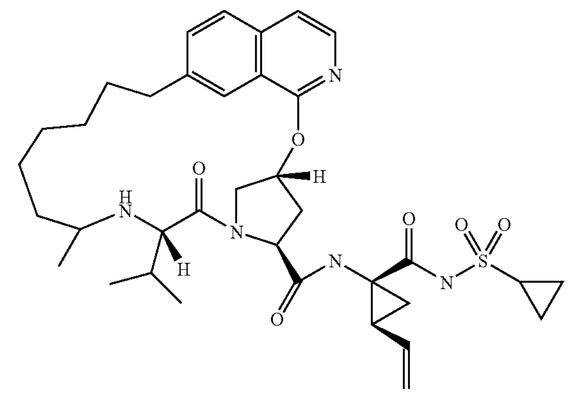 | 680 | 14 |
| 24 | (5R,7S,10S,12R or S,7E)-10-cyclohexyl-N-((1R,2S)-1-{[(cyclopropylsulfonyl)amino]carbonyl}-2-vinylcyclopropyl)-12-methyl-3,9-dioxo-6,7,9,10,11,12,13,14,15,16-decahydro-1H,5H-2,22:5,8-dimethano-4,2,8,11-benzoxatriazacycloicosine-7-carboxamide | 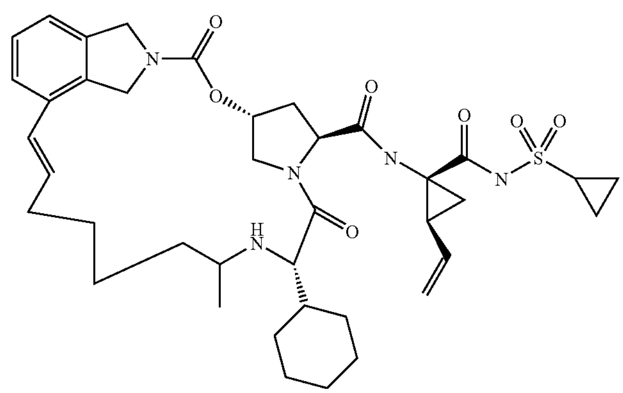 | 736 | 6 |
| 25 | (5R,7S,10S,12R or S)-10-cyclohexyl-N-((1R,2S)-1-{[(cyclopropylsulfonyl)amino]carbonyl}-2-vinylcyclopropyl)-12-methyl-3,9-dioxo-6,7,9,10,11,12,13,14,15,16,17,18-dodecahydro-1H,5H-2,22:5,8-dimethano-4,2,8,11-benzoxatriazacycloicosine-7-carboxamide | 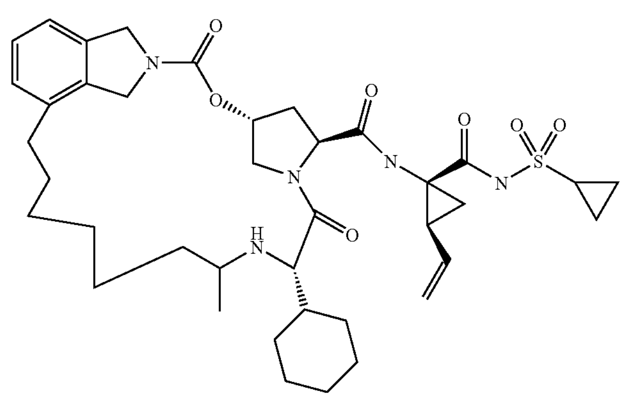 | 738 | 6 |

TABLE 1-continued

| Cmp no. | Chemical name | Structure | Mass spec. (M + 1) | Procedure (Scheme no.) |
|---|---|---|---|---|
| 26 | (5R,7S,10S,12R or S)-10-cyclohexyl-N-((1R,2S)-1-{[(cyclopropylsulfonyl)amino]carbonyl}-2-vinylcyclopropyl)-11,12-dimethyl-3,9-dioxo-6,7,9,10,11,12,13,14,15,16,17,18-dodecahydro-1H,5H-2,22:5,8-dimethano-4,2,8,11-benzoxatriazacycloicosine-7-carboxamide | 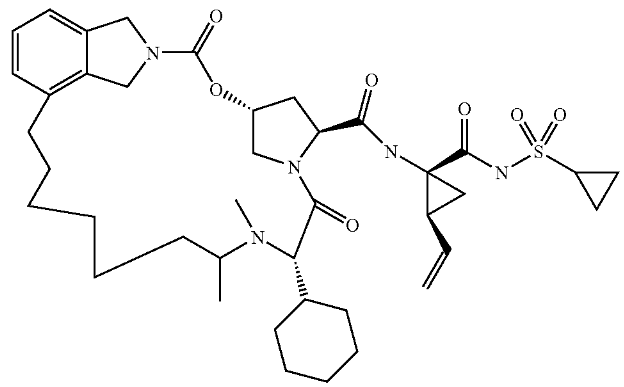 | 752 | 9 |
| 27 | (5R,7S,10S,12R or S,17E)-10-cyclopentyl-N-((1R,2S)-1-{[(cyclopropylsulfonyl)amino]carbonyl}-2-vinylcyclopropyl)-12-methyl-3,9-dioxo-6,7,9,10,11,12,13,14,15,16-decahydro-1H,5H-2,22:5,8-dimethano-4,2,8,11-benzoxatriazacycloicosine-7-carboxamide | 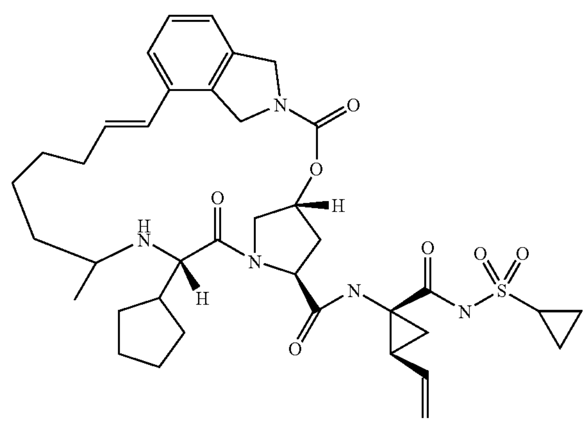 | 722 | 6 |
| 28 | (5R,7S,10S,12R or S,17E)-10-cyclopentyl-N-((1R,2S)-1-{[(cyclopropylsulfonyl)amino]carbonyl}-2-vinylcyclopropyl)-12-methyl-3,9-dioxo-6,7,9,10,11,12,13,14,15,16-decahydro-1H,5H-2,22:5,8-dimethano-4,2,8,11-benzoxatriazacycloicosine-7-carboxamide | 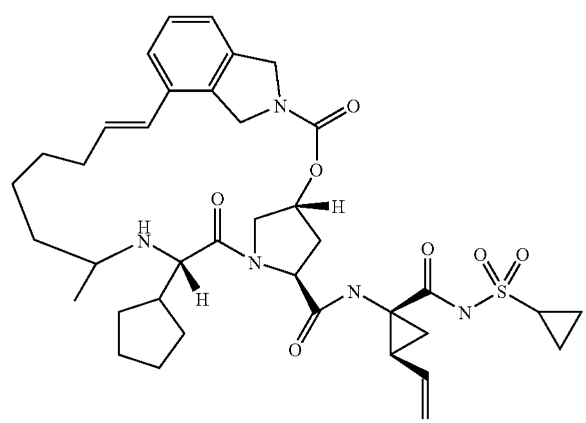 | 722 | 6 |

TABLE 1-continued

| Cmp no. | Chemical name | Structure | Mass spec. (M + 1) | Procedure (Scheme no.) |
|---|---|---|---|---|
| 29 | (5R,7S,10S,12R or S)-10-cyclopentyl-N-((1R,2S)-1-{[(cyclopropylsulfonyl)amino]carbonyl}-2-vinylcyclopropyl)-12-methyl-3,9-dioxo-6,7,9,10,11,12,13,14,15,16,17,18-dodecahydro-1H,5H-2,22:5,8-dimethano-4,2,8,11-benzoxatriaza-cycloicosine-7-carboxamide | 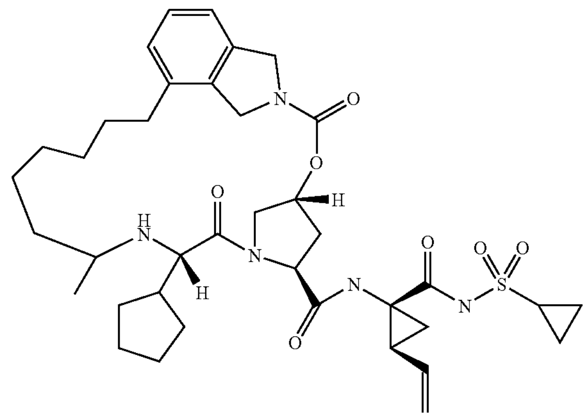 | 724 | 6 |
| 30 | (1R,2S)-1-({[(5R,7S,10S,12R or S,17E)-10-cyclohexyl-12-methyl-3,9-dioxo-6,7,9,10,11,12,13,14,15,16-decahydro-1H,5H-2,22:5,8-dimethano-4,2,8,11-benzoxatriazacycloicosin-7-yl]carbonyl}amino)-2-vinylcyclopropanecarboxylic acid | 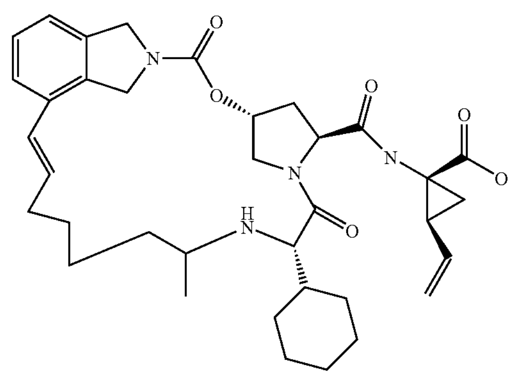 | 633 | 6 |
| 31 | (5R,7S,10S,12R or S)-N-((1R,2R)-1-{[(cyclopropylsulfonyl)amino]carbonyl}-2-ethylcyclopropyl)-12-methyl-10-[(1S)-1-methylpropyl]-3,9-dioxo-6,7,9,10,11,12,13,14,15,16,17,18-dodecahydro-1H,5H-2,22:5,8-dimethano-4,2,8,11-benzoxatriaza-cycloicosine-7-carboxamide | 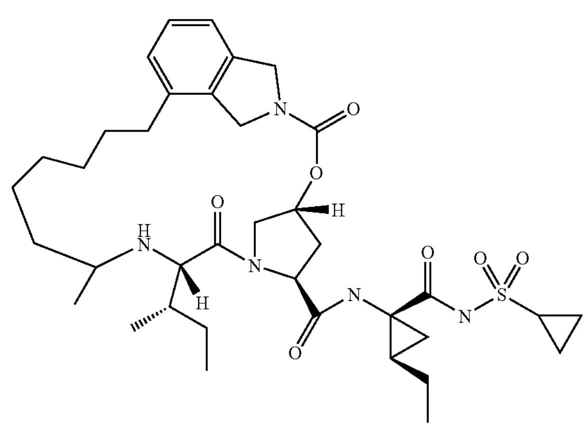 | 714 | 7 |

TABLE 1-continued

| Cmp no. | Chemical name | Structure | Mass spec. (M + 1) | Procedure (Scheme no.) |
|---|---|---|---|---|
| 32 | (2R,4S,7S,14E)-7-cyclopentyl-N-((1R,2S)-1-{[(cyclopropylsulfonyl)amino]carbonyl}-2-vinylcyclopropyl)-6-oxo-3,4,6,7,8,9,10,11,12,13-decahydro-2H-16,18-etheno-2,5-methanopyrido[3,2-r][1,5,8]oxadiazacyclononadecine-4-carboxamide | 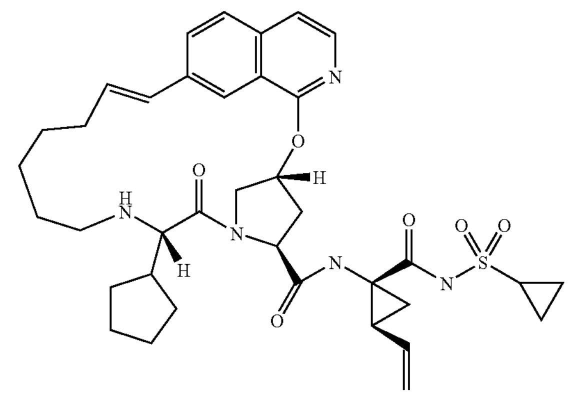 | 690 | 15 |
| 33 | (2R,4S,7S)-7-cyclopentyl-N-((1R,2S)-1-{[(cyclopropylsulfonyl)amino]carbonyl}-2-vinylcyclopropyl)-6-oxo-3,4,6,7,8,9,10,11,12,13,14,15-dodecahydro-2H-16,18-etheno-2,5-methanopyrido[3,2-r][1,5,8]oxadiaza-cyclononadecine-4-carboxamide | 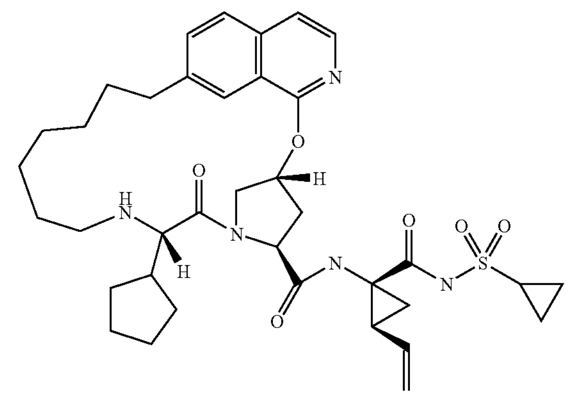 | 692 | 15 |
| 134 | (3S,3aR,6S,8R)-N-((1R,2S)-1-{[(cyclopropylsulfonyl)amino]carbonyl}-2-vinylcyclopropyl)-3-methyl-4,10-dioxo-2,3,3a,4,7,8,12,17,18,19,20,21,22,23-tetradecahydro-1H,6H-5,8:11,13-dimethanopyrrolo[2,1-j][4,2,8,11]benzoxatriazacyclo-icosine-6-carboxamide | 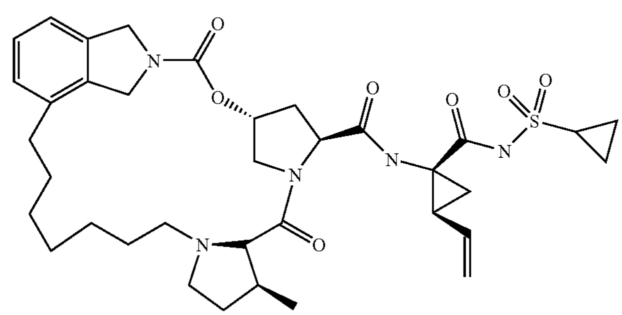 | 695 | 8 |
| 135 | (5R,7S,10S)-10-cyclopentyl-N-((1R,2S)-1-{[(cyclopropylsulfonyl)amino]carbonyl}-2-vinylcyclopropyl)-11-methyl-3,9-dioxo-6,7,10,11,12,13,15,16,17,18-decahydro-1H,5H,9H-2,22:5,8-dimethano-4,14,2,8,11-benzodioxa-triazacycloicosine-7-carboxamide | 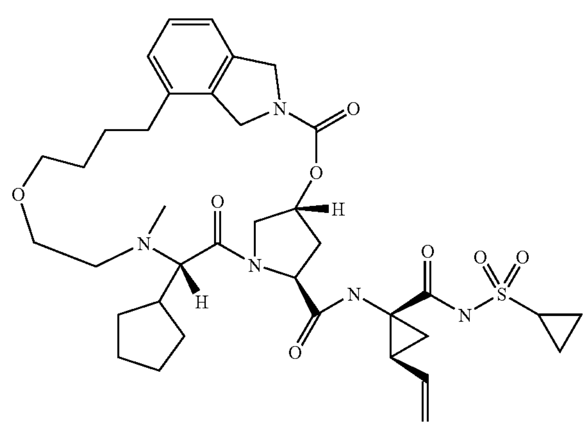 | 725 | 9 |

TABLE 1-continued

| Cmp no. | Chemical name | Structure | Mass spec. (M + 1) | Procedure (Scheme no.) |
|---|---|---|---|---|
| 136 | (5R,7S,10S)-10-cyclopentyl-N-((1R,2S)-1-{[(cyclopropylsulfonyl)amino]carbonyl}-2-vinylcyclopropyl)-13,13-dimethyl-3,9-dioxo-6,7,9,10,11,12,13,14,15,16,17,18-dodecahydro-1H,5H-2,22:5,8-dimethano-4,2,8,11-benzoxatriazacycloicosine-7-carboxamide | 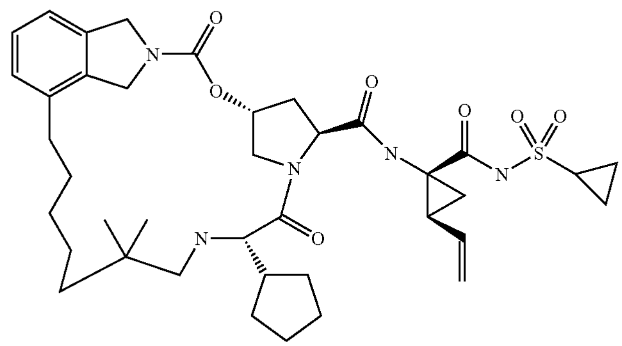 | 737 | 18 |
| 137 | (5R,7S,10S)-10-cyclopentyl-N-((1R,2S)-1-{[(cyclopropylsulfonyl)amino]carbonyl}-2-vinylcyclopropyl)-11,13,13-trimethyl-3,9-dioxo-6,7,9,10,11,12,13,14,15,16,17,18-dodecahydro-1H,5H-2,22:5,8-dimethano-4,2,8,11-benzoxatriazacycloicosine-7-carboxamide | 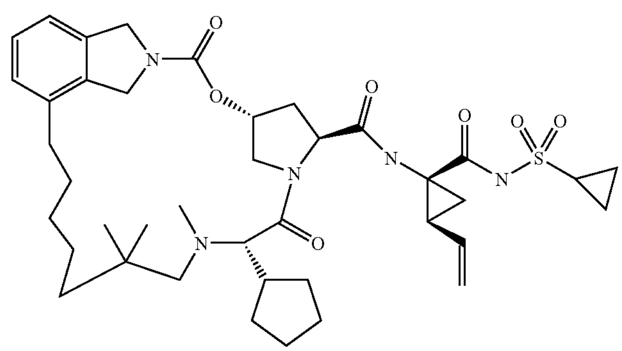 | 751 | 9 |
| 138 | (2R,4S,7S,14E)-7-cyclohexyl-N-((1R,2S)-1-{[(cyclopropylsulfonyl)amino]carbonyl}-2-vinylcyclopropyl)-23-methoxy-6-oxo-20-phenyl-3,4,6,7,8,9,10,11,12,13-decahydro-2H-16,18-etheno-2,5-methanopyrido[3,4-r][1,5,8]oxadiazacyclononadecine-4-carboxamide | 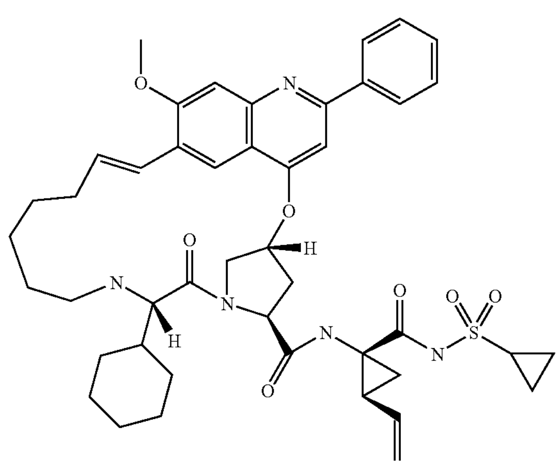 | 810 | 18 |

TABLE 1-continued

| Cmp no. | Chemical name | Structure | Mass spec. (M + 1) | Procedure (Scheme no.) |
|---|---|---|---|---|
| 139 | (2R,4S,7S)-7-cyclohexyl-N-((1R,2S)-1-{[(cyclopropylsulfonyl)amino]carbonyl}-2-vinylcyclopropyl)-23-methoxy-6-oxo-20-phenyl-3,4,6,7,8,9,10,11,12,13,14,15-dodecahydro-2H-16,18-etheno-2,5-methanopyrido[3,4-r][1,5,8]oxadiaza-cyclononadecine-4-carboxamide | 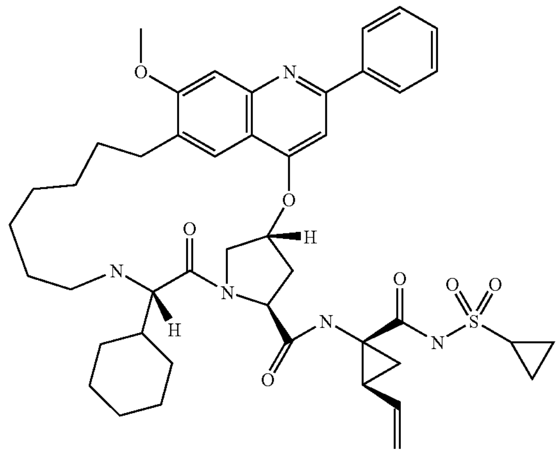 | 812 | 18 |
| 140 | (2R,4S,7S,15E)-7-cyclohexyl-N-((1R,2S)-1-{[(cyclopropylsulfonyl)amino]carbonyl}-2-vinylcyclopropyl)-24-methoxy-6-oxo-21-phenyl-3,4,7,8,9,10,11,12,13,14-decahydro-2H,6H-17,19-etheno-2,5-methanopyrido[3,4-s][1,5,8]oxadiazacycloicosine-4-carboxamide | 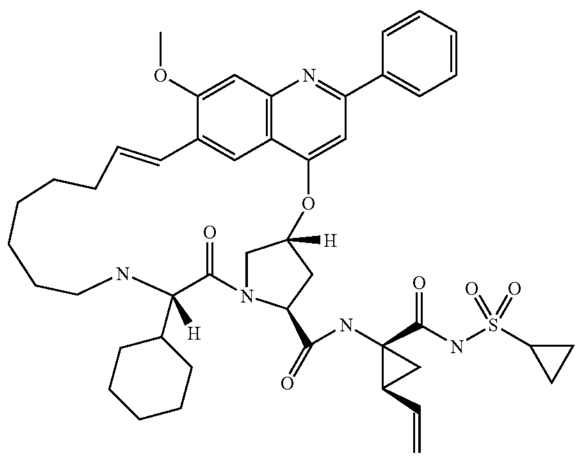 | 824 | 18 |
| 141 | (2R,4S,7S)-7-cyclohexyl-N-((1R,2S)-1-{[(cyclopropylsulfonyl)amino]carbonyl}-2-vinylcyclopropyl)-24-methoxy-6-oxo-21-phenyl-3,4,7,8,9,10,11,12,13,14,15,16-dodecahydro-2H,6H-17,19-etheno-2,5-methanopyrido[3,4-s][1,5,8]oxadiazacycloicosine-4-carboxamide | 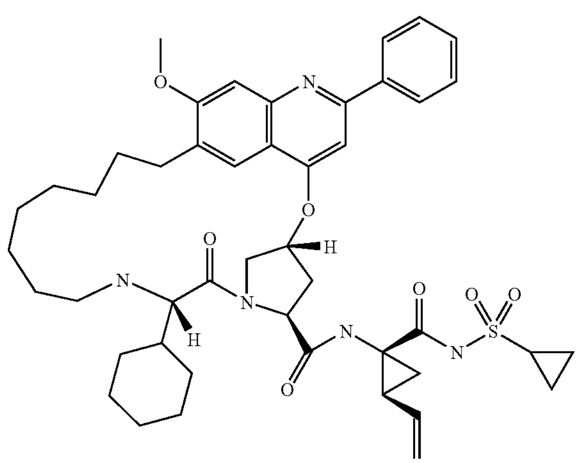 | 826 | 18 |

TABLE 1-continued

| Cmp no. | Chemical name | Structure | Mass spec. (M + 1) | Procedure (Scheme no.) |
|---|---|---|---|---|
| 142 | (9R,11S,14S)-14-tert-butyl-N-((1R,2S)-1-{[(cyclopropylsulfonyl)amino]carbonyl}-2-vinylcyclopropyl)-13-oxo-8-oxa-12,15-diazatetracyclo[20.3.1.1$^{2,6}$.1$^{9,12}$]octacosa-1(26),2(28),3,5,22,24-hexaene-11-carboxamide | 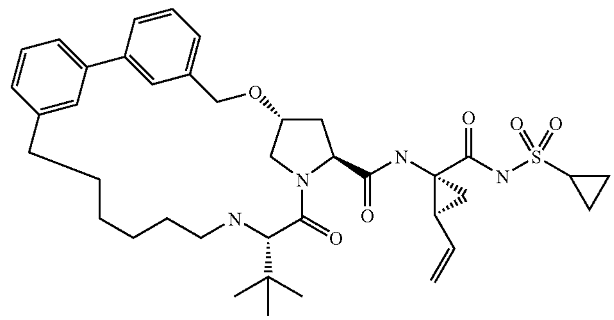 | 705 | 16 |
| 143 | (2R,4S,7S,14Z)-7-cyclohexyl-N-((1R,2S)-1-{[(cyclopropylsulfonyl)amino]carbonyl}-2-vinylcyclopropyl)-23-methoxy-6-oxo-3,4,6,7,8,9,10,11,12,13-decahydro-2H-16,18-(ethanediylidene)-2,5-methanopyrido[3,2-r][1,5,8]oxadiazacyclononadecine-4-carboxamide | 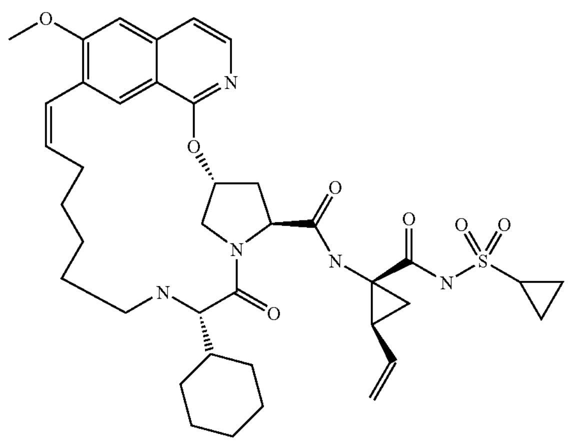 | 733 | 19 |
| 144 | (2R,4S,7S,14E)-7-cyclohexyl-N-((1R,2S)-1-{[(cyclopropylsulfonyl)amino]carbonyl}-2-vinylcyclopropyl)-23-methoxy-6-oxo-3,4,6,7,8,9,10,11,12,13-decahydro-2H-16,18-(ethanediylidene)-2,5-methanopyrido[3,2-r][1,5,8]oxadiazacyclononadecine-4-carboxamide | 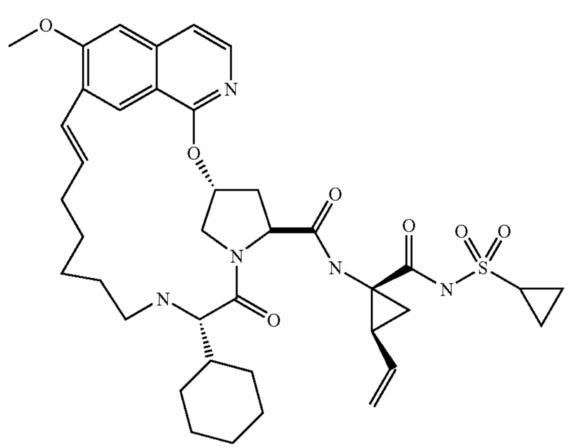 | 733 | 19 |

TABLE 1-continued

| Cmp no. | Chemical name | Structure | Mass spec. (M + 1) | Procedure (Scheme no.) |
|---|---|---|---|---|
| 145 | (2R,4S,7S)-7-cyclohexyl-N-((1R,2S)-1-{[(cyclopropylsulfonyl)amino]carbonyl}-2-vinylcyclopropyl)-23-methoxy-6-oxo-3,4,6,7,8,9,10,11,12,13,14,15-dodecahydro-2H-16,18-(ethanediylidene)-2,5-methanopyrido[3,2-r][1,5,8]oxadiazacyclononadecine-4-carboxamide | 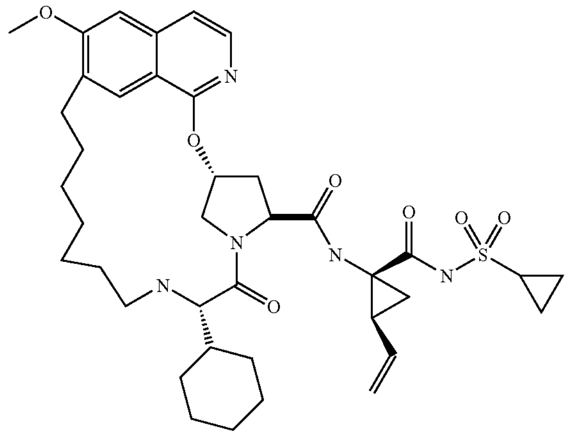 | 735 | 19 |
| 146 | (9R,11S,14S,20E)-14-cyclohexyl-N-((1R,2S)-1-{[(cyclopropylsulfonyl)amino]carbonyl}-2-vinylcyclopropyl)-13-oxo-8-oxa-12,15-diazatetracyclo[20.3.1.1$^{2,6}$.1$^{9,12}$]octacosa-1(26),2(28),3,5,20,22,24-heptaene-11-carboxamide | 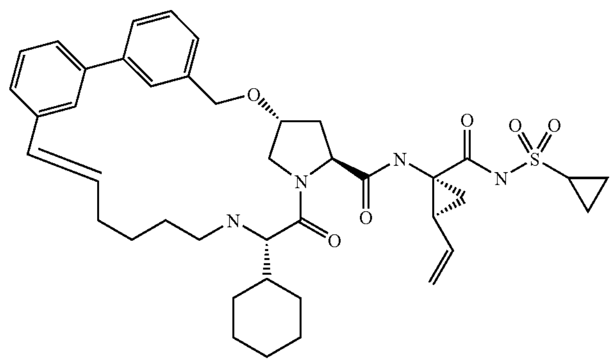 | 729 | 17 |
| 147 | (2R,4S,7S,14E)-7-cyclohexyl-N-((1R,2S)-1-{[(cyclopropylsulfonyl)amino]carbonyl}-2-vinylcyclopropyl)-23-methoxy-12,12-dimethyl-6-oxo-20-phenyl-3,4,6,7,8,9,10,11,12,13-decahydro-2H-16,18-etheno-2,5-methanopyrido[3,4-r][1,5,8]oxadiazacyclononadecine-4-carboxamide | 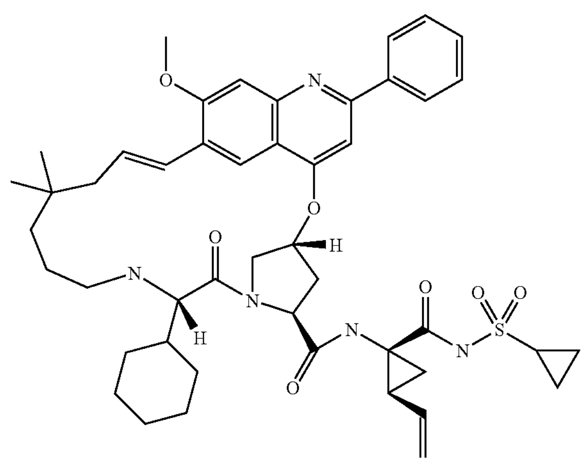 | 838 | 18 |

TABLE 1-continued

| Cmp no. | Chemical name | Structure | Mass spec. (M + 1) | Procedure (Scheme no.) |
|---|---|---|---|---|
| 148 | (2R,4S,7S)-7-cyclohexyl-N-((1R,2S)-1-{[(cyclopropylsulfonyl)amino]carbonyl}-2-vinylcyclopropyl)-23-methoxy-12,12-dimethyl-6-oxo-20-phenyl-3,4,6,7,8,9,10,11,12,13,14,15-dodecahydro-2H-16,18-etheno-2,5-methanopyrido[3,4-r][1,5,8]oxadiaza-cyclononadecine-4-carboxamide | 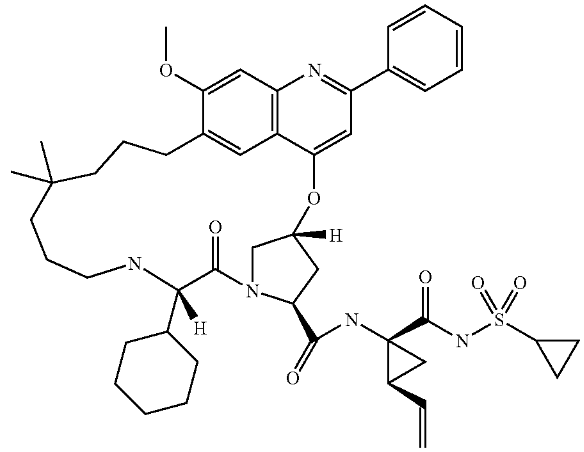 | 840 | 18 |
| 149 | (2R,4S,7S,14Z)-7-cyclohexyl-N-((1R,2S)-1-{[(cyclopropylsulfonyl)amino]carbonyl}-2-vinylcyclopropyl)-23-methoxy-12,12-dimethyl-6-oxo-20-phenyl-3,4,6,7,8,9,10,11,12,13-decahydro-2H-16,18-etheno-2,5-methanopyrido[3,4-r][1,5,8]oxadiaza-cyclononadecine-4-carboxamide | 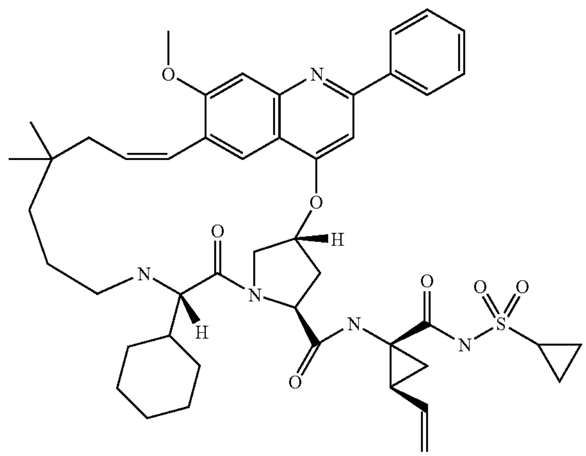 | 838 | 18 |
| 150 | (2R,4S,7S,14E)-7-cyclohexyl-N-((1R,2S)-1-{[(cyclopropylsulfonyl)amino]carbonyl}-2-vinylcyclopropyl)-23-methoxy-12,12-dimethyl-6-oxo-3,4,6,7,8,9,10,11,12,13-decahydro-2H-16,18-(ethanediylidene)-2,5-methanopyrido[3,2-r][1,5,8]oxadiaza-cyclononadecine-4-carboxamide | 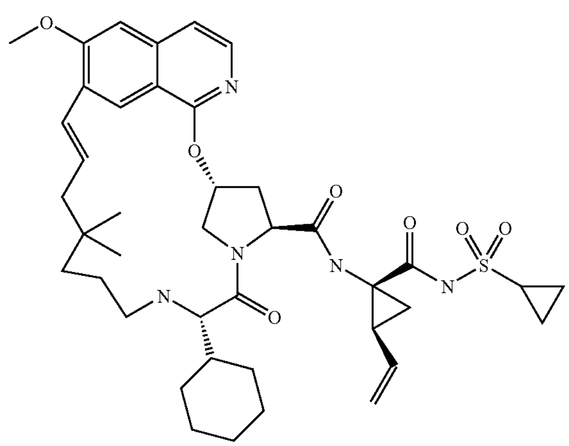 | 761 | 19 |

The invention claimed is:

1. A compound of formula (I):

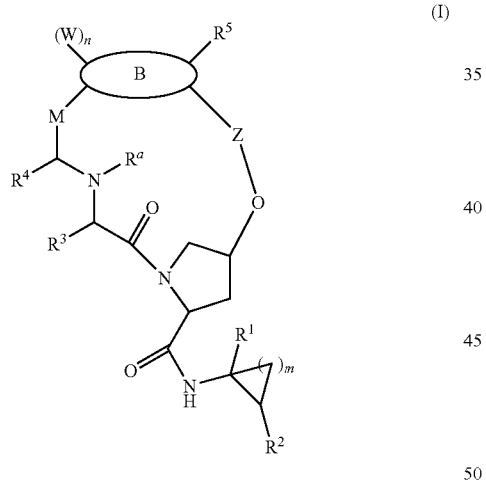

or a pharmaceutically acceptable salt thereof, wherein:

m is 1, 2, 3 or 4;

n is 0, 1 or 2;

$R^1$ is $CO_2R^6$, $CONR^6SO_2R^6$ or $CONR^6SO_2N(R^6)_2$;

$R^2$ is H, $C_{1-6}$alkyl, $C_{2-6}$alkenyl or $C_{3-8}$cycloalkyl, wherein said alkyl, alkenyl or cycloalkyl is optionally substituted with 1 to 3 halo;

$R^3$ is $C_{1-6}$alkyl, $(CH_2)_{0-3}C_{3-8}$cycloalkyl, $(CH_2)_{0-3}$aryl or $(CH_2)_{0-3}$Het, optionally substituted by halo, $OR^6$, $SR^6$, $N(R^6)_2$, $C_{1-6}$alkyl, $NO_2$, $CN$, $CF_3$, $NR^6SO_2R^6$, $SO_2N(R^6)_2$, $NHCO_2R^6$, $NHCOR^6$, $NHCONHR^6$, $CO_2R^6$, $C(O)R^6$ or $CON(R^6)_2$;

$R^4$ is hydrogen, halo, hydroxy, $C_{1-6}$alkyl, $C_{2-6}$alkenyl, $C_{2-6}$alkynyl, $(CH_2)_{0-3}C_{3-8}$cycloalkyl, $(CH_2)_{0-3}$aryl or $C_{1-6}$alkoxy, optionally substituted by halo, $OR^6$, $SR^6$, $N(R^6)_2$, $C_{1-6}$alkyl, $NO_2$, $CN$, $CF_3$ $NR^6SO_2R^6$, $SO_2N(R^6)_2$, $NHCO_2R^6$, $NHCOR^6$, $NHCONHR^6$, $CO_2R^6$, $C(O)R^6$ or $CON(R^6)_2$;

$R^5$ is hydrogen, halo, hydroxy, $C_{1-6}$alkyl, $C_{1-6}$alkoxy, $CN$, $NO_2$, $C_{3-8}$cycloalkyl, $N(R^6)_2$, aryl or heteroaryl, optionally substituted by 1 to 8 halo, $C_{1-4}$alkyl or $N(R^6)_2$;

each $R^6$ is independently hydrogen, $C_{1-6}$alkyl or $C_{3-8}$cycloalkyl;

$R^a$ is hydrogen or $C_{1-4}$alkyl;

or $R^a$ and $R^3$ are joined to form a 5- to 7-membered heterocycle containing 1, 2 or 3 N atoms, which heterocycle is optionally substituted by $C_{1-4}$alkyl;

each W is independently halo, $OR^6$, $C_{1-6}$alkyl, $CN$, $NO_2$, $CF_3$, $OCF_3$, $OCHF_2$, $CO_2R^6$, $CON(R^6)_2$, $COR^6$, $NR^6C(O)R^6$, aryl or heteroaryl;

Z is a bond, —$CH_2$— or C=O;

M is $C_{2-12}$alkylene or $C_{2-12}$alkenylene, optionally substituted by halo, $C_{1-6}$alkyl, $(CH_2)_{0-3}C_{3-8}$cycloalkyl or $(CH_2)_{0-3}$aryl, and optionally containing O, $NR^6$, S, SO or $SO_2$; and ring B is

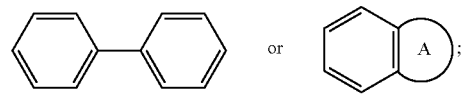

and ring A is pyridinyl, pyrrolidinyl or pyrimidinyl.

2. The compound as claimed in claim 1, wherein the compound is of formula (Io):

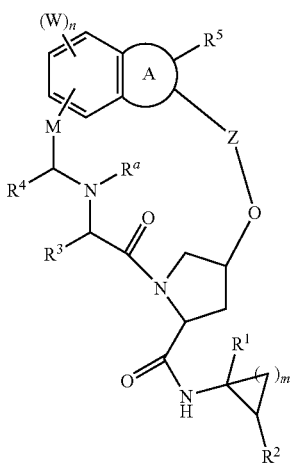

(Io)

or a pharmaceutically acceptable salt thereof,
wherein:
m is 1, 2, 3 or 4;
n is 0, 1 or 2;
$R^1$ is $CO_2R^6$, $CONR^6SO_2R^6$ or $CONR^6SO_2N(R^6)_2$;
$R^2$ is H, $C_{1-6}$alkyl, $C_{2-6}$alkenyl or $C_{3-8}$cycloalkyl, wherein said alkyl, alkenyl or cycloalkyl is optionally substituted with 1 to 3 halo;
$R^3$ is $C_{1-6}$alkyl, $(CH_2)_{0-3}C_{3-8}$cycloalkyl, $(CH_2)_{0-3}$aryl or $(CH_2)_{0-3}$Het, optionally substituted by halo, $OR^6$, $SR^6$, $N(R^6)_2$, $C_{1-6}$alkyl, $NO_2$, CN, $CF_3$, $NR^6SO_2R^6$, $SO_2N(R^6)_2$, $NHCO_2R^6$, $NHCOR^6$, $NHCONHR^6$, $CO_2R^6$, $C(O)R^6$ or $CON(R^6)_2$;
$R^4$ is hydrogen, $C_{1-6}$alkyl, $C_{2-6}$alkenyl, $C_{2-6}$alkynyl, $(CH_2)_{0-3}C_{3-8}$cycloalkyl, $(CH_2)_{0-3}$aryl or $C_{1-6}$alkoxy, optionally substituted by halo, $OR^6$, $SR^6$, $N(R^6)_2$, $C_{1-6}$alkyl, $NO_2$, CN, $CF_3$ $NR^6SO_2R^6$, $SO_2N(R^6)_2$, $NHCO_2R^6$, $NHCOR^6$, $NHCONHR^6$, $CO_2R^6$, $C(O)R^6$ or $CON(R^6)_2$;
$R^5$ is hydrogen, halo, hydroxy, $C_{1-6}$alkyl, $C_{1-6}$alkoxy, CN, $NO_2$, $C_{3-8}$cycloalkyl, $N(R^6)_2$, aryl or heteroaryl, optionally substituted by 1 to 8 halo, $C_{1-4}$alkyl or $N(R^6)_2$;
each $R^6$ is independently hydrogen, $C_{1-6}$alkyl or $C_{3-8}$cycloalkyl;
$R^a$ is hydrogen or $C_{1-4}$alkyl;
or $R^a$ and $R^3$ are joined to form a 5- to 7-membered heterocycle containing 1, 2 or 3 N atoms, which heterocycle is optionally substituted by $C_{1-4}$alkyl;
each W is independently halo, $OR^6$, $C_{1-6}$alkyl, CN, $NO_2$, $CF_3$, $OCF_3$, $OCHF_2$, $CO_2R^6$, $CON(R^6)_2$, $COR^6$, $NR^6C(O)R^6$, aryl or heteroaryl;
Z is a bond or C=O;
M is $C_{2-12}$alkylene or $C_{2-12}$alkenylene, optionally substituted by halo, $C_{1-6}$alkyl, $(CH_2)_{0-3}C_{3-8}$cycloalkyl, or $(CH_2)_{0-3}$aryl, and optionally containing O, $NR^6$, S, SO or $SO_2$; and
ring A is pyridinyl, pyrrolidinyl or pyrimidinyl.

3. The compound as claimed in claim 1, wherein m is 1 or 2.

4. The compound as claimed in claim 1, wherein n is 0 or 1.

5. The compound as claimed in claim 1, wherein $R^1$ is $CO_2R^6$, $CONR^6SO^2R^6$ or $CONR^6SO_2N(R^6)_2$ where $R^6$ is as defined in claim 1.

6. The compound as claimed in claim 1, wherein $R^2$ is $C_{1-6}$alkyl or $C_{2-6}$alkenyl.

7. The compound as claimed in claim 1, wherein $R^3$ is $C_{1-6}$alkyl, or $(CH_2)_{0-3}C_{3-8}$cycloalkyl, optionally substituted by halo, $OR^6$ or $C_{1-6}$alkyl, where $R^6$ is as defined in claim 1.

8. The compound as claimed in claim 1, wherein $R^a$ is hydrogen or $C_{1-2}$alkyl.

9. The compound as claimed in claim 1, wherein $R^a$ and $R^3$ are joined to form a 5- or 6-membered heterocycle containing 1 or 2 N atoms, which heterocycle is optionally substituted by $C_{1-4}$alkyl.

10. The compound as claimed in claim 1, wherein $R^4$ is hydrogen, $C_{1-6}$alkyl, $(CH_2)_{0-3}C_{3-8}$cycloalkyl, $(CH_2)_{0-3}$-phenyl or $C_{1-6}$alkoxy, optionally substituted by halo, $OR^6$, $SR^6$, $N(R^6)_2$, $C_{1-6}$alkyl, $NO_2$ or CN, where $R^6$ is as defined in claim 1.

11. The compound as claimed in claim 1, wherein $R^5$ is hydrogen, halo, hydroxy, $C_{1-6}$alkyl, $C_{1-6}$alkoxy, $C_{3-8}$cycloalkyl, aryl or heteroaryl, optionally substituted by $N(R^6)_2$, where $R^6$ is as defined in claim 1.

12. The compound as claimed in claim 1, wherein each W is independently halo, $OR^6$, $C_{1-6}$alkyl, $CF_3$, $CO_2R^6$, $CON(R^6)_2$, $COR^6$ or $NR^6C(O)R^6$, where $R^6$ is as defined in claim 1.

13. The compound as claimed in claim 1, wherein M is $C_{2-8}$alkylene or $C_{2-8}$alkenylene, optionally substituted by halo, $C_{1-4}$alkyl or $C_{3-6}$cycloalkyl, and optionally containing O.

14. The compound as claimed in claim 1, wherein ring A is pyridinyl or pyrrolidinyl.

15. The compound as claimed in claim 1, wherein the compound is of formula (Ia):

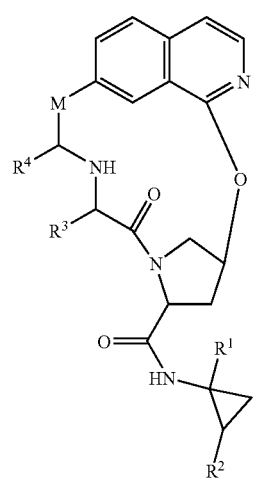

(Ia)

or a pharmaceutically acceptable salt thereof,
wherein $R^1$, $R^2$, $R^3$, $R^4$ and M are as defined in claim 1.

16. The compound as claimed in claim 1, wherein the compound is of formula (Ib):

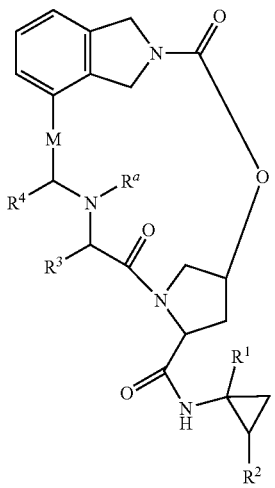

(Ib)

or a pharmaceutically acceptable salt thereof, wherein $R^1$, $R^2$, $R^3$, $R^4$ and M are as defined in claim 1.

17. The compound as claimed in claim 1, wherein the compound is of formula (Ic):

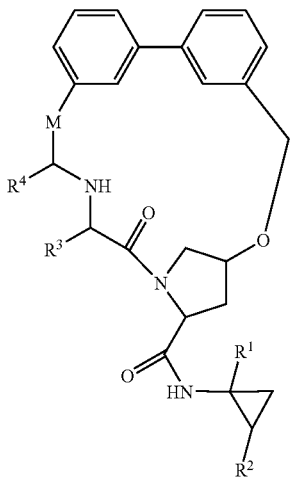

(Ic)

or a pharmaceutically acceptable salt thereof, wherein $R^1$, $R^2$, $R^3$, $R^4$ and M are defined in claim 1.

18. The compound as claimed in claim 1, wherein the compound is of formula (Id):

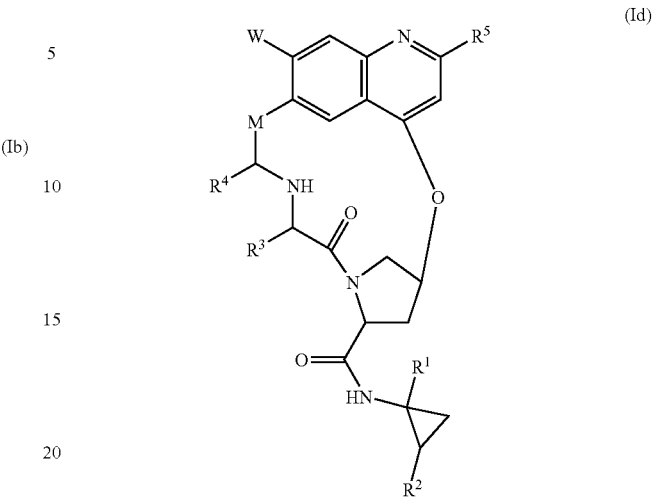

(Id)

or a pharmaceutically acceptable salt thereof, wherein $R^1$, $R^2$, $R^3$, $R^4$, $R^5$, M and W are defined in claim 1.

19. The compound as claimed in claim 1, wherein the compound is selected from:

(5R,7S,10S,12R or S)-N-((1R,2S)-1-{[(cyclopropylsulfonyl)amino]carbonyl}-2-vinylcyclopropyl)-10-isopropyl-3,9-dioxo-12-(trifluoromethyl)-6,7,9,10,11,12,13,14,15,16,17,18-dodecahydro-1H,5H-2,         22:5,8-dimethano-4,2,8,11-benzoxatriazacycloicosine-7-carboxamide, (2R,4S,7S,9R or S)-N-((1R,2S)-1-{[(cyclopropylsulfonyl)amino]carbonyl}-2-vinylcyclopropyl)-7-isopropyl-6-oxo-9-(trifluoromethyl)-3,4,6,7,8,9,10,11,12,13,14,15-dodecahydro-2H-16,18-(ethanediylidene)-2,5-methanopyrido[3,2-r][1,5,8]oxadiazacyclononadecine-4-carboxamide, (5R,7S,10R,17E)-N-((1R,2S)-1-{[(cyclopropylsulfonyl)amino]carbonyl}-2-vinylcyclopropyl)-3,9-dioxo-10-(trifluoromethyl)-6,7,9,10,11,12,13,14,15,16-decahydro-1H,5H-2,         22:5,8-dimethano-4,2,8,11-benzoxatriaza cyc licosine-7-carboxamide, (5R,7S,10S,12R or S)-N-((1R,2S)-1-{[(cyclopropylsulfonyl)amino]carbonyl}-2-vinylcyclopropyl)-10-isopropyl-3,9-dioxo-12-(trifluoromethyl)-6,7,9,10,11,12,13,14,15,16,17,18-dodecahydro-1H,5H-2,         22:5,8-dimethano-4,2,8,11-benzoxatriazacycloicosine-7-carboxamide, (5R,7S,10S,12R or S)-10-cyclohexyl-N-((1R,2S)-1-{[(cyclopropylsulfonyl)amino]carbonyl}-2-vinylcyclopropyl)-3,9-dioxo-12-(trifluoromethyl)-6,7,9,10,11,12,13,14,15,16,17,18-dodecahydro-1H,5H-2,         22:5,8-dimethano-4,2,8,11-benzoxatriazacycloicosine-7-carboxamide, (5R,7S,10S,12R or S)-10-cyclohexyl-N-((1R,2R)-1-[(cyclopropylsulfonyl)amino]carbonyl}-2-ethylcyclopropyl)-3,9-dioxo-12-(trifluoromethyl)-6,7,9,10,11,12,13,14,15,16,17,18-dodecahydro-1H,5H-2,         22:5,8-dimethano-4,2,8,11-benzoxatriazacycloicosine-7-carboxamide, (5R,7S,10S,12R or S)-10-cyclohexyl-N-((1R,2S)-1-{[(cyclopropylsulfonyl)amino]carbonyl}-2-vinylcyclopropyl)-3,9-dioxo-12-(trifluoromethyl)-1,6,7,9,10,11,12,13,14,15,16,17-dodecahydro-5H-2,21:5,8-dimethano-4,2,8,11-benzoxatriazacyclononadecine-7-carboxamide, (2R,4S,7R, 14E)-N-((1R,2S)-1-{[(cyclopropylsulfonyl)amino]carbonyl}-2-vinylcyclopropyl)-6-oxo-7-(trifluoromethyl)-3,4,6,7,8,9,10,11,12,13-decahydro-2H-16,18-(ethanediylidene)-2,5-methanopyrido[3,2-r][1,5,8]oxadiazacyclononadecine-4-carboxamide, (2R,4S,7R)-N-((1R,2S)-1-{[(cyclopropylsulfonyl)amino]carbonyl}-2-vinylcyclopropyl)-6-oxo-7-(trifluoromethyl)-3,4,6,7,8,9,10,11,12,13,14,15-dodecahydro-2H-16,18-etheno-2,5-methanopyrido[3,2-r][1,5,8]oxadiazacyclononadecine-4-carboxamide, (5R,7S,10S,12R or S)-N-((1R,2S)-1-{[(cyclopropylsulfonyl)amino]carbonyl}-2-vinylcyclopropyl)-10-isopropyl-12-methyl-3,9-dioxo-6,7,9,10,11,12,13,14,15,16,17,18-dodecahydro-1H,5H-2, 22:5,8-dimethano-4,2,8,11-benzoxatriazacycloicosine-7-carboxamide, (5R,7S,10S,12R or S)-N-((1R,2S)-1-{[(cyclopropylsulfonyl)amino]carbonyl}-2-vinylcyclopropyl)-10-isopropyl-12-methyl-3,9-dioxo-6,7,9,10,11,12,13,14,15,16,17,18-dodecahydro-1H,5H-2, 22:5,8-dimethano-4,2,8,11-benzoxatriazacycloicosine-7-carboxamide, (5R,7S,10S,17E)-N-((1R,2S)-1-{[(cyclopropylsulfonyl)amino]carbonyl}-2-vinylcyclopropyl)-10-methyl-3,9-dioxo-6,7,9,10,11,12,13,14,15,16-decahydro-1H,5H-2, 22:5,8-dimethano-4,2,8,11-benzoxatriazacycloicosine-7-carboxamide, (5R,7S,10S,7E)-N-((1R,2S)-1-{[(cyclopropylsulfonyl)amino]carbonyl}-2-vinylcyclopropyl)-13,13-difluoro-10-isopropyl-3,9-dioxo-6,7,9,10,11,12,13,14,15,16-decahydro-1H,5H-2, 22:5,8-dimethano-4,2,8,11-benzoxatriazacycloicosine-7-carboxamide, (5R,7S,10S)-N-((1R,2S)-1-{[(cyclopropylsulfonyl)amino]carbonyl}-2-vinylcyclopropyl)-13,13-difluoro-10-isopropyl-3,9-dioxo-6,7,9,10,11,12,13,14,15,16,17,18-dodecahydro-1H,5H-2,22:5,8-dimethano-4,2,8,11-benzoxatriazacycloicosine-7-carboxamide, (5R,7S,10S,12R or S,17E)-N-((1R,2S)-1-{[(cyclopropylsulfonyl)amino]carbonyl}-2-vinylcyclopropyl)-10-isopropyl-12-methyl-3,9-dioxo-6,7,9,10,11,12,13,14,15,16-decahydro-1H,5H-2, 22:5,8-dimethano-4,2,8,11-benzoxatriazacycloicosine-7-carboxamide, (5R,7S,10S,12R or S)-N-((1R,2S)-1-{[(cyclopropylsulfonyl)amino]carbonyl}-2-vinylcyclopropyl)-10-isopropyl-3,9-dioxo-12-(pentafluoroethyl)-6,7,9,10,11,12,13,14,15,16,17,18-dodecahydro-1H,5H-2, 22:5,8-dimethano-4,2,8,11-benzoxatriaza cycloicosine-7-carboxamide, (5R,7S,10S,12R or S)-N-((1R,2R)-1-{[(cyclopropylsulfonyl)amino]carbonyl}-2-ethylcyclopropyl)-10-isopropyl-12-methyl-3,9-dioxo-6,7,9,10,11,12,13,14,15,16,17,18-dodecahydro-1H,5H-2, 22:5,8-dimethano-4,2,8,11-benzoxatriazacycloicosine-7-carboxamide, (5R,7S,10S)-N-((1R,2S)-1-{[(cyclopropylsulfonyl)amino]carbonyl}-2-vinylcyclopropyl)-10-methyl-3,9-dioxo-6,7,9,10,11,12,13,14,15,16,17,18-dodecahydro-1H,5H-2, 22:5,8-dimethano-4,2,8,11-benzoxatriazacycloicosine-7-carboxamide, (5R,7S,10S)-N-((1R,2S)-1-{[(cyclopropylsulfonyl)amino]carbonyl}-2-vinylcyclopropyl)-10-isopropyl-3,9-dioxo-6,7,9,10,11,12,13,14,15,16,17,18-dodecahydro-1H,5H-2, 22:5,8-dimethano-4,2,8,11-benzoxatriazacycloicosine-7-carboxamide, (5R,7S,10S,17E)-N-((1R,2S)-1-{[(cyclopropylsulfonyl)amino]carbonyl}-2-vinylcyclopropyl)-10-isopropyl-3,9-dioxo-6,7,9,10,11,12,13,14,15,16-decahydro-1H,5H-2, 22:5,8-dimethano-4,2,8,11-benzoxatriazacycloicosine-7-carboxamide, (5R,7S,10S,12R or S)-10-cyclohexyl-N-((1R,2S)-1-{[(cyclopropylsulfonyl)amino]carbonyl}-2-vinylcyclopropyl)-12-methyl-3,9-dioxo-6,7,9,10,11,12,13,14,15,16,17,18-dodecahydro-1H,5H-2, 22:5,8-dimethano-4,2,8,11-benzoxatriazacycloicosine-7-carboxamide, (2R,4S,7S,9R or S)-N-((1R,2S)-1-{[(cyclopropylsulfonyl)amino]carbonyl}-2-vinylcyclopropyl)-7-isopropyl-9-methyl-6-oxo-3,4,6,7,8,9,10,11,12,13,14,15-dodecahydro-2H-16,18-etheno-2,5-methanopyrido[3,2-r][1,5,8]oxadiazacyclononadecine-4-carboxamide, (2R,4S,7S,9S or R)-N-((1R,2S)-1-{[(cyclopropylsulfonyl)amino]carbonyl}-2-vinylcyclopropyl)-7-isopropyl-9-methyl-6-oxo-3,4,6,7,8,9,10,11,12,13,14,15-dodecahydro-2H-16,18-etheno-2,5-methanopyrido[3,2-r][1,5,8]oxadiazacyclononadecine-4-carboxamide, (5R,7S,10S,12R or S,7E)-10-cyclohexyl-N-((1R,2S)-1-{[(cyclopropylsulfonyl)amino]carbonyl}-2-vinylcyclopropyl)-12-methyl-3,9-dioxo-6,7,9,10,11,12,13,14,15,16-decahydro-1H,5H-2, 22:5,8-dimethano-4,2,8,11-benzoxatriazacycloicosine-7-carboxamide, (5R,7S,10S,12R or S)-10-cyclohexyl-N-((1R,2S)-1-{[(cyclopropylsulfonyl)amino]carbonyl}-2-vinylcyclopropyl)-12-methyl-3,9-dioxo-6,7,9,10,11,12,13,14,15,16,17,18-dodecahydro-1H,5H-2, 22:5,8-dimethano-4,2,8,11-benzoxatriazacycloicosine-7-carboxamide, (5R,7S,10S,12R or S)-10-cyclohexyl-N-((1R,2S)-1-{[(cyclopropylsulfonyl)amino]carbonyl}-2-vinylcyclopropyl)-11,12-dimethyl-3,9-dioxo-6,7,9,10,11,12,13,14,15,16,17,18-dodecahydro-1H,5H-2, 22:5,8-dimethano-4,2,8,11-benzoxatriazacycloicosine-7-carboxamide, (5R,7S,10S,12R or S,17E)-10-cyclopentyl-N-((1R,2S)-1-{[(cyclopropylsulfonyl)amino]carbonyl}-2-vinylcyclopropyl)-12-methyl-3,9-dioxo-6,7,9,10,11,12,13,14,15,16-decahydro-1H,5H-2, 22:5,8-dimethano-4,2,8,11-benzoxatriazacycloicosine-7-carboxamide, (5R,7,10S,12R or S,17E)-10-cyclopentyl-N-((1R,2S)-1-{[(cyclopropylsulfonyl)amino]carbonyl}-2-vinylcyclopropyl)-12-methyl-3,9-dioxo-6,7,9,10,11,12,13,14,15,16-decahydro-1H,5H-2, 22:5,8-dimethano-4,2,8,11-benzoxatriazacycloicosine-7-carboxamide, (5R,7S,10S,12R or S)-10-cyclopentyl-N-((1R,2S)-1-{[(cyclopropylsulfonyl)amino]carbonyl}-2-vinylcyclopropyl)-12-methyl-3,9-dioxo-6,7,9,10,11,12,13,14,15,16,17,18-dodecahydro-1H,5H-2, 22:5,8-dimethano-4,2,8,11-benzoxatriaza cycloicosine-7-carboxamide, (1R,2S)-1-({[(5R,7S,10S,12R or S,17E)-10-cyclohexyl-12-methyl-3,9-dioxo-6,7,9,10,11,12,13,14,15,16-decahydro-1H,5H-2, 22:5,8-dimethano-4,2,8,11-benzoxatriazacycloicosin-7-yl]carbonyl}amino)-2-vinylcyclopropanecarboxylic acid, (5R,7S,10S,12R or S)-N-((1R,2R)-1-{[(cyclopropylsulfonyl)amino]carbonyl}-2-ethylcyclo propyl)-12-methyl-10-[(1S)-1-methylpropyl]-3,9-dioxo-6,7,9,10,11,12,13,14,15,16,17,18-dodecahydro-1H,5H-2, 22:5,8-dimethano-4,2,8,111-benzoxatriazacycloicosine-7-carboxamide, (2R,4S,7S,14E)-7-cyclopentyl-N-((1R,2S)-1-{[(cyclopropylsulfonyl)amino]carbonyl}-2-vinylcyclopropyl)-6-oxo-3,4,6,7,8,9,10,11,12,13-decahydro-2H-16,18-etheno-2,5-methanopyrido[3,2-r][1,5,8]oxadiazacyclononadecine-4-carboxamide, (2R,4S,7S)-7-cyclopentyl-N-((1R,2S)-1-{[(cyclopropylsulfonyl)amino]carbonyl}-2-vinylcyclopropyl)-6-oxo-3,4,6,7,8,9,10,11,12,13,14,15-dodecahydro-2H-16,18-etheno-2,5-methanopyrido[3,2-r][1,5,8]oxadiazacyclononadecine-4-carboxamide, (3S,3aR,6S,8R)-N-((1R,2S)-1-{[(cyclopropylsulfonyl)amino]carbonyl}-2-vinylcyclopropyl)-3-methyl-4,10-dioxo-2,3,3a,4,7,8,12,17,18,19,20,21,22,23-tetradecahydro-1H,6H-5, 8:11,13-dimethanopyrrolo[2,1-j][4,2,8,11]benzoxatriazacycloicosine-6-carboxamide, (5R,7S,10S)-10-cyclopentyl-N-((1R,2S)-1-{[(cyclopropylsulfonyl)amino]carbonyl}-2-vinylcyclopropyl)-11-methyl-3,9-dioxo-6,7,10,11,12,13,15,16,17,18-decahydro-1H,5H,9H-2, 22:5,8-dimethano-4,14,2,8,11-benzodioxatriazacycloicosine-7-carboxamide, (5R,7S,10S)-10-cyclopentyl-N-((1R,2S)-1-{[(cyclopropylsulfonyl)amino]carbonyl}-2-vinylcyclopropyl)-13,13-dimethyl-3,9-dioxo-6,7,9,10,11,12,13,14,15,16,17,18-dodecahydro-1H,5H-2,22:5,8-dimethano-4,2,8,11-benzoxatriazacycloicosine-7-carboxamide, (5R,7S,10S)-10-cyclopentyl-N-((1R,2S)-1-{[(cyclopropylsulfonyl)amino]carbonyl}-2-vinylcyclopropyl)-11,13,13-trimethyl-3,9-dioxo-6,7,9,10,11,12,13,14,15,16,17,18-dodecahydro-1H,5H-2, 22:5,8-dimethano-4,2,8,11-benzoxatriazacycloicosine-7-carboxamide, (2R,4S,7S,14E)-7-cyclohexyl-N-((1R,2S)-1-{[(cyclopropylsulfonyl)amino]carbonyl}-2-vinylcyclopropyl)-23-methoxy-6-oxo-20-phenyl-3,4,6,7,8,9,10,11,12,13-decahydro-2H-16,18-etheno-2,5-methanopyrido[3,4-r][1,5,8]oxadiazacyclononadecine-4-carboxamide, (2R,4S,7S)-7-cyclohexyl-N-((1R,2S)-1-{[(cyclopropylsulfonyl)amino]carbonyl}-2-vinylcyclopropyl)-23-methoxy-6-oxo-20-phenyl-3,4,6,7,8,9,10,11,12,13,14,15-dodecahydro-2H-16,18-etheno-2,5-methanopyrido[3,4-r][1,5,8]oxadiazacyclononadecine-4-carboxamide, (2R,4S,7S,15E)-7-cyclohexyl-N-((1R,2S)-1-{[(cyclopropylsulfonyl)amino]carbonyl}-2-vinylcyclopropyl)-24-methoxy-6-oxo-21-phenyl-3,4,7,8,9,10,11,12,13,14-decahydro-2H,6H-17,19-etheno-2,5-methanopyrido[3,4-s][1,5,8]oxadiazacycloicosine-4-carboxamide, (2R,4S,7S)-7-cyclohexyl-N-((1R,2S)-1-{[(cyclopropylsulfonyl)amino]carbonyl}-2-vinylcyclopropyl)-24-methoxy-6-oxo-21-phenyl-3,4,7,8,9,10,11,12,13,14,15,16-dodecahydro-2H,6H-17,19-etheno-2,5-methanopyrido[3,4-s][1,5,8]oxadiazacycloicosine-4-carboxamide, (9R,11S,14S)-14-tert-butyl-N-((1R,2S)-1-{[(cyclopropylsulfonyl)amino]carbonyl}-2-vinylcyclopropyl)-13-oxo-8-oxa-12,15-diazatetracyclo[20.3.1.1$^{2,6}$.1$^{9,12}$]octacosa-1(26),2(28),3,5,22,24-hexaene-11-carboxamide, (2R,4S,7S,14Z)-7-cyclohexyl-N-((1R,2S)-1-{[(cyclopropylsulfonyl)amino]carbonyl}-2-vinylcyclopropyl)-23-methoxy-6-oxo-3,4,6,7,8,9,10,11,12,13-decahydro-2H-16,18-(ethanediylidene)-2,5-methanopyrido[3,2-r][1,5,8]oxadiazacyclononadecine-4-carboxamide, (2R,4S,7S,14E)-7-cyclohexyl-N-((1R,2S)-1-{[(cyclopropylsulfonyl)amino]carbonyl}-2-vinylcyclopropyl)-23-methoxy-6-oxo-3,4,6,7,8,9,10,11,12,13-decahydro-2H-16,18-(ethanediylidene)-2,5-methanopyrido[3,2-r][1,5,8]oxadiazacyclo nonadecine-4-carboxamide, (2R,4S,7S)-7-cyclohexyl-N-((1R,2S)-1-{[(cyclopropylsulfonyl)amino]carbonyl}-2-vinylcyclopropyl)-23-methoxy-6-oxo-3,4,6,7,8,9,10,11,12,13,14,15-dodecahydro-2H-16,18-(ethanediylidene)-2,5-methanopyrido[3,2-r][1,5,8]oxadiazacyclononadecine-4-carboxamide, (9R,11S,14S,20E)-14-cyclohexyl-N-((1R,2S)-1-{[(cyclopropylsulfonyl)amino]carbonyl}-2-vinylcyclopropyl)-13-oxo-8-oxa-12,15-diazatetracyclo[20.3.1.1$^{2,6}$.1$^{9,12}$]octacosa-1(26),2(28),3,5,20,22,24-heptaene-11-carboxamide, (2R,4S,7S,14E)-7-cyclohexyl-N-((1R,2S)-1-{[(cyclopropylsulfonyl)amino]carbonyl}-2-vinyl cyclopropyl)-23-methoxy-12,12-dimethyl-6-oxo-20-phenyl-3,4,6,7,8,9,10,11,12,13-decahydro-2H-16,18-etheno-2,5-methanopyrido[3,4-r][1,5,8]oxadiazacyclononadecine-4-carboxamide, (2R,4S,7S)-7-cyclohexyl-N-((1R,2S)-1-{[(cyclopropylsulfonyl)amino]carbonyl}-2-vinylcyclopropyl)-23-methoxy-12,12-dimethyl-6-oxo-20-phenyl-3,4,6,7,8,9,10,11,12,13,14,15-dodecahydro-2H-16,18-etheno-2,5-methanopyrido[3,4-r][1,5,8]oxadiazacyclononadecine-4-carboxamide, (2R,4S,7S,14Z)-7-cyclohexyl-N-((1R,2S)-1-{[(cyclopropylsulfonyl)amino]carbonyl}-2-vinyl cyclopropyl)-23-methoxy-12,12-dimethyl-6-oxo-20-phenyl-3,4,6,7,8,9,10,11,12,13-decahydro-2H-16,18-etheno-2,5-methanopyrido[3,4-r][1,5,8]oxadiazacyclononadecine-4-carboxamide, (2R,4S,7S,14E)-7-cyclohexyl-N-((1R,2S)-1-{[(cyclopropylsulfonyl)amino]carbonyl}-2-vinyl cyclopropyl)-23-methoxy-12,12-dimethyl-6-oxo-3,4,6,7,8,9,10,11,12,13-decahydro-2H-16,18-(ethanediylidene)-2,5-methanopyrido[3,2-r][1,5,8]oxadiazacyclononadecine-4-carboxamide, or a pharmaceutically acceptable salt thereof.

20. A pharmaceutical composition comprising a compound of formula (I):

$$(I)$$

or a pharmaceutically acceptable salt thereof,
wherein:
m is 1, 2, 3 or 4:
n is 0, 1 or 2:
$R^1$ is $CO_2R^6$, $CONR^6SO_2$, $R^6$ or $CONR^6SO_2N(R^6)_2$,
$R^2$ is H, $C_{1-6}$-alkyl, $C_{2-6}$alkenyl or $C_{3-8}$cycloalkyl, wherein said alkyl, alkenyl or cycloalkyl is optionally substituted with 1 to 3 halo,
$R^3$ is $C_{1-6}$alkyl $(CH_2)_{0-3}C_{3-8}$ cycloalkyl $(CH_2)_{0-3}$aryl or $(CH_2)_{0-3}$Het, optionally substituted by halo, $OR^6$, $SR^6N(R^6)_2$ $C_1$alkyl NO, CN, $CF_3$, $NR^6SO_2R^6$, $SO_2N(R^6)_2$, $NHCO_2R^6NHCOR^6$, $NHCONHR^6$, $CO_2R^6$, $C(O)R^6$ or $CON(R^6)_2$;
$R^4$ is hydrogen, halo, hydroxy, $C_{1-6}$alkyl, $C_{2-6}$alkenyl $C_{2-6}$alkynyl $(CH_2)_{0-3}C_{3-8}$ cycloalkyl $(CH_2)_{0-3}$aryl or $C_{1-6}$alkoxy, optionally substituted by halo, $OR^6$, $SR^6N(R^6)_2$ $C_{1-6}$alkyl, $NO_2$, CN $CF_3$ $NR^6SO_2R^6$, $SO_2N(R^6)_2$, $NHCO_2R^6$, $NHCOR^6$, $NHCONHR^6CO_2R^6$, $C(O)R^6$ or $CON(R^6)_2$;
$R^5$ is hydrogen, halo, hydroxy, $C_{1-6}$alkyl, $C_{1-6}$alkoxy, CN, $NO_2$, $C_{3-8}$cycloalkyl, $N(R^6)_2$, aryl or heteroaryl, optionally substituted by 1 to 8 halo, $C_{1-4}$alkyl or $N(R^6)_2$;

each $R^6$ is independently hydrogen, $C_{1-6}$alkyl or $C_{3-8}$cycloalkyl;
$R^a$ is hydrogen or $C_{1-4}$alkyl;
or $R^a$ and $R^3$ are joined to form a 5- to 7-membered heterocycle containing 1, 2 or 3 N atoms, which heterocycle is optionally substituted by $C_{1-4}$alkyl;
each W is independently halo, $OR^6$, $C_{1-6}$alkyl, CN, $NO_2$, $CF_3$, $OCF_3$, $OCHF_2$, $CO_2R^6$, $CON(R^6)_2$ $COR^6$, $NR^6C(O)R^6$, aryl or heteroaryl;
Z is a bond, —$CH_2$— or C═O.
M is $C_{2-12}$alkylene or $C_{2-12}$alkenylene, optionally substituted by halo, $C_{1-6}$alkyl, $(CH_2)_{0-3}C_{3-8}$cycloalkyl or $(CH_2)_{0-3}$aryl, and optionally containing O, $NR^6$, S, SO or $SO_2$; and
ring B is

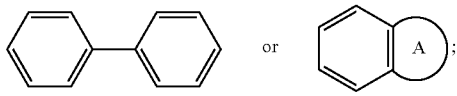

and
ring A is pyridinyl, pyrrolidinyl or pyrimidinyl.
in association with a pharmaceutically acceptable carrier.

21. The pharmaceutical composition as claimed in claim 20, further comprising one or more other agents for the treatment of viral infections, or an immunomodulatory agent.

22. A method of inhibiting hepatitis C virus protease and/or of treating hepatitis C virus, the method involving administering to a human or animal subject suffering from the condition a therapeutically or prophylactically effective amount of compound of formula (I):

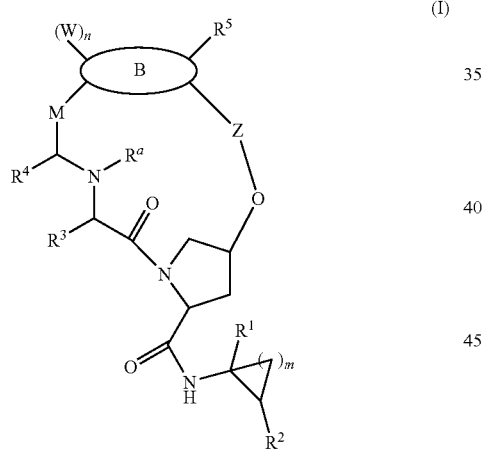

(I)

or a pharmaceutically acceptable salt thereof, wherein:
m is 1,2, 3 or 4;
n is 0,1 or 2:
$R^1$ is $CO_2R^6$$CONR^6SO_2R^6$ or $CONR^6SO_2N(R^6)_2$,
$R^2$ is H, $C_{1-6}$alkyl, $C_{2-6}$alkenyl or $C_{3-8}$cycloalkyl, wherein said alkyl, alkenyl or cycloalkyl is optionally substituted with 1 to 3 halo;
$R^3$ is $C_{1-6}$alkyl, $(CH_2)_{0-3}C_{3-8}$cycloalkyl, $(CH_2)_{0-3}$aryl or $(CH_2)_{0-3}$Het, optionally substituted by halo, $OR^6$, $SR^6$. $N(R^6)_2C_{1-6}$alkyl $NO_2$, CN, $CF_3$, $NR^6SO_2R^6$, $SO_2N(R^6)$, $NHCO_2R^6$, $NHCOR^6$$NHCONHR^6$, $CO_2R^6$, $C(O)R^6$ or $CON(R^6)_2$;
$R^4$ is hydrogen, halo, hydroxy, $C_{1-6}$alkyl $C_{2-6}$alkenyl, $C_{2-6}$alkynyl, $(CH_2)_{0-3}C_{3-8}$cycloalkyl, $(CH_2)_{0-3}$aryl $C_{1-6}$alkoxy, optionally substituted by halo, $OR^6$, $SR^6$, $N(R^6)_2$, $C_{1-6}$alkyl, $NO_2$, CN, $CF_3$ $NR^6SO_2R^6$, $SO_2N(R^6)_2$, $NHCO_2R^6$, $NHCOR^6$, $NHCONHR^6CO_2R^6C(O)R^6$ or $CON(R^6)_2$;
$R^5$ is hydrogen, halo, hydroxy, $C_{1-6}$alkyl, $C_{1-6}$alkoxy, CN, $NO_2$, $C_{3-8}$cycloalkyl, $N(R^6)_2$, aryl or heteroaryl, optionally substituted by 1 to 8 halo, $C_{1-4}$alkyl or $N(R^6)$;
each $R^6$ is independently hydrogen, $C_{1-6}$alkyl or $C_{3-8}$cycloalkyl;
$R^a$ is hydrogen or $C_{1-4}$alkyl;
or $R^a$ and $R^3$ are joined to form a 5- to 7-membered heterocycle containing 1.2 or 3 N atoms, which heterocycle is optionally substituted by $C_{1-4}$alkyl;
each W is independently halo, $OR^6$, $C_{1-6}$alkyl, CN, $NO_2$, $CF_3$, $OCF_3$, $OCHF_2$, $CO_2R^6$, $CON(R^6)_2$, $COR^6$, $NR^6C(O)R^6$ aryl or heteroaryl;
Z is a bond, —$CH_2$— or C═O;
M is $C_{2-12}$alkylene or $C_{2-12}$alkenylene, optionally substituted by halo, $C_{1-6}$alkyl, $(CH_2)_{0-3}C_{3-8}$cycloalkyl or $(CH_2)_{0-3}$aryl, and optionally containing O, $NR^6$, S, SO or $SO_2$; and
ring B is

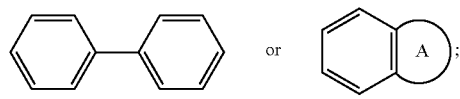

and
ring A is pyridinyl pyrrolidinyl or pyrimidinyl.

* * * * *

UNITED STATES PATENT AND TRADEMARK OFFICE
CERTIFICATE OF CORRECTION

PATENT NO. : 8,314,062 B2  
APPLICATION NO. : 12/306137  
DATED : November 20, 2012  
INVENTOR(S) : Benedetta Crescenzi et al.

Page 1 of 1

It is certified that error appears in the above-identified patent and that said Letters Patent is hereby corrected as shown below:

Title Page, Item (73) Assignee, delete:

"Instituto di Ricerche di Biologia Molecolare P. Angeletti S.p.A., Rome (IT)"

and insert

-- Istituto di Ricerche di Biologia Molecolare P. Angeletti S.p.A., Roma (IT) --

Signed and Sealed this  
Sixth Day of August, 2013

Teresa Stanek Rea  
*Acting Director of the United States Patent and Trademark Office*

SEQUENCE LISTING

<160> NUMBER OF SEQ ID NOS: 1

<210> SEQ ID NO 1

```
<211> LENGTH: 11
<212> TYPE: PRT
<213> ORGANISM: Artificial Sequence
<220> FEATURE:
<223> OTHER INFORMATION: Protease Substrate
<221> NAME/KEY: ACETYLATION
<222> LOCATION: 1
<221> NAME/KEY: AMIDATION
<222> LOCATION: 11
<221> NAME/KEY: SITE
<222> LOCATION: 1
<223> OTHER INFORMATION: Europium label
<221> NAME/KEY: MOD_RES
<222> LOCATION: 7
<223> OTHER INFORMATION: Abu
<221> NAME/KEY: SITE
<222> LOCATION: 8
<223> OTHER INFORMATION: 2-hydroxy propanoic acid
<221> NAME/KEY: SITE
<222> LOCATION: (11)...(11)
<223> OTHER INFORMATION: QSY-7 label
<221> NAME/KEY: THIOLEST
<222> LOCATION: (7)...(8)

<400> SEQUENCE: 1

Cys Asp Asp Met Glu Glu Xaa Xaa Ser Ala Lys
1               5                   10
```